US007834023B2

(12) United States Patent
Scarborough et al.

(10) Patent No.: US 7,834,023 B2
(45) Date of Patent: Nov. 16, 2010

(54) SUBSTITUTED DIHYDROQUINAZOLINES AS PLATELET ADP RECEPTOR INHIBITORS

(75) Inventors: Robert M. Scarborough, Half Moon Bay, CA (US); Carroll Anna Crew, legal representative, Half Moon Bay, CA (US); Shawn M. Bauer, Pacifica, CA (US); Anjali Pandey, Fremont, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 51 days.

(21) Appl. No.: 11/856,616

(22) Filed: Sep. 17, 2007

(65) Prior Publication Data

US 2008/0132499 A1  Jun. 5, 2008

Related U.S. Application Data

(60) Provisional application No. 60/846,328, filed on Sep. 20, 2006.

(51) Int. Cl.
*A61K 31/517* (2006.01)
(52) U.S. Cl. .................. 514/266.3; 544/116; 544/285; 548/128; 548/131; 548/254; 549/59
(58) Field of Classification Search ............. 514/266.3; 544/116, 285; 548/128, 131, 254; 549/59
See application file for complete search history.

(56) References Cited

U.S. PATENT DOCUMENTS

| 6,172,072 | B1 | 1/2001 | Lubisch et al. | |
|---|---|---|---|---|
| 6,436,949 | B1 * | 8/2002 | Lubisch et al. | 514/274 |
| 6,906,063 | B2 * | 6/2005 | Scarborough et al. | 514/222.8 |
| 2003/0199530 | A1 | 10/2003 | Goldstein et al. | |
| 2007/0010537 | A1 * | 1/2007 | Hamamura et al. | 514/266.2 |

FOREIGN PATENT DOCUMENTS

| WO | WO 00/55153 A | 9/2000 |
|---|---|---|
| WO | WO 2005/032488 A | 4/2005 |
| WO | WO 2005/123696 A | 12/2005 |
| WO | WO 2006/039212 A | 4/2006 |
| WO | WO 2007/149031 A | 12/2007 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Ling et al., "Syntheses and electronic structures of benzannelated isoquinolinones and their photoinduced cycloaddition reactions with electron deficient alkenes." Database CA (Online), Chemical Abstracts Service, Columbus, OH., 1998. Retrieved from STN, Database Accession No. 1998:776006.
Meyer, Hans, "The linking of aromatic amino acids." Database CA (Online), Chemical Abstracts Service, Columbus, OH, 1907. Retrieved from STN Database Accession No. 1907:7147.
Wawrzyniak et al., "Printing polyamide fabrics with pastes containing active and passive agents for color formation." Database CA (Online), Chemical Abstracts Service, Columbus, OH., Oct. 31, 1985, Retrieved from STN Database Accession No. 1991:25763.

* cited by examiner

*Primary Examiner*—James O Wilson
*Assistant Examiner*—Douglas M Willis
(74) *Attorney, Agent, or Firm*—Townsend and Townsend and Crew LLP

(57) ABSTRACT

Compounds of formula I are provided:

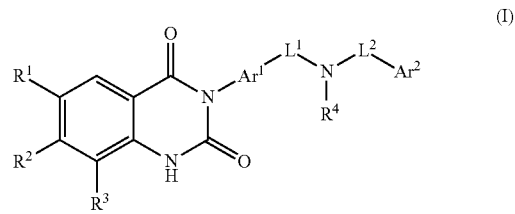

wherein $Ar^1$ and $Ar^2$ are substituted aromatic rings and $L^1$ and $L^2$ are independent divalent linking groups. The compounds are useful as platelet ADP receptor inhibitors, for treating thrombosis and for reducing the likelihood and/or severity of a secondary ischemic event in a patient.

26 Claims, No Drawings

SUBSTITUTED DIHYDROQUINAZOLINES AS PLATELET ADP RECEPTOR INHIBITORS

CROSS-REFERENCES TO RELATED APPLICATIONS

The present application claims priority to U.S. Ser. No. 60/846,328 filed Sep. 20, 2006 herein incorporated by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

Thrombotic complications are a major cause of death in the industrialized world. Examples of these complications include acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura. Thrombotic and restenotic complications also occur following invasive procedures, e.g., angioplasty, carotid endarterectomy, post CABG (coronary artery bypass graft) surgery, vascular graft surgery, stent placements and insertion of endovascular devices and prostheses. It is generally thought that platelet aggregates play a critical role in these events. Blood platelets, which normally circulate freely in the vasculature, become activated and aggregate to form a thrombus with disturbed blood flow caused by ruptured atherosclerotic lesions or by invasive treatments such as angioplasty, resulting in vascular occlusion. Platelet activation can be initiated by a variety of agents, e.g., exposed subendothelial matrix molecules such as collagen, or by thrombin which is formed in the coagulation cascade.

An important mediator of platelet activation and aggregation is ADP (adenosine 5'-diphosphate) which is released from blood platelets in the vasculature upon activation by various agents, such as collagen and thrombin, and from damaged blood cells, endothelium or tissues. Activation by ADP results in the recruitment of more platelets and stabilization of existing platelet aggregates. Platelet ADP receptors mediating aggregation are activated by ADP and some of its derivatives and antagonized by ATP (adenosine 5'-triphosphate) and some of its derivatives (Mills, D. C. B. (1996) Thromb. Hemost. 76:835-856). Therefore, platelet ADP receptors are members of the family of P2 receptors activated by purine and/or pyrimidine nucleotides (King, B. F., Townsend-Nicholson, A. & Burnstock, G. (1998) Trends Pharmacol. Sci. 19:506-514).

Recent pharmacological data using selective antagonists suggests that ADP-dependent platelet aggregation requires activation of at least two ADP receptors (Kunapuli, S. P. (1998), Trends Pharmacol. Sci. 19:391-394; Kunapuli, S. P. & Daniel, J. L. (1998) Biochem. J. 336:513-523; Jantzen, H. M. et al. (1999) Thromb. Hemost. 81:111-117). One receptor appears to be identical to the cloned $P2Y_1$ receptor, mediates phospholipase C activation and intracellular calcium mobilization and is required for platelet shape change. The second platelet ADP receptor important for aggregation mediates inhibition of adenylyl cyclase. Molecular cloning of the gene or cDNA for this receptor ($P2Y_{12}$) has recently been reported (Hollopeter, G. et. al. (2001) Nature 409:202-207). Based on its pharmacological and signaling properties this receptor has been previously termed $P^2Y_{ADP}$ (Fredholm, B. B. et al. (1997) TIPS 18:79-82), $P2T_{AC}$ (Kunapuli, S. P. (1998), Trends Pharmacol. Sci. 19:391-394) or P2Ycyc (Hechler, B. et al. (1998) Blood 92, 152-159).

Various directly or indirectly acting synthetic inhibitors of ADP-dependent platelet aggregation with antithrombotic activity have been reported. The orally active antithrombotic thienopyridines ticlopidine and clopidogrel inhibit ADP-induced platelet aggregation, binding of radiolabeled ADP receptor agonist 2-methylthioadenosine 5'-diphosphate to platelets, and other ADP-dependent events indirectly, probably via formation of an unstable and irreversible acting metabolite (Quinn, M. J. & Fitzgerald, D. J. (1999) Circulation 100:1667-1667). Some purine derivatives of the endogenous antagonist ATP, e.g., AR-C (formerly FPL or ARL) 67085MX and AR-C69931MX, are selective platelet ADP receptor antagonists which inhibit ADP-dependent platelet aggregation and are effective in animal thrombosis models (Humphries et al. (1995), Trends Pharmacol. Sci. 16, 179; Ingall, A. H. et al. (1999) J. Med. Chem. 42, 213-230). Novel triazolo[4,5-d]pyrimidine compounds have been disclosed as $P_{2T}$-antagonists (WO 99/05144). Tricyclic compounds as platelet ADP receptor inhibitors have also been disclosed in WO 99/36425. Piperazine derivatives are described in WO 02/098856. The target of these antithrombotic compounds appears to be the platelet ADP receptor mediating inhibition of adenylyl cyclase or $P2Y_{12}$.

Despite these compounds, there exists a need for more effective platelet ADP receptor inhibitors. In particular, there is a need for platelet ADP receptor inhibitors having antithrombotic activity that are useful in the prevention and/or treatment of cardiovascular diseases, particularly those related to thrombosis.

BRIEF SUMMARY OF THE INVENTION

The present invention provides compounds having the formula:

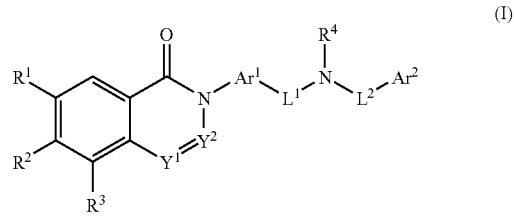

and pharmaceutically acceptable salts thereof.

The symbol $Y^1$ represents a member selected from the group consisting of N, NH, O, $CR^5$ and $CH_2$.

The symbol $Y^2$ is selected from the group consisting of CO, $CH_2$, CH and N.

Each symbol $R^1$, $R^2$ and $R^3$ is independently selected from the group consisting of H, $C_{1-6}$alkyl, $C_{2-6}$ alkenyl, $C_{2-6}$ alkynyl, —$NR^7_2$, $C_{1-6}$alkoxy, halogen, $C_{1-6}$haloalkyl, hydroxy$C_{1-6}$alkyl, cyano, —$C(O)R^6$, $C_{3-6}$cycloalkyl, $C_{3-6}$cycloalkyl-$C_{1-6}$alkyl, aryl and aryl$C_{1-6}$alkyl, wherein each of said $C_{1-6}$alkyl, $C_{2-6}$ alkenyl, $C_{2-6}$ alkynyl and aryl portions is optionally substituted with from 1 to 3 substituents, each independently selected from the group consisting of $C_{1-6}$ alkyl, $C_{2-6}$ alkenyl, $C_{2-6}$ alkynyl, amino, $C_{1-6}$alkoxy, halogen, hydroxyl, cyano, oxo, thio, $C_{3-6}$cycloalkyl, aryl and heteroaryl.

The symbol $R^4$ is H or —$(CH_2)_m CO_2 H$.

The symbol $R^5$ is selected from H, $C_{1-6}$alkyl, cyano, halogen, halo$C_{1-6}$alkyl, aryl, aryl$C_{1-6}$alkyl and —$C(O)R^6$.

The symbol $R^6$ is selected from the group consisting of H, hydroxy, $C_{1-6}$alkyl, $C_{1-6}$alkoxy, heterocyclyl$C_{1-6}$alkoxy and —$NR^7_2$.

Each symbol $R^7$ is independently selected from the group consisting of H, $C_{1-6}$alkyl and aryl$C_{1-6}$alkyl or optionally, two $R^7$ groups attached to nitrogen are combined with the nitrogen atom to form an azetidine, pyrrolidine, piperidine or morpholine ring; wherein each of said $C_{1-6}$ alkyl and aryl$C_{1-6}$ alkyl is optionally substituted with from 1 to 3 substituents, each independently selected from the group consisting of halogen, amino, hydroxyl, $C_{1-6}$ alkoxy, cyano, $C_{1-6}$ alkyl, $C_{3-6}$ cycloalkyl, aryl, and heteroaryl.

Each symbol $Ar^1$ and $Ar^2$ represents an aromatic ring selected from the group consisting of benzene, pyridine, pyrazine, pyrimidine, tetrazole and thiophene, each of which is optionally substituted with from 1-2$R^8$ substituents.

Each symbol $R^8$ independently represents a member selected from the group consisting of halogen, cyano, hydroxy, $C_{1-6}$alkyl, $C_{2-6}$alkenyl, $C_{2-6}$alkynyl, $C_{1-6}$alkoxy, halo$C_{1-6}$alkyl, halo$C_{1-6}$alkoxy, $C_{3-5}$cycloalkyl-$C_{1-6}$alkoxy, —$NR^7$, —$C(=NR^{8a})$—$N(R^{8b})_2$, —$C(O)R^{8a}$, —$O(CH_2)_m OR^{8b}$, —$(CH_2)_m OR^{8b}$, —$O(CH_2)_m N(R^{8b})_2$ and —$(CH_2)_m N(R^{8b})_2$.

Each symbol $R^{8a}$ represents a member independently selected from the group consisting of H, hydroxy, $C_{1-6}$alkyl, $C_{1-6}$alkoxy and —$NR^7$.

Each symbol $R^{8b}$ represents a member independently selected from the group consisting of H, $C_{1-4}$ alkyl and $C_{1-4}$alkanoyl, and optionally, two $R^{8b}$ groups attached to nitrogen are combined with the nitrogen atom to form an azetidine, pyrrolidine, piperidine or morpholine ring; wherein each of said $C_{1-4}$ alkyl and $C_{1-4}$ alkanoyl is optionally substituted with from 1 to 3 substituents, each independently selected from the group consisting of halogen, amino, hydroxyl, $C_{1-6}$ alkoxy, cyano, $C_{1-6}$ alkyl, $C_{3-6}$ cycloalkyl, aryl, and heteroaryl.

The symbol $L^1$ represents a linking group selected from the group consisting of a bond, —CO—, —$CH_2$—, —NHCO— and —$CH_2 CO$—.

The symbol $L^2$ is a linking group selected from the group consisting of a bond, —$CR^9_2$—, —$CR^9_2 CH_2$— and —CO—.

Each symbol $R^9$ represents a member independently selected from the group consisting of H, $C_{1-6}$alkyl, hydroxyalkyl, —$(CH_2)_m C(O)R^6$, —$C(O)R^6$ and heterocyclyl substituted with from 0 to 2 substituents selected from the group halogen, cyano, $C_{1-6}$alkyl, $C_{2-6}$alkenyl, $C_{2-6}$alkynyl, $C_{1-6}$alkoxy, halo$C_{1-6}$alkyl, oxo and thio.

Each subscript m is independently 1, 2 or 3.

In addition to the compounds provided herein, the present invention further provides pharmaceutical compositions comprising those compounds, as well as methods for the use of the compounds in treating thrombosis as well as preventing the occurrence of a secondary ischemic event.

BRIEF DESCRIPTION OF THE DRAWINGS

Not applicable.

DETAILED DESCRIPTION OF THE INVENTION

Definitions

The terms "treat", "treating" and "treatment" refer to any method of alleviating or abrogating a disease or its attendant symptoms.

The term "therapeutically effective amount" refers to that amount of the compound being administered sufficient to prevent or decrease the development of one or more of the symptoms of the disease, condition or disorder being treated.

The term "inhibit" refers to the ability of a compound to decrease the function, or activity, of the associated activity (e.g., ADP). "Inhibition", as used herein in its various forms, is meant to include antagonism and partial antagonism of the activity associated with ADP. Inhibitors of ADP are compounds that, e.g., bind to, partially or totally block the enzyme's activity.

The term "compound" as used herein is intended to encompass not only the specified molecular entity but also its pharmaceutically acceptable, pharmacologically active derivatives, including, but not limited to, salts, prodrug conjugates such as esters and amides, metabolites, hydrates, solvates and the like.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In some embodiments, the subject is a human.

As used herein, the term "ADP-mediated disease or condition" and the like refers to a disease or condition characterized by less than or greater than normal, ADP activity. A ADP-mediated disease or condition is one in which modulation of ADP results in some effect on the underlying condition or disease (e.g., a ADP inhibitor or antagonist results in some improvement in patient well-being in at least some patients).

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include, but are not limited to methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group is one having one or more double bonds directly attached to carbon radicals. Similarly, the term "alkynyl" refers to an unsaturated alkyl group having one or more triple bonds. Examples of such unsaturated alkyl groups include, but are not limited to vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. When "cycloalkyl" is used in combination with "alkyl", as in $C_{3-5}$ cycloalkyl-alkyl, the cycloalkyl portion is meant to have from three to five carbon atoms, while the alkyl portion is an alkylene moiety having from one to three carbon atoms (e.g., —$CH_2$—, —$CH_2CH_2$— or —$CH_2CH_2CH_2$—).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. For brevity, the term $C_{1-6}$alkylamino is meant to include straight chain, branched or cyclic alkyl groups or combinations thereof, such as methyl, ethyl, 2-methylpropyl, cyclobutyl and cyclopropylmethyl.

The terms "arylalkyl", "arylalkenyl" and "aryloxyalkyl" refer to an aryl radical attached directly to an alkyl group, an alkenyl group, or an oxygen which is attached to an alkyl group, respectively. For brevity, aryl as part of a combined term as above, is meant to include heteroaryl as well.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The terms "cycloalkyl" and "cycloalkenyl" refer to a saturated hydrocarbon ring and includes bicyclic and polycyclic rings. Similarly, cycloalkyl and cycloalkenyl groups having a heteroatom (e.g. N, O, S or Si) in place of a carbon ring atom may be referred to as "heterocycloalkyl", "heterocyclyl" and "heterocycloalkylene," respectively. Accordingly, the term "heterocyclyl" includes heteroaryl groups or rings. Examples of cycloalkyl and heterocyclyl groups are, for example, cyclohexyl, norbornyl, adamantyl, morpholinyl, thiomorpholinyl, dioxothiomorpholinyl, pyridinyl, oxadiazolyl, thiadiazolyl, tetrazolyl, thiazoyl and the like. The cycloalkyl and heterocyclyl moieties may also be optionally substituted with halogen atoms, or other groups such as nitro, alkyl, alkylamino, carboxyl, alkoxy, aryloxy and the like. In some embodiments, cycloalkyl and cycloalkenyl moieties are those having 3 to 12 carbon atoms in the ring (e.g., cyclohexyl, cyclooctyl, norbornyl, adamantyl, and the like). In some embodiments, heterocycloalkyl and heterocycloalkylene moieties are those having 1 to 3 hetero atoms in the ring (e.g., morpholinyl, thiomorpholinyl, dioxothiomorpholinyl, piperidinyl and the like). Additionally, the term "(cycloalkyl) alkyl" refers to a group having a cycloalkyl moiety attached to an alkyl moiety. Examples are cyclohexylmethyl, cyclohexylethyl and cyclopentylpropyl.

As used herein, the term "heteroatom" is meant to include oxygen (O), nitrogen (N), sulfur (S) and silicon (Si).

The term "aryl" means, unless otherwise stated, a polyunsaturated, typically aromatic, hydrocarbon group which can be a single ring or multiple rings (up to three rings) which are fused together or linked covalently. Exemplary aryl groups are phenyl (or benzene), naphthyl, biphenyl and the like. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl (or 2-thiophenyl), 3-thienyl (or 3-thiophenyl), 2-pyridyl, 3-pyridyl, 4-pyridyl, 2-pyrazyl, 4-pyrazyl, 2-pyrimidyl, 4-pyrimidyl, 4-tetrazoyl, 5-tetrazoyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

The term "substituted" refers to the replacement of an atom or a group of atoms of a compound with another atom or group of atoms. For example, an atom or a group of atoms may be substituted with one or more of the following substituents or groups: halo, nitro, $C_1$-$C_8$alkyl, $C_1$-$C_8$alkylamino, hydroxy$C_1$-$C_8$alkyl, halo $C_1$-$C_8$alkyl, carboxyl, hydroxyl, $C_1$-$C_8$alkoxy, $C_1$-$C_8$alkoxy $C_1$-$C_8$alkoxy, halo$C_1$-$C_8$alkoxy, thio $C_1$-$C_8$alkyl, aryl, aryloxy, $C_3$-$C_8$cycloalkyl, $C_3$-$C_8$cycloalkyl$C_1$-$C_8$alkyl, aryl, heteroaryl, aryl$C_1$-$C_8$alkyl, heteroaryl$C_1$-$C_8$alkyl, $C_2$-$C_8$alkenyl containing 1 to 2 double bonds, $C_2$-$C_8$alkynyl containing 1 to 2 triple bonds, $C_2$-$C_8$alk(en)(yn)yl groups, cyano, formyl, oxo, thio, $C_1$-$C_8$alkylcarbonyl, arylcarbonyl heteroarylcarbonyl, carboxy, $C_1$-$C_8$alkoxycarbonyl, aryloxycarbonyl, aminocarbonyl, $C_1$-$C_8$alkylaminocarbonyl, $C_1$-$C_8$dialkylaminocarbonyl, arylaminocarbonyl, diarylaminocarbonyl, aryl$C_1$-$C_8$alkylaminocarbonyl, aryloxy, halo$C_1$-$C_8$alkoxy, $C_2$-$C_8$alkenyloxy, $C_2$-$C_8$alkynyloxy, aryl$C_1$-$C_8$alkoxy, amino$C_1$-$C_8$alkyl, $C_1$-$C_8$alkylamino$C_1$-$C_8$alkyl, $C_1$-$C_8$dialkylamino$C_1$-$C_8$alkyl, arylamino$C_1$-$C_8$alkyl, amino, $C_1$-$C_8$dialkylamino, arylamino, $C_1$-$C_8$alkylarylamino, $C_1$-$C_8$alkylcarbonylamino, arylcarbonylamino, azido, mercapto, $C_1$-$C_8$alkylthio, arylthio, halo$C_1$-$C_8$alkylthio, thiocyano, isothiocyano, $C_1$-$C_8$alkylsulfinyl, $C_1$-$C_8$alkylsulfonyl, arylsulfinyl, arylsulfonyl, aminosulfonyl, $C_1$-$C_8$alkylaminosulfonyl, $C_1$-$C_8$dialkylaminosulfonyl and arylaminosulfonyl. When the term "substituted" appears prior to a list of possible substituted groups, it is intended that the term apply to every member of that group.

The term "unsubstituted" refers to a native compound that lacks replacement of an atom or a group of atoms.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic ammonium, zinc or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical*

Science, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an in vitro environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (chiral centers) or double bonds; the racemates, diastereomers, geometric isomers and individual isomers (e.g., separate enantiomers) are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium (3H), iodine-125 ($^{125}$I), phosphorous-32 ($^{32}$P) or carbon-14 ($^{14}$C). All isotopic variations of the compounds of the present invention, whether radioactive or not, are intended to be encompassed within the scope of the present invention.

General

DESCRIPTION OF THE EMBODIMENTS

Compounds

In view of the above, the present invention provides, in one aspect, compounds having the formula:

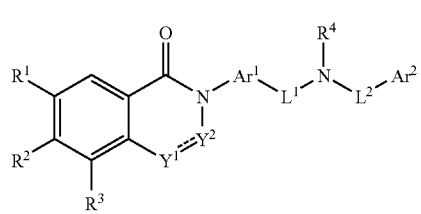

(I)

and pharmaceutically acceptable salts thereof.

The symbol $Y^1$ represents a member selected from the group consisting of N, NH, O, $CR^5$ and $CH_2$.

The symbol $Y^2$ is selected from the group consisting of CO, $CH_2$, CH and N.

Each symbol $R^1$, $R^2$ and $R^3$ is independently selected from the group consisting of H, $C_{1-6}$alkyl, $C_{2-6}$ alkenyl, $C_{2-6}$ alkynyl, $-NR^7{}_2$, $C_{1-6}$alkoxy, halogen, $C_{1-6}$haloalkyl, hydroxy$C_{1-6}$alkyl, cyano, $-C(O)R^6$, $C_{3-6}$cycloalkyl, $C_{3-6}$cycloalkyl-$C_{1-6}$alkyl, aryl and aryl$C_{1-6}$alkyl, wherein each of said $C_{1-6}$alkyl, $C_{2-6}$ alkenyl, $C_{2-6}$ alkynyl and aryl portions is optionally substituted with from 1 to 3 substituents, each independently selected from the group consisting of $C_{1-6}$ alkyl, $C_{2-6}$ alkenyl, $C_{2-6}$ alkynyl, amino, $C_{1-6}$alkoxy, halogen, hydroxyl, cyano, oxo, thio, $C_{3-6}$cycloalkyl, aryl and heteroaryl.

The symbol $R^4$ is H or $-(CH_2)_m CO_2 H$.

The symbol $R^5$ is selected from H, $C_{1-6}$alkyl, cyano, halogen, halo$C_{1-6}$alkyl, aryl, aryl$C_{1-6}$alkyl and $-C(O)R^6$.

The symbol $R^6$ is selected from the group consisting of H, hydroxy, $C_{1-6}$alkyl, $C_{1-6}$alkoxy, heterocyclyl$C_{1-6}$alkoxy and $-NR^7{}_2$.

Each symbol $R^7$ is independently selected from the group consisting of H, $C_{1-6}$alkyl and aryl$C_{1-6}$alkyl or optionally, two $R^7$ groups attached to nitrogen are combined with the nitrogen atom to form an azetidine, pyrrolidine, piperidine or morpholine ring; wherein each of said $C_{1-6}$ alkyl and aryl$C_{1-6}$ alkyl is optionally substituted with from 1 to 3 substituents, each independently selected from the group consisting of halogen, amino, hydroxyl, $C_{1-6}$ alkoxy, cyano, $C_{1-6}$ alkyl, $C_{3-6}$ cycloalkyl, aryl, and heteroaryl.

Each symbol $Ar^1$ and $Ar^2$ represents an aromatic ring selected from the group consisting of benzene, pyridine, pyrazine, pyrimidine, tetrazole and thiophene, each of which is optionally substituted with from 1-2$R^8$ substituents.

Each symbol $R^8$ independently represents a member selected from the group consisting of halogen, cyano, hydroxy, $C_{1-6}$alkyl, $C_{2-6}$alkenyl, $C_{2-6}$alkynyl, $C_{1-6}$alkoxy, halo$C_{1-6}$alkyl, halo$C_{1-6}$alkoxy, $C_{3-5}$cycloalkyl-$C_{1-6}$alkoxy, $-NR^7$, $-C(=NR^{8a})-N(R^{8b})_2$, $-C(O)R^{8a}$, $-O(CH_2)_m OR^{8b}$, $-(CH_2)_m OR^{8b}$, $-O(CH_2)_m N(R^{8b})_2$ and $-(CH_2)_m N(R^{8b})_2$.

Each symbol $R^{8a}$ represents a member independently selected from the group consisting of H, hydroxy, $C_{1-6}$alkyl, $C_{1-6}$alkoxy and $-NR^7$.

Each symbol $R^{8b}$ represents a member independently selected from the group consisting of H, $C_{1-4}$ alkyl and $C_{1-4}$alkanoyl, and optionally, two $R^{8b}$ groups attached to nitrogen are combined with the nitrogen atom to form an azetidine, pyrrolidine, piperidine or morpholine ring; wherein each of said $C_{1-4}$ alkyl and $C_{1-4}$ alkanoyl is optionally substituted with from 1 to 3 substituents, each independently selected from the group consisting of halogen, amino, hydroxyl, $C_{1-6}$ alkoxy, cyano, $C_{1-6}$ alkyl, $C_{3-6}$ cycloalkyl, aryl, and heteroaryl.

The symbol $L^1$ represents a linking group selected from the group consisting of a bond, $-CO-$, $-CH_2-$, $-NHCO-$ and $-CH_2CO-$.

The symbol $L^2$ is a linking group selected from the group consisting of a bond, $-CR^9{}_2-$, $-CR^9{}_2 CH_2-$ and $-CO-$.

Each symbol $R^9$ represents a member independently selected from the group consisting of H, $C_{1-6}$alkyl, hydroxyalkyl, $-(CH_2)_m C(O)R^6$, $-C(O)R^6$ and heterocyclyl substituted with from 0 to 2 substituents selected from the group halogen, cyano, $C_{1-6}$alkyl, $C_{2-6}$alkenyl, $C_{2-6}$alkynyl, $C_{1-6}$alkoxy, halo$C_{1-6}$alkyl, oxo and thio.

Each subscript m is independently 1, 2 or 3.

In one group of embodiments, $Y^1$ is NH and $Y^2$ is CO. In one group of embodiments, $Y^1$ is O and $Y^2$ is $CH_2$. In one group of embodiments, $Y^1$ is CH and $Y^2$ is CH. In one group of embodiments, $Y^1$ is N and $Y^2$ is CH. In one group of embodiments, $Y^1$ is CH and $Y^2$ is N. In one group of embodiments, $Y^1$ and $Y^2$ are $CH_2$ In another group of embodiments, each $Ar^1$ and $Ar^2$ are independently benzene, thiophene or tetrazole. In one group of embodiments, $Ar^1$ is benzene. In one group of embodiments, $Ar^1$ is thiophene. In one group of embodiments, $Ar^2$ is tetrazole. In one group of embodiments, $Ar^2$ is benzene. In one group of embodiments, $Ar^2$ is thiophene. In any of the embodiments herein, each of the groups comprising $Ar^1$ and $Ar^2$ is optionally substituted with from 1-2$R^8$ substituents In one group of embodiments, $L^1$ is a bond. In one group of embodiments, wherein $L^1$ is —CO—. In one group of embodiments, $L^1$ is —$CH_2$—. In one group of embodiments, $L^1$ is —NHCO—. In one group of embodiments, $L^1$ is —$CH_2CO$—. In one group of embodiments, $L^2$ is a bond. In one group of embodiments, $L^2$ is —$CR^9_2$—. In one group of embodiments, $L^2$ is —$CR^9_2CH_2$—. In one group of embodiments, $L^2$ is —CO—.

In another group of embodiments, at least one $R^9$ is H. In one group of embodiments, at least one $R^9$ is —C(O)$R^6$. In one group of embodiments, at least one $R^9$ is —$(CH_2)_mC(O)R^6$. In one group of embodiments, at least one $R^9$ is heterocyclyl. In one group of embodiments, at least one $R^9$ is independently selected from the group consisting of:

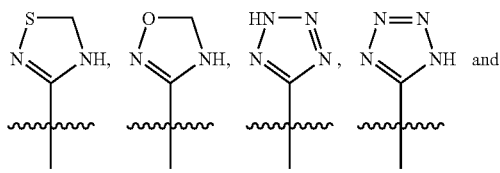

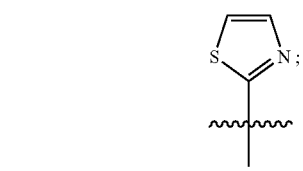

each of which is substituted with from 0 to 2 substituents selected from the group halogen, cyano, $C_{1-6}$alkyl, $C_{2-6}$alkenyl, $C_{2-6}$ alkynyl, $C_{1-6}$alkoxy, halo$C_{1-6}$alkyl, oxo and thio; and wherein the wavy line indicates the point of attachment to the rest of the molecule. In one group of embodiments, at least one $R^9$ is independently selected from the group consisting of:

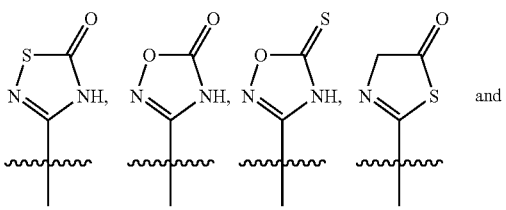

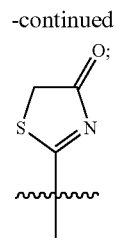

wherein the wavy line indicates the point of attachment to the rest of the molecule.

In another group of embodiments, the compound has the formula:

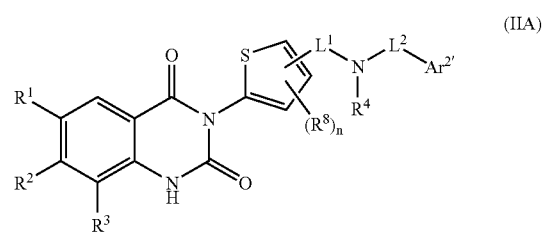

wherein the subscript n is an integer of from 0 to 2.

In another group of embodiments, the compound has the formula:

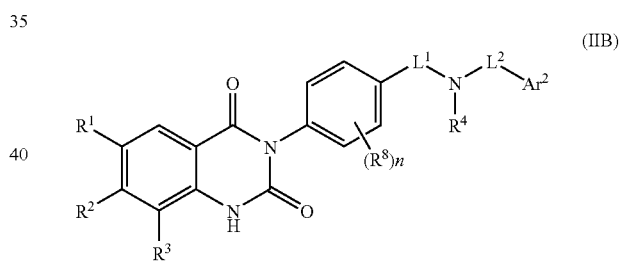

wherein the subscript n is an integer of from 0 to 2.

In another group of embodiments, the compound has the formula:

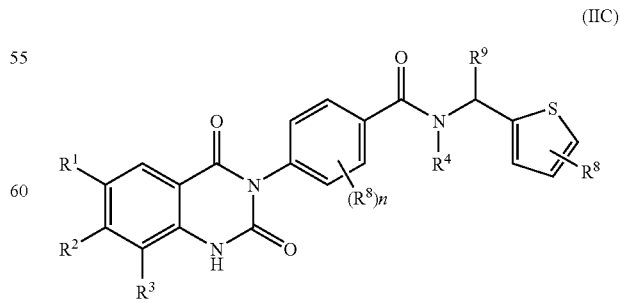

wherein the subscript n is an integer of from 0 to 2.

In another group of embodiments, the compound has the formula:

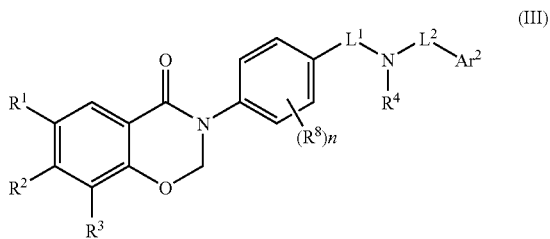

(III)

wherein the subscript n is an integer of from 0 to 2.

In another group of embodiments, the compound has the formula:

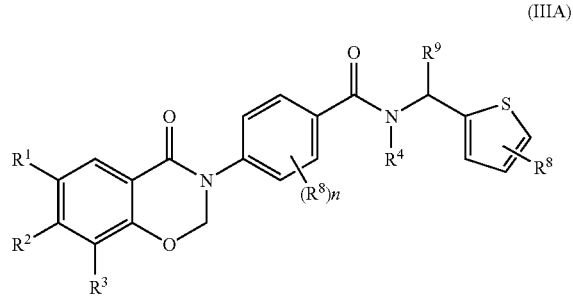

(IIIA)

wherein the subscript n is an integer of from 0 to 2.

In another group of embodiments, the compound has the formula:

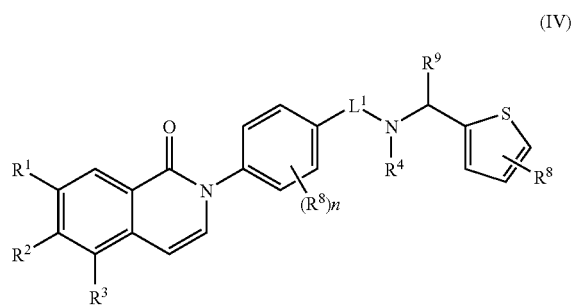

(IV)

wherein the subscript n is an integer of from 0 to 2.

In another group of embodiments, the compound has the formula:

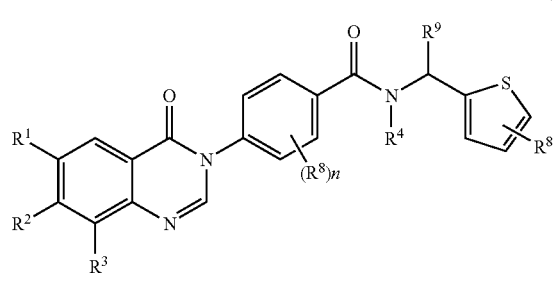

(V)

wherein the subscript n is an integer of from 0 to 2.

In another group of embodiments, the compound has the formula:

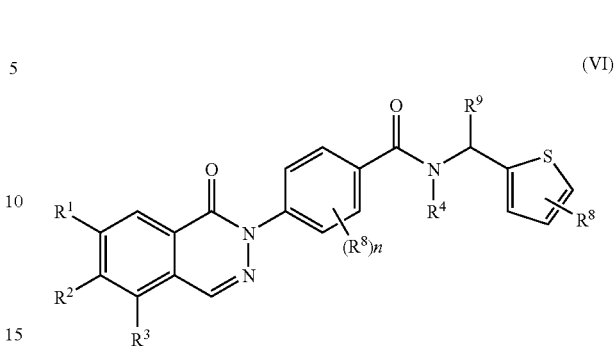

(VI)

wherein the subscript n is an integer of from 0 to 2.

In another group of embodiments, the compound has the formula:

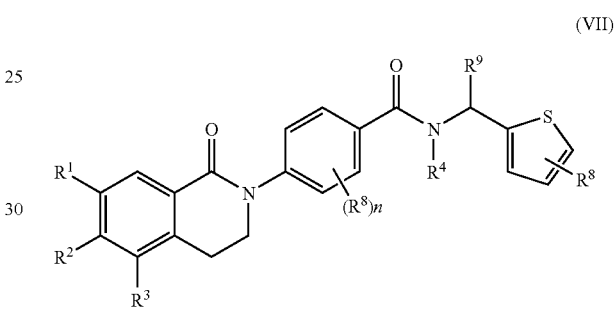

(VII)

wherein the subscript n is an integer of from 0 to 2.

In another group of embodiments, $R^1$ is H, $NHR^7$ or halogen; $R^2$ is H, $C_{1-6}$alkyl, $NHR^7$ or halogen; $R^3$ is H; $R^7$ is $C_{1-6}$alkyl or aryl$C_{1-6}$alkyl; $R^8$ is halogen or alkoxy; and n is 1. In one group of embodiments, $R^1$ is F; $R^2$ is $NHR^7$ and $R^7$ is $CH_3$ or 4-fluorobenzyl.

Still other compounds of the present invention are:

N-((5-chlorothiophen-2-yl)methyl)-4-(7-(4-fluorobenzylamino)-2,4-dioxo-1,2-dihydroquinazolin-3(4H)-yl)benzamide;

2-(4-(7-(4-fluorobenzylamino)-2,4-dioxo-1,2-dihydroquinazolin-3(4H)-yl)benzamido)-2-(thiophen-2-yl)acetic acid;

2-(4-(7-(4-fluorobenzylamino)-2,4-dioxo-1,2-dihydroquinazolin-3(4H)-yl)benzamido)-3-(thiophen-2-yl)propanoic acid;

N-((5-chlorothiophen-2-yl)methyl)-4-(6-fluoro-7-(methylamino)-2,4-dioxo-1,2-dihydroquinazolin-3(4H)-yl)benzamide;

2-(5-chlorothiophen-2-yl)-2-(4-(6-fluoro-7-(methylamino)-2,4-dioxo-1,2-dihydroquinazolin-3(4H)-yl)benzamido)acetic acid;

2-(N-((5-chlorothiophen-2-yl)methyl)-4-(6-fluoro-7-(methylamino)-2,4-dioxo-1,2-dihydroquinazolin-3(4H)-yl)benzamido)acetic acid;

N-((5-chlorothiophen-2-yl)(1H-tetrazol-5-yl)methyl)-4-(6-fluoro-7-(methylamino)-2,4-dioxo-1,2-dihydroquinazolin-3(4H)-yl)benzamide;

2-(4-(6-fluoro-7-(methylamino)-2,4-dioxo-1,2-dihydroquinazolin-3(4H)-yl)benzamido)-2-(thiophen-2-yl)acetic acid;

2-(4-(6-fluoro-7-(methylamino)-2,4-dioxo-1,2-dihydro-quinazolin-3(4H)-yl)benzamido)-3-(thiophen-2-yl)propanoic acid;

N-((1H-tetrazol-5-yl)methyl)-4-(7-(4-fluorobenzylamino)-2,4-dioxo-1,2-dihydroquinazolin-3(4H)-yl)benzamide;

N-((3-chlorophenyl)(1H-tetrazol-5-yl)methyl)-4-(6-fluoro-7-(methylamino)-2,4-dioxo-1,2-dihydroquinazolin-3(4H)-yl)benzamide;

N-((4-chlorophenyl)(1H-tetrazol-5-yl)methyl)-4-(6-fluoro-7-(methylamino)-2,4-dioxo-1,2-dihydroquinazolin-3(4H)-yl)benzamide;

2-(5-chlorothiophen-2-yl)-2-(4-(6-fluoro-7-(methylamino)-2,4-dioxo-1,2-dihydroquinazolin-3(4H)-yl)benzamido)acetic acid;

2-(4-chlorophenyl)-2-(4-(6-fluoro-7-(methylamino)-2,4-dioxo-1,2-dihydroquinazolin-3(4H)-yl)benzamido)acetic acid;

2-(3-chlorophenyl)-2-(4-(6-fluoro-7-(methylamino)-2,4-dioxo-1,2-dihydroquinazolin-3(4H)-yl)benzamido)acetic acid;

4-(6-fluoro-7-(methylamino)-4-oxo-2H-benzo[e][1,3]oxazin-3(4H)-yl)-N-((5-methylthiophen-2-yl)(1H-tetrazol-5-yl)methyl)benzamide;

methyl 2-(5-chlorothiophen-2-yl)-2-(4-(6-fluoro-7-(methylamino)-4-oxo-2H-benzo[e][1,3]oxazin-3(4H)-yl)benzamido)acetate;

2-(4-(6-fluoro-7-(methylamino)-2,4-dioxo-1,2-dihydroquinazolin-3(4H)-yl)benzamido)-2-(5-methylthiophen-2-yl)acetic acid;

2-(5-chlorothiophen-2-yl)-2-(4-(7-(methylamino)-2,4-dioxo-1,2-dihydroquinazolin-3(4H)-yl)benzamido)acetic acid;

N-((5-chlorothiophen-2-yl)(5-oxo-4,5-dihydro-1,2,4-oxadiazol-3-yl)methyl)-4-(6-fluoro-7-(methylamino)-2,4-dioxo-1,2-dihydroquinazolin-3(4H)-yl)benzamide;

N-((1H-tetrazol-5-yl)(m-tolyl)methyl)-4-(6-fluoro-7-(methylamino)-2,4-dioxo-1,2-dihydroquinazolin-3(4H)-yl)benzamide;

4-(6-fluoro-7-(methylamino)-2,4-dioxo-1,2-dihydroquinazolin-3(4H)-yl)-N-((3-methoxyphenyl)(1H-tetrazol-5-yl)methyl)benzamide;

4-(6-fluoro-7-(methylamino)-2,4-dioxo-1,2-dihydroquinazolin-3(4H)-yl)-N-((3-fluorophenyl)(1H-tetrazol-5-yl)methyl)benzamide;

N-((5-chlorothiophen-2-yl)(5-oxo-4,5-dihydro-1,2,4-thiadiazol-3-yl)methyl)-4-(6-fluoro-7-(methylamino)-2,4-dioxo-1,2-dihydroquinazolin-3(4H)-yl)benzamide;

ethyl 2-(5-chlorothiophen-2-yl)-2-(4-(6-fluoro-7-(methylamino)-2,4-dioxo-1,2-dihydroquinazolin-3(4H)-yl)benzamido)acetate;

3-(5-chlorothiophen-2-yl)-3-(4-(6-fluoro-7-(methylamino)-2,4-dioxo-1,2-dihydroquinazolin-3(4H)-yl)benzamido)propanoic acid;

N-((2-chlorophenyl)(1H-tetrazol-5-yl)methyl)-4-(6-fluoro-7-(methylamino)-2,4-dioxo-1,2-dihydroquinazolin-3(4H)-yl)benzamide;

N-((3,4-dichlorophenyl)(1H-tetrazol-5-yl)methyl)-4-(6-fluoro-7-(methylamino)-2,4-dioxo-1,2-dihydroquinazolin-3(4H)-yl)benzamide;

N-((3,5-dichlorophenyl)(1H-tetrazol-5-yl)methyl)-4-(6-fluoro-7-(methylamino)-2,4-dioxo-1,2-dihydroquinazolin-3(4H)-yl)benzamide;

N-((1H-tetrazol-5-yl)(3-(trifluoromethoxy)phenyl)methyl)-4-(6-fluoro-7-(methylamino)-2,4-dioxo-1,2-dihydroquinazolin-3(4H)-yl)benzamide;

N-((5-chlorothiophen-2-yl)(5-thioxo-4,5-dihydro-1,2,4-oxadiazol-3-yl)methyl)-4-(6-fluoro-7-(methylamino)-2,4-dioxo-1,2-dihydroquinazolin-3(4H)-yl)benzamide;

2-(5-chlorothiophen-2-yl)-2-(4-(2,4-dioxo-1,2-dihydro-quinazolin-3(4H)-yl)benzamido)acetic acid;

N-((1H-tetrazol-5-yl)(3-(trifluoromethyl)phenyl)methyl)-4-(6-fluoro-7-(methylamino)-2,4-dioxo-1,2-dihydroquinazolin-3(4H)-yl)benzamide;

2-morpholinoethyl 2-(5-chlorothiophen-2-yl)-2-(4-(6-fluoro-7-(methylamino)-2,4-dioxo-1,2-dihydroquinazolin-3(4H)-yl)benzamido)acetate;

N-(1-(5-chlorothiophen-2-yl)-2-hydroxyethyl)-4-(6-fluoro-7-(methylamino)-2,4-dioxo-1,2-dihydroquinazolin-3(4H)-yl)benzamide;

2-(5-chlorothiophen-2-yl)-2-(4-(6-iodo-2,4-dioxo-1,2-dihydroquinazolin-3(4H)-yl)benzamido)acetic acid;

2-(5-chlorothiophen-2-yl)-2-(4-(6-isopropoxy-2,4-dioxo-1,2-dihydroquinazolin-3(4H)-yl)benzamido)acetic acid;

2-(5-chlorothiophen-2-yl)-2-(4-(2,4-dioxo-1,2-dihydro-quinazolin-3(4H)-yl)benzamido)acetic acid;

3-(N-((5-chlorothiophen-2-yl)methyl)-4-(6-fluoro-7-(methylamino)-2,4-dioxo-1,2-dihydroquinazolin-3(4H)-yl)benzamido)propanoic acid;

2-(5-chlorothiophen-2-yl)-2-(4-(6-fluoro-7-(methylamino)-2,4-dioxo-1,2-dihydroquinazolin-3(4H)-yl)-2-methylbenzamido)acetic acid;

2-(5-chlorothiophen-2-yl)-2-(4-(6-fluoro-7-(methylamino)-2,4-dioxo-1,2-dihydroquinazolin-3(4H)-yl)-2-methoxybenzamido)acetic acid;

2-(2-chloro-4-(6-fluoro-7-(methylamino)-2,4-dioxo-1,2-dihydroquinazolin-3(4H)-yl)benzamido)-2-(5-chlorothiophen-2-yl)acetic acid;

2-(5-chlorothiophen-2-yl)-2-(2-fluoro-4-(6-fluoro-7-(methylamino)-2,4-dioxo-1,2-dihydroquinazolin-3(4H)-yl)benzamido)acetic acid;

(S)-N-((5-chlorothiophen-2-yl)(5-oxo-4,5-dihydro-1,2,4-oxadiazol-3-yl)methyl)-4-(6-fluoro-7-(methylamino)-2,4-dioxo-1,2-dihydroquinazolin-3(4H)-yl)benzamide;

(R)-N-((5-chlorothiophen-2-yl)(5-oxo-4,5-dihydro-1,2,4-oxadiazol-3-yl)methyl)-4-(6-fluoro-7-(methylamino)-2,4-dioxo-1,2-dihydroquinazolin-3(4H)-yl)benzamide;

N-(2-amino-1-(5-chlorothiophen-2-yl)-2-oxoethyl)-4-(6-fluoro-7-(methylamino)-2,4-dioxo-1,2-dihydroquinazolin-3(4H)-yl)benzamide;

2-(5-chlorothiophen-2-yl)-2-(4-(7-fluoro-6-(methylamino)-2,4-dioxo-1,2-dihydroquinazolin-3(4H)-yl)benzamido)acetic acid;

N-((5-chlorothiophen-2-yl)(1H-tetrazol-5-yl)methyl)-4-(7-fluoro-6-(methylamino)-2,4-dioxo-1,2-dihydroquinazolin-3(4H)-yl)benzamide;

N-((5-chlorothiophen-2-yl)(5-oxo-4,5-dihydro-1,2,4-oxadiazol-3-yl)methyl)-4-(7-fluoro-6-(methylamino)-2,4-dioxo-1,2-dihydroquinazolin-3(4H)-yl)benzamide;

2-(5-chlorothiophen-2-yl)-2-(4-(6-fluoro-7-(methylamino)-2,4-dioxo-1,2-dihydroquinazolin-3(4H)-yl)-3-methoxybenzamido)acetic acid;

N-((5-chlorothiophen-2-yl)(1H-tetrazol-5-yl)methyl)-4-(6-fluoro-7-(methylamino)-2,4-dioxo-1,2-dihydroquinazolin-3(4H)-yl)-3-methoxybenzamide;

N-((5-chlorothiophen-2-yl)(5-oxo-4,5-dihydro-1,2,4-oxadiazol-3-yl)methyl)-4-(6-fluoro-7-(methylamino)-2,4-dioxo-1,2-dihydroquinazolin-3(4H)-yl)-3-methoxybenzamide;

N-((5-chlorothiophen-2-yl)(1H-tetrazol-5-yl)methyl)-4-(6-fluoro-7-(methylamino)-4-oxo-2H-benzo[e][1,3]oxazin-3(4H)-yl)benzamide;

2-(N-((5-chlorothiophen-2-yl)methyl)-4-(6-fluoro-7-(methylamino)-4-oxo-2H-benzo[e][1,3]oxazin-3(4H)-yl)benzamido)acetic acid;
2-(5-chlorothiophen-2-yl)-2-(4-(6-fluoro-7-(methylamino)-4-oxo-2H-benzo[e][1,3]oxazin-3(4H)-yl)benzamido)acetic acid;
3-(5-chlorothiophen-2-yl)-2-(4-(6-fluoro-7-(methylamino)-4-oxo-2H-benzo[e][1,3]oxazin-3(4H)-yl)benzamido)propanoic acid;
2-(4-(6-fluoro-7-(methylamino)-4-oxo-2H-benzo[e][1,3]oxazin-3(4H)-yl)benzamido)-2-phenylacetic acid;
2-(5-chlorothiophen-2-yl)-2-(2-(4-(6-fluoro-7-(methylamino)-4-oxo-2H-benzo[e][1,3]oxazin-3(4H)-yl)phenyl)acetamido)-N,N-dimethylacetamide;
N-(1-(5-chlorothiophen-2-yl)-2-oxo-2-(pyrrolidin-1-yl)ethyl)-2-(4-(6-fluoro-7-(methylamino)-4-oxo-2H-benzo[e][1,3]oxazin-3(4H)-yl)phenyl)acetamide;
N-(2-amino-1-(5-chlorothiophen-2-yl)-2-oxoethyl)-2-(4-(6-fluoro-7-(methylamino)-4-oxo-2H-benzo[e][1,3]oxazin-3(4H)-yl)phenyl)acetamide;
(R)-2-(4-(6-fluoro-7-(methylamino)-4-oxo-2H-benzo[e][1,3]oxazin-3(4H)-yl)benzamido)-3-phenylpropanoic acid;
(S)-2-(4-(6-fluoro-7-(methylamino)-4-oxo-2H-benzo[e][1,3]oxazin-3(4H)-yl)benzamido)-3-phenylpropanoic acid;
4-(6-fluoro-7-(methylamino)-4-oxo-2H-benzo[e][1,3]oxazin-3(4H)-yl)-N-((5-methylthiophen-2-yl)(1H-tetrazol-5-yl)methyl)benzamide;
(S)-2-(5-chlorothiophen-2-yl)-2-(4-(6-fluoro-7-(methylamino)-4-oxo-2H-benzo[e][1,3]oxazin-3(4H)-yl)benzamido)acetic acid
2-(4-(6-fluoro-7-(methylamino)-4-oxo-2H-benzo[e][1,3]oxazin-3(4H)-yl)benzamido)-2-(thiophen-2-yl)acetic acid;
2-(4-(6-fluoro-7-(methylamino)-4-oxo-2H-benzo[e][1,3]oxazin-3(4H)-yl)benzamido)-3-(thiophen-2-yl)propanoic acid;
(S)-2-(4-(6-fluoro-7-(methylamino)-4-oxo-2H-benzo[e][1,3]oxazin-3(4H)-yl)benzamido)-2-phenylacetic acid;
methyl 2-(5-chlorothiophen-2-yl)-2-(4-(6-fluoro-7-(methylamino)-4-oxo-2H-benzo[e][1,3]oxazin-3(4H)-yl)benzamido)acetate;
ethyl 2-(5-chlorothiophen-2-yl)-2-(4-(6-fluoro-7-(methylamino)-4-oxo-2H-benzo[e][1,3]oxazin-3(4H)-yl)benzamido)acetate;
2-(5-chlorothiophen-2-yl)-2-(4-(8-methoxy-4-oxo-2H-benzo[e][1,3]oxazin-3(4H)-yl)benzamido)acetic acid;
2-(5-chlorothiophen-2-yl)-2-(4-(7-methyl-4-oxo-2H-benzo[e][1,3]oxazin-3(4H)-yl)benzamido)acetic acid;
N-(2-amino-1-(5-chlorothiophen-2-yl)-2-oxoethyl)-4-(6-fluoro-7-(methylamino)-4-oxo-2H-benzo[e][1,3]oxazin-3(4H)-yl)benzamide;
N-((5-chlorothiophen-2-yl)(5-oxo-4,5-dihydro-1,2,4-oxadiazol-3-yl)methyl)-4-(6-fluoro-7-(methylamino)-4-oxo-2H-benzo[e][1,3]oxazin-3(4H)-yl)benzamide;
2-(5-chlorothiophen-2-yl)-2-(4-(6-ethyl-4-oxo-2H-benzo[e][1,3]oxazin-3(4H)-yl)benzamido)acetic acid;
N-((5-chlorothiophen-2-yl)(1-methyl-H-tetrazol-5-yl)methyl)-4-(6-fluoro-7-(methylamino)-4-oxo-2H-benzo[e][1,3]oxazin-3(4H)-yl)benzamide;
N-((5-chlorothiophen-2-yl)(2-methyl-2H-tetrazol-5-yl)methyl)-4-(6-fluoro-7-(methylamino)-4-oxo-2H-benzo[e][1,3]oxazin-3(4H)-yl)benzamide;
N-((5-chlorothiophen-2-yl)(5-thioxo-4,5-dihydro-1,2,4-oxadiazol-3-yl)methyl)-4-(6-fluoro-7-(methylamino)-4-oxo-2H-benzo[e][1,3]oxazin-3(4H)-yl)benzamide;
methyl 2-(5-chlorothiophen-2-yl)-2-(4-(6-methyl-4-oxo-2H-benzo[e][1,3]oxazin-3(4H)-yl)benzamido)acetate;
2-(5-chlorothiophen-2-yl)-2-(4-(6-methyl-4-oxo-2H-benzo[e][1,3]oxazin-3(4H)-yl)benzamido)acetic acid;
2-(5-chlorothiophen-2-yl)-2-(4-(7-ethyl-4-oxo-2H-benzo[e][1,3]oxazin-3(4H)-yl)benzamido)acetic acid;
3-(5-chlorothiophen-2-yl)-3-(4-(6-fluoro-7-(methylamino)-4-oxo-2H-benzo[e][1,3]oxazin-3(4H)-yl)benzamido)propanoic acid;
N-((3-chlorophenyl)(1H-tetrazol-5-yl)methyl)-4-(6-fluoro-7-(methylamino)-4-oxo-2H-benzo[e][1,3]oxazin-3(4H)-yl)benzamide;
2-(3-chlorophenyl)-2-(4-(6-fluoro-7-(methylamino)-4-oxo-2H-benzo[e][1,3]oxazin-3(4H)-yl)benzamido)acetic acid;
N-((5-chlorothiophen-2-yl)(thiazol-2-yl)methyl)-4-(6-fluoro-7-(methylamino)-4-oxo-2H-benzo[e][1,3]oxazin-3(4H)-yl)benzamide;
2-(5-chlorothiophen-2-yl)-2-(4-(4-oxo-2H-benzo[e][1,3]oxazin-3(4H)-yl)benzamido)acetic acid;
2-(5-chlorothiophen-2-yl)-2-(4-(7-(4-fluorobenzylamino)-4-oxo-2H-benzo[e][1,3]oxazin-3(4H)-yl)benzamido)acetic acid;
N-((5-chlorothiophen-2-yl)(4-methylthiazol-2-yl)methyl)-4-(6-fluoro-7-(methylamino)-4-oxo-2H-benzo[e][1,3]oxazin-3(4H)-yl)benzamide;
3-(N-((5-chlorothiophen-2-yl)methyl)-4-(6-fluoro-7-(methylamino)-4-oxo-2H-benzo[e][1,3]oxazin-3(4H)-yl)benzamido)propanoic acid;
N-((5-chlorothiophen-2-yl)(1H-tetrazol-5-yl)methyl)-4-(6-fluoro-7-(methylamino)-4-oxo-2H-benzo[e][1,3]oxazin-3(4H)-yl)benzamide;
(S)-N-((5-chlorothiophen-2-yl)(5-oxo-4,5-dihydro-1,2,4-oxadiazol-3-yl)methyl)-4-(6-fluoro-7-(methylamino)-4-oxo-2H-benzo[e][1,3]oxazin-3(4H)-yl)benzamide;
(R)-N-((5-chlorothiophen-2-yl)(1H-tetrazol-5-yl)methyl)-4-(6-fluoro-7-(methylamino)-4-oxo-2H-benzo[e][1,3]oxazin-3(4H)-yl)benzamide;
2-(5-chlorothiophen-2-yl)-2-(4-(7-fluoro-6-(methylamino)-1-oxoisoquinolin-2(1H)-yl)benzamido)acetic acid;
N-((5-chlorothiophen-2-yl)(1H-tetrazol-5-yl)methyl)-4-(7-fluoro-6-(methylamino)-1-oxoisoquinolin-2(1H)-yl)benzamide;
2-(5-chlorothiophen-2-yl)-2-(4-(7-fluoro-6-methoxy-1-oxoisoquinolin-2(1H)-yl)benzamido)acetic acid;
2-(5-chlorothiophen-2-yl)-2-(4-(6-ethyl-1-oxoisoquinolin-2(1H)-yl)benzamido)acetic acid;
2-(4-(6-carbamoyl-1-oxoisoquinolin-2(1H)-yl)benzamido)-2-(5-chlorothiophen-2-yl)acetic acid;
2-(5-chlorothiophen-2-yl)-2-(4-(6-cyano-1-oxoisoquinolin-2(1H)-yl)benzamido)acetic acid;
2-(5-chlorothiophen-2-yl)-2-(4-(1-oxoisoquinolin-2(1H)-yl)benzamido)acetic acid;
2-(4-(1-oxoisoquinolin-2(1H)-yl)benzamido)-2-(thiophen-2-yl)acetic acid;
2-(5-chlorothiophen-2-yl)-2-(4-(6-cyano-1-oxoisoquinolin-2(1H)-yl)benzamido)acetic acid;
4-(4-carbamoyl-1-oxoisoquinolin-2(1H)-yl)benzamido)-2-(5-chlorothiophen-2-yl)acetic acid;
2-(5-chlorothiophen-2-yl)-2-(4-(4-cyano-1-oxoisoquinolin-2(1H)-yl)benzamido)acetic acid;
2-(5-chlorothiophen-2-yl)-2-(4-(6-methoxy-1-oxoisoquinolin-2(1H)-yl)benzamido)acetic acid;
2-(4-(4-bromo-1-oxoisoquinolin-2(1H)-yl)benzamido)-2-(5-chlorothiophen-2-yl)acetic acid;
2-(5-chloro-N-(4-(6-fluoro-7-(methylamino)-2,4-dioxo-1,2-dihydroquinazolin-3(4H)-yl)benzyl)thiophene-2-carboxamido)acetic acid;

3-(5-chlorothiophen-2-yl)-3-(4-(6-fluoro-7-(methylamino)-2,4-dioxo-1,2-dihydroquinazolin-3(4H)-yl)benzylamino) propanoic acid;
2-(5-chlorothiophen-2-yl)-2-(4-(6-fluoro-7-(methylamino)-4-oxo-2H-benzo[e][1,3]oxazin-3(4H)-yl)benzylamino) acetic acid;
3-(5-chlorothiophen-2-yl)-3-(4-(6-fluoro-7-(methylamino)-4-oxo-2H-benzo[e][1,3]oxazin-3(4H)-yl)benzylamino) propanoic acid;
1-((5-chlorothiophen-2-yl)methyl)-3-(4-(7-(4-fluorobenzylamino)-2,4-dioxo-1,2-dihydroquinazolin-3(4H)-yl)phenyl)urea;
2-(3-(4-(7-(4-fluorobenzylamino)-2,4-dioxo-1,2-dihydroquinazolin-3(4H)-yl)phenyl)ureido)-2-(thiophen-2-yl) acetic acid;
2-(3-(4-(7-(4-fluorobenzylamino)-2,4-dioxo-1,2-dihydroquinazolin-3(4H)-yl)phenyl)ureido)-3-(thiophen-2-yl) propanoic acid;
2-(5-chlorothiophen-2-yl)-2-(3-(4-(6-fluoro-7-(methylamino)-2,4-dioxo-1,2-dihydroquinazolin-3(4H)-yl)phenyl)ureido)acetic acid;
2-(5-chlorothiophen-2-yl)-2-(3-(6-fluoro-7-(methylamino)-2,4-dioxo-1,2-dihydroquinazolin-3(4H)-yl)benzamido) acetic acid;
2-(5-chlorothiophen-2-yl)-2-(5-(6-fluoro-7-(methylamino)-2,4-dioxo-1,2-dihydroquinazolin-3(4H)-yl)thiophene-2-carboxamido)acetic acid;
2-(5-chlorothiophen-2-yl)-2-(5-(6-fluoro-7-(methylamino)-2,4-dioxo-1,2-dihydroquinazolin-3(4H)-yl)thiophene-3-carboxamido)acetic acid;
2-(5-chlorothiophen-2-yl)-2-(2-(4-(6-fluoro-7-(methylamino)-4-oxo-2H-benzo[e][1,3]oxazin-3(4H)-yl)phenyl) acetamido)acetic acid;
2-(5-chlorothiophen-2-yl)-2-(4-(7-fluoro-6-(methylamino)-1-oxoisoquinolin-2(1H)-yl)benzylamino)acetic acid;
2-(5-chlorothiophen-2-yl)-2-(4-(6-fluoro-7-(methylamino)-4-oxoquinazolin-3(4H)-yl)benzamido)acetic acid;
2-(5-chlorothiophen-2-yl)-2-(4-(7-fluoro-6-(methylamino)-1-oxophthalazin-2(1H)-yl)benzamido)acetic acid;
methyl 2-(5-chlorothiophen-2-yl)-2-(2-(4-(6-fluoro-7-(methylamino)-4-oxo-2H-benzo[e][1,3]oxazin-3(4H)-yl)phenyl)acetamido)acetate;
2-(5-chlorothiophen-2-yl)-2-(4-(6-ethyl-1-oxo-3,4-dihydroisoquinolin-2(1H)-yl)benzamido)acetic acid; and
2-(1-((5-chlorothiophen-2-yl)methyl)-3-(4-(6-fluoro-7-(methylamino)-2,4-dioxo-1,2-dihydroquinazolin-3(4H)-yl)phenyl)-1H-1,2,4-triazol-5-ylthio)acetic acid.

Consistent with the practice of those of skill in the art, unlabeled bonds (e.g., those with an unlabeled terminus) are meant to illustrate methyl ($CH_3$) groups.

General Synthetic Schemes

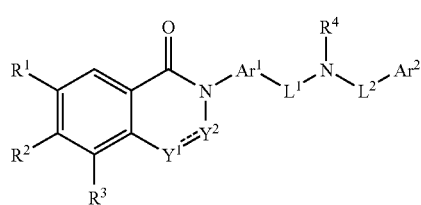

I

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and *Organic Reactions*, Wiley & Sons: New York, 2005, Volumes 1-65. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about –78° C. to about 150° C., more preferably from about 0° C. to about 125° C., and most preferably and conveniently at about room (or ambient) temperature, e.g., about 20° C.

Scheme A describes a method of preparing a compound of formula I wherein $Y^1$ is O and the remaining symbols are as defined hereinbefore.

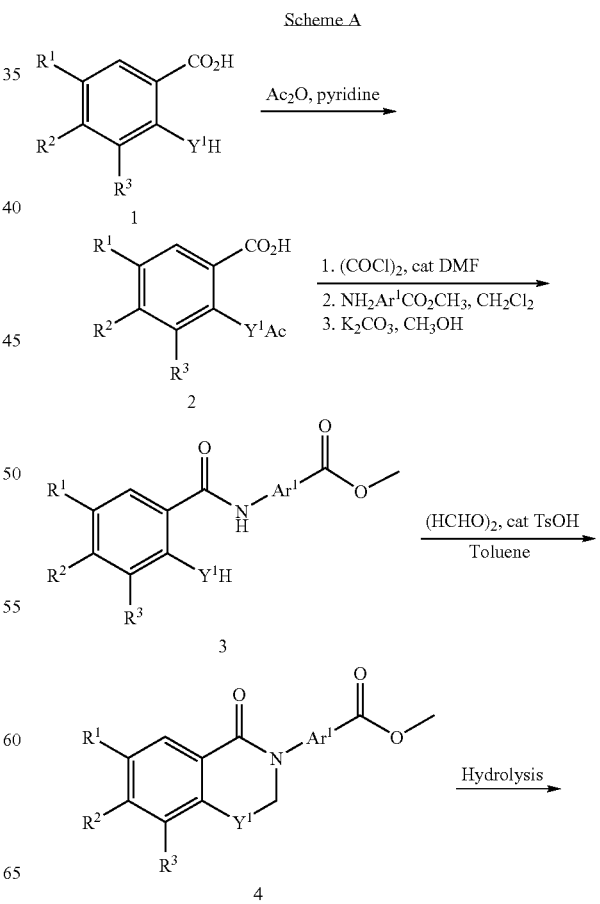

-continued

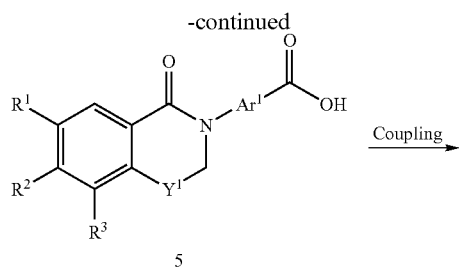

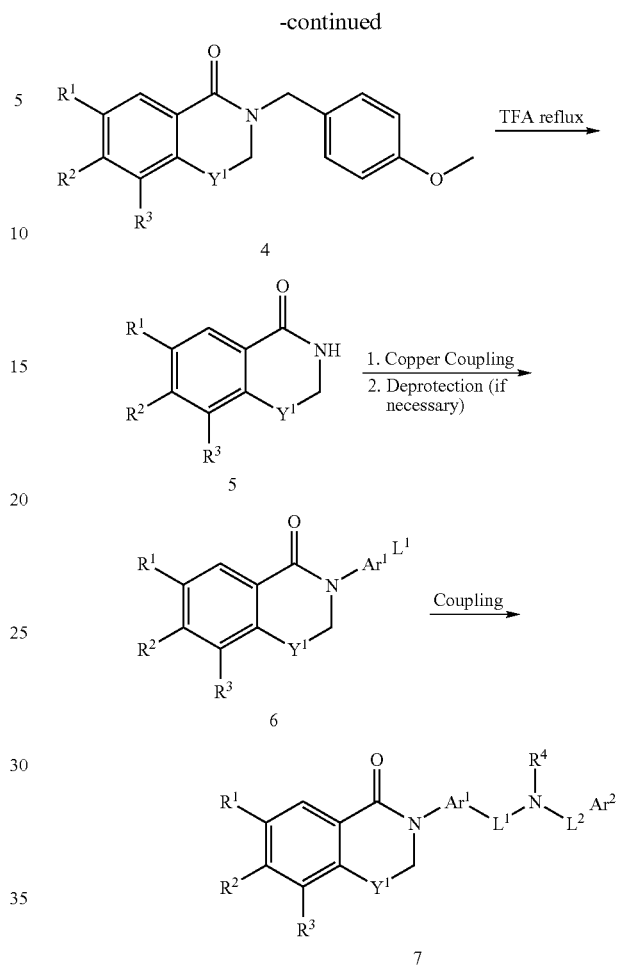

A compound of Formula I can be prepared by reacting a salicylic acid with acetic anhydride followed by acid chloride formation with oxalyl chloride which was converted to amides by reaction with various benzoate compounds. Transesterification under basic conditions to affords salicylamides 3. The intermediate salicylamides 3 were cyclized with paraformaldehyde to bicyclic compounds 4. The ester of compound 4 can be hydrolyzed by procedures known to one skilled in the art to yield free carboxylic acid. For example, a method of hydrolysis can be carried out using aqueous lithium hydroxide with a cosolvent, typically tetrahydrofuran or dioxane. Formation of the amide linkate can be accomplished by treating the carboxylic acid 5a coupling reagent, for example, HATU in the presence of a tertiary amine base, followed by addition of the amine to be coupled after a suitable period of time to give amide 6.

Scheme B illustrates another preparation of compounds of formula I with varying $Ar^1$, $Ar^2$, $L^1$ and $L^2$ groups.

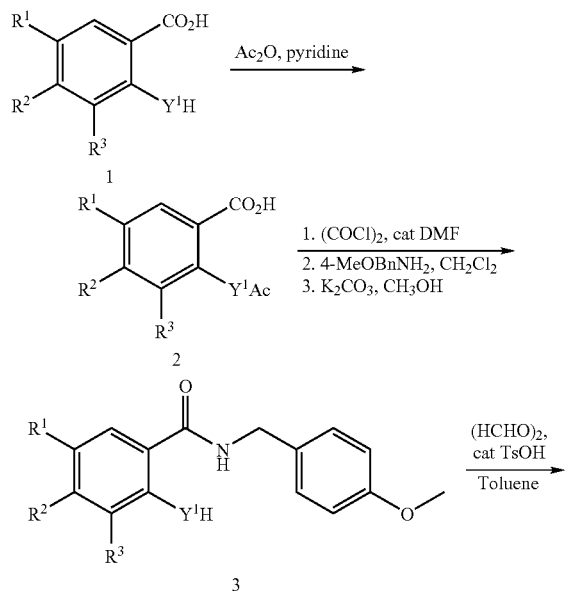

A compound of Formula I with varying $Ar^1$, $Ar^2$, $L^1$ and $L^2$ groups can be prepared by first synthesizing the common intermediate 5 in 4 steps (Scheme A). The acid chloride from Scheme A can be treated with p-methoxybenzylamine followed by cyclization with paraformaldehyde to afford the bicyclic ring system. The p-methoxybenzyl functionality can then be cleaved under acidic conditions to afford common intermediate 5. A variety of halo-substituted compounds can be coupled with 5 using a copper catalyzed coupling to give 6 followed by deprotection of any functional groups if necessary. Completion of the synthesis can be accomplished by coupling to form an amide using the conditions in scheme A, or by reductive amination to give a reduced linkage. The examples provided in detail below illustrate compounds prepared by the general methods provided.

Scheme C

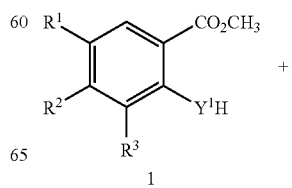

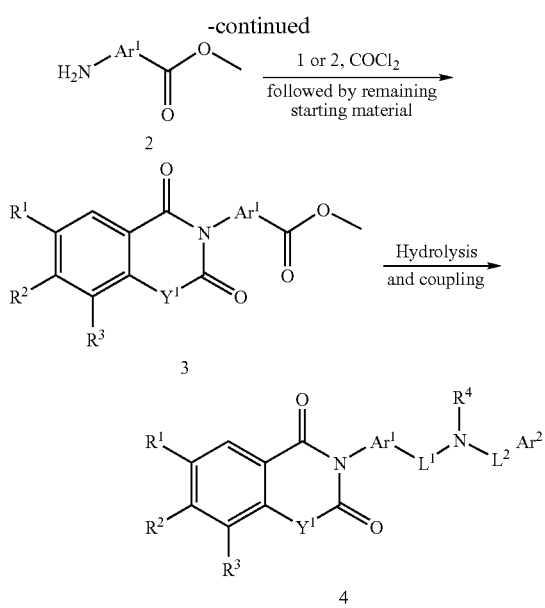

A compound of Formula I with varying $Ar^1$, $Ar^2$, $L^1$ and $L^2$ groups can be prepared by starting with a suitable anthranilic ester 1 and a suitably substituted $Ar^1$ aniline, 2, and treating one of the compounds with excess phosgene and a tertiary amine base if needed. After removal of excess phosgene the activated intermediate is taken up in a solvent such as dichloromethane, and the remaining reagent and a tertiary amine base is added. The cyclized product can then be further elaborated using conditions described in previous schemes to the final compound 4.

Compositions

In another aspect of the invention, pharmaceutical compositions are provided in which compounds of formulae I, II, III, IV, V, VI or VII, alone or in combination, are combined with a pharmaceutically acceptable carrier.

The pharmaceutical compositions of the invention may be in the form of solutions or suspensions. In the management of thrombotic disorders the compounds or pharmaceutical compositions of the invention may also be in such forms as, for example, tablets, capsules or elixirs for oral administration, suppositories, sterile solutions or suspensions or injectable administration, and the like, or incorporated into shaped articles.

Typical adjuvants which may be incorporated into tablets, capsules and the like include, but are not limited to, binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Additionally, dosage formulations of compounds of formulae I, II, III, IV, V, VI or VII, or pharmaceutical compositions containing a compound of the invention, to be used for therapeutic administration must be sterile. Sterility can be readily accomplished by filtration through sterile membranes such as 0.2 micron membranes, or by other conventional methods. Formulations typically will be stored in a solid form, preferably in a lyophilized form. While the preferred route of administration is orally, the dosage formulations of compounds of formulae I, II, III, IV, V, VI or VII, or pharmaceutical compositions of the invention may also be administered by injection, intravenously (bolus and/or infusion), subcutaneously, intramuscularly, colonically, rectally, nasally, transdermally or intraperitoneally. A variety of dosage forms may be employed as well including, but not limited to, suppositories, implanted pellets or small cylinders, aerosols, oral dosage formulations and topical formulations such as ointments, drops and dermal patches. The compounds of formulae I, II, III, IV, V, VI or VII, and pharmaceutical compositions of the invention may also be incorporated into shapes and articles such as implants which may employ inert materials such biodegradable polymers or synthetic silicones as, for example, SILASTIC, silicone rubber or other polymers commercially available. The compounds and pharmaceutical compositions of the invention may also be provided in the form of liposome delivery systems, such as small unilamellar vesicles, large unilamellar vesicles and multilamellar vesicles. Liposomes can be formed from a variety of lipids, such as cholesterol, stearylamine or phosphatidylcholines, used methods well known to one of skill in the art.

Methods of Treatment/Administration

In yet another aspect, the present invention provides methods for preventing or treating thrombosis in a mammal by administering to the mammal a therapeutically effective amount of a compound of formulae I, II, III, IV, V, VI or VII, alone or as part of a pharmaceutical composition of the invention as described above. Compounds of formulae I, II, III, IV, V, VI or VII, and pharmaceutical compositions of the invention containing a compound of formulae I, II, III, IV, V, VI or VII, of the invention are suitable for use alone or as part of a multi-component treatment regimen for the prevention or treatment of cardiovascular diseases, particularly those related to thrombosis. For example, a compound or pharmaceutical composition of the invention may be used as a drug or therapeutic agent for any thrombosis, particularly a platelet-dependent thrombotic indication, including, but not limited to, acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures, e.g., angioplasty, carotid endarterectomy, post CABG (coronary artery bypass graft) surgery, vascular graft surgery, stent placements and insertion of endovascular devices and protheses.

Compounds and pharmaceutical compositions of the invention may also be used as part of a multi-component treatment regimen in combination with other therapeutic or diagnostic agents in the prevention or treatment of thrombosis in a mammal. In certain preferred embodiments, compounds or pharmaceutical compositions of the invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. Still other agents that can be administered with the compounds of the present invention include antiplatelet compounds, fibrinolytics, anti-inflammatory compounds, cholesterol-lowering agents, blood-pressure-lowering agents and serotonin blockers. Suitable antiplatelet compounds include GPIIB-IIIa antagonists, aspirin, phosphodiesterase III inhibitors and thromboxane A2 receptor antagonists. Suitable anticoagulants include thrombin inhibitors, fXa inhibitors, coumadin (Warfarin), heparin and Lovenox®. Suitable anti-inflammatory compounds include non-steroidal anti-inflammatory agents, cyclooxygenase-2 inhibitors and rheumatoid arthritis agents. Coadministrations of these agents with the compounds of the invention may also allow for application of reduced doses of the thrombolytic agents and therefore minimize potential hemorrhagic side-effects. Compounds and pharmaceutical compositions of the invention may also act in a synergistic fashion to prevent reocclusion following a successful thrombolytic therapy and/or reduce the time to reperfusion.

In related methods, the compounds of the invention are useful for the prevention of a secondary ischemic event. In these methods, compounds of the invention or their pharmaceutical compositions are administered to a patient who has suffered a primary ischemic event in an amount sufficient to prevent or reduce the likely occurrence of a secondary event. Generally, the primary and/or secondary ischemic event is selected from myocardial infraction, stable or unstable angina, acute reocclusion after percutaneous transluminal coronary angioplasty, restenosis, thrombotic stroke, transient ischemic attack, reversible ischemic neurological deficit and intermittent claudication.

The compounds and pharmaceutical compositions of the invention may be utilized in vivo, ordinarily in mammals such as primates, (e.g., humans), sheep, horses, cattle, pigs, dogs, cats, rats and mice, or in vitro. The biological properties, as defined above, of a compound or a pharmaceutical composition of the invention can be readily characterized by methods that are well known in the art such as, for example, by in vivo studies to evaluate antithrombotic efficacy, and effects on hemostasis and hematological parameters.

Subjects (typically mammalian) in need of treatment using the compounds or pharmaceutical compositions of the invention may be administered dosages that will provide optimal efficacy. The dose and method of administration will vary from subject to subject and be dependent upon such factors as the type of mammal being treated, its sex, weight, diet, concurrent medication, overall clinical condition, the particular compound of formulae I, II, III, IV, V, VI or VII, employed, the specific use for which the compound or pharmaceutical composition is employed, and other factors which those skilled in the medical arts will recognize.

Therapeutically effective dosages may be determined by either in vitro or in vivo methods. For each particular compound or pharmaceutical composition of the invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the bodily fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, i.e., platelet ADP receptor inhibition, will be readily determined by one skilled in the art. Typically, applications of a compound or pharmaceutical composition of the invention are commenced at lower dosage levels, with dosage levels being increased until the desired effect is achieved. The compounds and compositions of the invention may be administered orally in an effective amount within the dosage range of about 0.01 to 1000 mg/kg in a regimen of single or several divided daily doses. If a pharmaceutically acceptable carrier is used in a pharmaceutical composition of the invention, typically, about 5 to 500 mg of a compound of formulae I, II, III, IV, V, VI or VII, is combined with a pharmaceutically acceptable carrier as called for by accepted pharmaceutical practice including, but not limited to, a physiologically acceptable vehicle, carrier, excipient, binder, preservative, stabilizer, dye, flavor, etc. The amount of active ingredient in these compositions is such that a suitable dosage in the range indicated is obtained.

The following preparations and examples are given to enable those skilled in the art to more clearly understand and to practice the present invention. They should not be considered as limiting the scope of the invention, but merely as being illustrative and representative thereof.

EXAMPLES

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Referring to the examples that follow, compounds of the present invention were synthesized using the methods described herein, or other methods, which are well known in the art.

The compounds and/or intermediates were characterized by high performance liquid chromatography (HPLC) using a Waters Alliance chromatography system with a 2695 Separation Module (Milford, Mass.). The analytical columns were C-18 SpeedROD RP-18E Columns from Merck KGaA (Darmstadt, Germany). The enantiomeric purity of the material was measured by chiral HPLC using an (R,R)-ULMO column (25 cm, ×4.6 mm, 5 um) from Regis Technologies eluting with 75/25 hexane/ethanol with 25 mM ammonium acetate and 1% triethyl amine. Alternately, characterization was performed using a Waters Unity (HPLC) system with Waters Acquity HPLC BEH C-18 2.1 mm×15 mm columns. A gradient elution was used, typically starting with 5% acetonitrile/95% water and progressing to 95% acetonitrile over a period of 5 minutes for the Alliance system and 1 minute for the Acquity system. All solvents contained 0.1% trifluoroacetic acid (TFA). Compounds were detected by ultraviolet light (UV) absorption at either 220 or 254 nm. HPLC solvents were from EMD Chemicals, Inc. (Gibbstown, N.J.). In some instances, purity was assessed by thin layer chromatography (TLC) using glass backed silica gel plates, such as, for example, EMD Silica Gel 60 2.5 cm×7.5 cm plates. TLC results were readily detected visually under ultraviolet light, or by employing well known iodine vapor and other various staining techniques.

Mass spectrometric analysis was performed on one of two Agilent 1100 series LCMS instruments with acetonitrile/water as the mobile phase. One system using TFA as the modifier and measures in positive ion mode and the other uses either formic acid or ammonium acetate and measures in both positive and negative ion modes.

Nuclear magnetic resonance (NMR) analysis was performed on some of the compounds with a Varian 400 MHz NMR (Palo Alto, Calif.). The spectral reference was either TMS or the known chemical shift of the solvent. Some compound samples were run at elevated temperatures (e.g., 75° C.) to promote increased sample solubility.

Preparative separations were carried out using either an Sq16x or an Sg100c chromatography system and prepackaged silica gel columns all purchased from Teledyne Isco, (Lincoln, Nebr.). Alternately, compounds and intermediates were purified by flash column chromatography using silica gel (230-400 mesh) packing material, or by HPLC using a C-18 reversed phase column. Typical solvents employed for the Isco systems and flash column chromatography were dichloromethane, methanol, ethyl acetate, hexane, acetone, aqueous hydroxyamine and triethyl amine. Typical solvents employed for the reverse phase HPLC were varying concentrations of acetonitrile and water with 0.1% trifluoroacetic acid.

Example 1

N-((5-chlorothiophen-2-yl)methyl)-4-(6-fluoro-7-(methylamino)-2,4-dioxo-1,2-dihydroquinazolin-3(4H)-yl)benzamide (4)

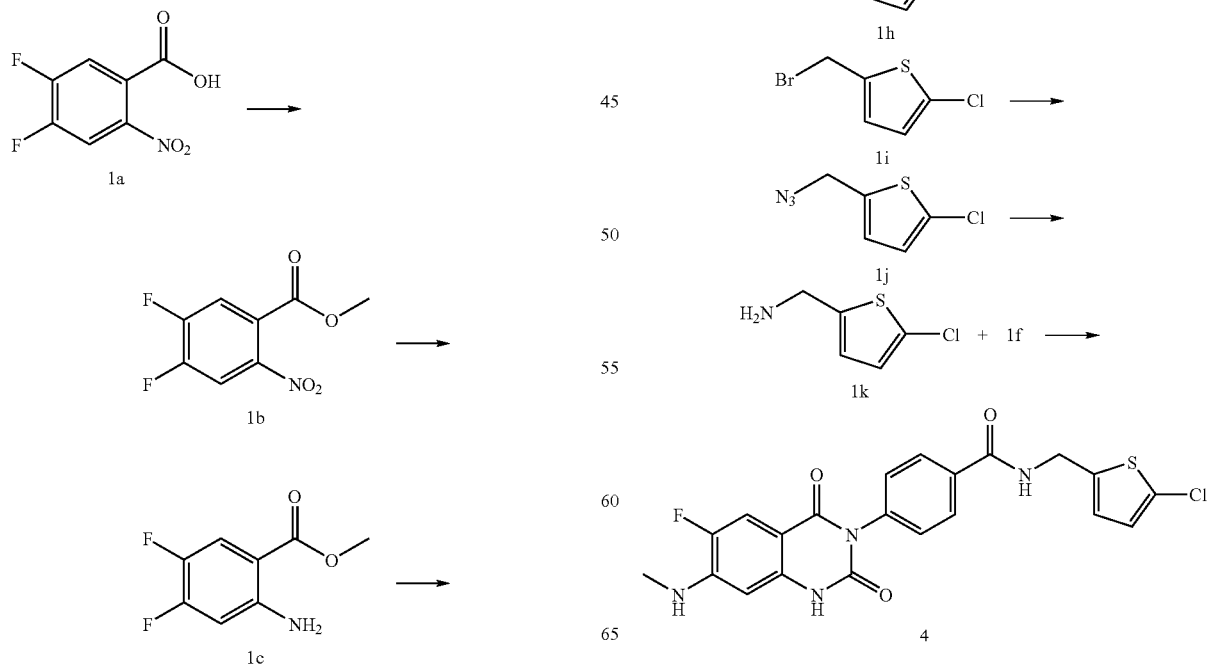

Step 1: 1a

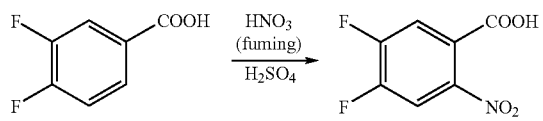

To 3,4-difluorobenzoic acid (120.0 g, 0.7589 mol) in a 2-L three-necked R. B. flask, was added concentrated $H_2SO_4$ (96.4%, 1.0 L). The mixture was mechanically stirred at room temperature for 1.0 hr and then cooled to 0° C. Fuming $HNO_3$ ($HNO_3$ content>90%, 57.30 mL, 1.273 mmol, 1.677 equiv) was added dropwise over 30 minutes. The mixture was stirred at room temperature for 16 h, slowly poured, in small portions, over crushed ice (5 Kg) with stirring. 4,5-Difluoro-2-nitrobenzoic acid precipitated out as a yellow solid. The slurry was stirred at 0° C. for 0.5 hr and then the solid product was collected via filtration through a Buckner funnel. The pale yellow solid 1a was rinsed with chilled water, and then air dried; yield 120 g (79%).

Step 2: 1b

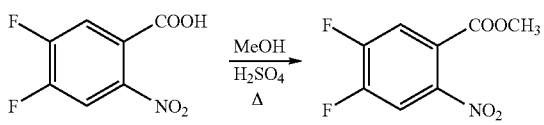

To a solution of 4,5-difluoro-2-nitrobenzoic acid 1a (40.0 g, 196.947 mmol) in anhydrous MeOH (1.0 L), was added concentrated $H_2SO_4$ (60.0 mL) and the clear mixture was refluxed for 2 days. Then methanol was removed in vacuo and the residue was partitioned between EtOAc and water. The EtOAc extract was washed with brine, dried over with anhydrous. $Na_2SO_4$, and concentrated to yield the methyl 4,5-difluoro-2-nitrobenzoate 1b as a pale yellow solid, 39.71 g (93%).

Step 3:

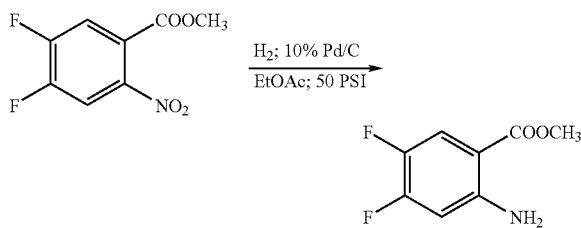

To a solution of methyl 4,5-difluoro-2-nitrobenzoate 1b (23.0 g, 106 mmol) in EtOAc (200 mL), was added 10% Pd/C (wet, 50% water, 6.0 g), and the mixture was shaken on a Parr hydrogenator at 50 PSI for 3 hr. The reaction mixture was then filtered through a celite pad and the filtrate was concentrated by rotary evaporation to yield methyl 2-amino-4,5-difluorobenzoate 1c as a colorless solid, 19.0 g (96%).

Step 4:

To a solution of aniline 1c (4.8 g, 26 mmol) in DCM (26 mL), was added diisopropylethyl amine (DIPEA) (4.9 mL, 28 mmol) and methyl 4-isocyanatobenzoate (5.0 g, 28 mmol). The reaction mixture was stirred for 2 days. A thick and off-white suspension was formed. The solid was collected through filtration. It contained the uncyclized urea (1d) and a small amount of the desired quinazolinedione. To a portion of the solid (6.95 g, 19 mmol) in dimethylsulfoxide (DMSO) (19 mL), was added methylamine (2M in THF, 19 mL, 38 mmol). The mixture was heated and stirred at 100° C. until all starting materials had been converted to the desired product. The mixture was then cooled, diluted with water to a total volume of 200 mL, and filtered. The solid was dried overnight by aspiration and in vacuo to afford 1e. $^1$H NMR (CDCl$_3$, 400 MHz): δ 11.33 (s, 1H), 8.02 (d, 2H), 7.41 (d, 2H), 7.38 (d, 1H), 6.82 (s, 1H), 6.21 (d, 1H), 3.87 (s, 3H), 2.78 (d, 3H).

Step 5:

To a solution of methyl ester 1e from step 4 in 80 mL of 1,4-dioxane, was added 1 M aqueous lithium hydroxide (38 mL, 38 mmol). The mixture was stirred at room temperature overnight, acidified with 3 M HCl until precipitation of the solid carboxylic acid ceased, diluted with water to a total volume of 300 mL, and filtered. The white solid was dried overnight by aspiration and then in vacuo to afford 1f as a dense white powder in quantitative yield. $^1$H NMR (CDCl$_3$, 400 MHz): δ 11.29 (s, 1H), 8.01 (d, 2H), 7.38 (m, 3H), 6.82 (s, 1H), 6.22 (d, 1H), 2.78 (s, 3H)

Step 6:

To a solution of 5-chlorothiophene-2-carboxaldehyde (1g) (3 mL, 28 mmol) in tetrahydrofuran (20 mL), was added sodium borohydride (1.6 g, 42 mmol). The reaction mixture was stirred for three hours at room temperature. The reaction was quenched with saturated ammonium chloride followed by 1 M hydrochloric acid. This mixture was then extracted with DCM and the organic layer was concentrated in vacuo to afford alcohol (1h) as a colorless oil $^1$H NMR (CDCl$_3$, 400 MHz): δ 6.78 (m, 2H), 4.71 (s, 2H).

Step 7:

To a solution of alcohol 1 h (2.39 g, 16 mmol) in diethyl ether (50 mL) at 0° C., was added phosphorous tribromide (1.5 mL, 16 mmol) slowly. The mixture was warmed to room temperature and stirred for 2 days. The solution was diluted with water, separated and the aqueous phase was extracted with diethyl ether. The organic layer was dried over magnesium sulfate, filtered and concentrated in vacuo to afford a 3:4 mixture of the desired bromide 1i and the starting alcohol 1 h. $^1$H NMR (DMSO, 400 MHz): δ 7.09 (d, 1H), 6.97 (d, 1H), 4.95 (s, 2H). $^1$H NMR Minor (DMSO, 400 MHz): δ7.07 (d, 1H), 6.93 (d, 1H), 4.62 (s, 2H).

Step 8:

To the crude mixture from step 7 in DMF (10 mL), was added sodium azide (2.0 g, 32 mmol). The mixture was stirred overnight, diluted with water and extracted twice with DCM. The combined organic layer was dried over magnesium sulfate, filtered and concentrated. Flash column chromatography (0-20% DCM/hexanes) afforded the desired alkyl azide (1j) which was used immediately for the next step (1.02 g, 33%). $^1$H NMR (DMSO, 400 MHz): δ 7.03 (m, 2H), 4.59 (s, 2H).

Step 9:

To a solution of azide 1j (1.02 g, 5.9 mmol) in methanol (20 mL), was added tin chloride dihydrate (2.67 g, 11.8 mmol). The mixture was stirred at room temperature until all of the azide had been converted to the amine as determined by HPLC. The reaction mixture was diluted with saturated sodium carbonate (10 mL) and ethyl acetate was added. The organic layer was dried, filtered and concentrated in vacuo to afford 1k as a light yellow oil. $^1$H NMR (DMSO, 400 MHz): a 6.89 (d, 1H), 6.73 (d, 1H), 3.82 (s, 2H), 2.01 (br s, 2H).

Step 10:

To a solution of acid 1f (50 mg, 0.15 mmol) in DMF (2 mL), was added DIPEA (40 uL, 0.23 mmol) and O-(7-Azabenzotriazol-1-yl)-N,N,N',N'-tetramethyluronium hexafluorophosphate (HATU) (104 mg, 0.28 mmol). After stirring for 10 min, the mixture was treated with amine 1k (41 mg, 0.28 mmol) and stirred overnight. The mixture was diluted with water (15 mL) and the resulting solid was isolated to afford the desired amide (4) as light beige solid. MS found for $C_{21}H_{16}ClFN_4O_3S$ as $(M+H)^+$ 459.1.

Example 2

N-((5-chlorothiophen-2-yl)methyl)-4-(6,7-difluoro-4-oxo-2H-benzo[e][1,3]oxazin-3(4H)-yl)benzamide (55)

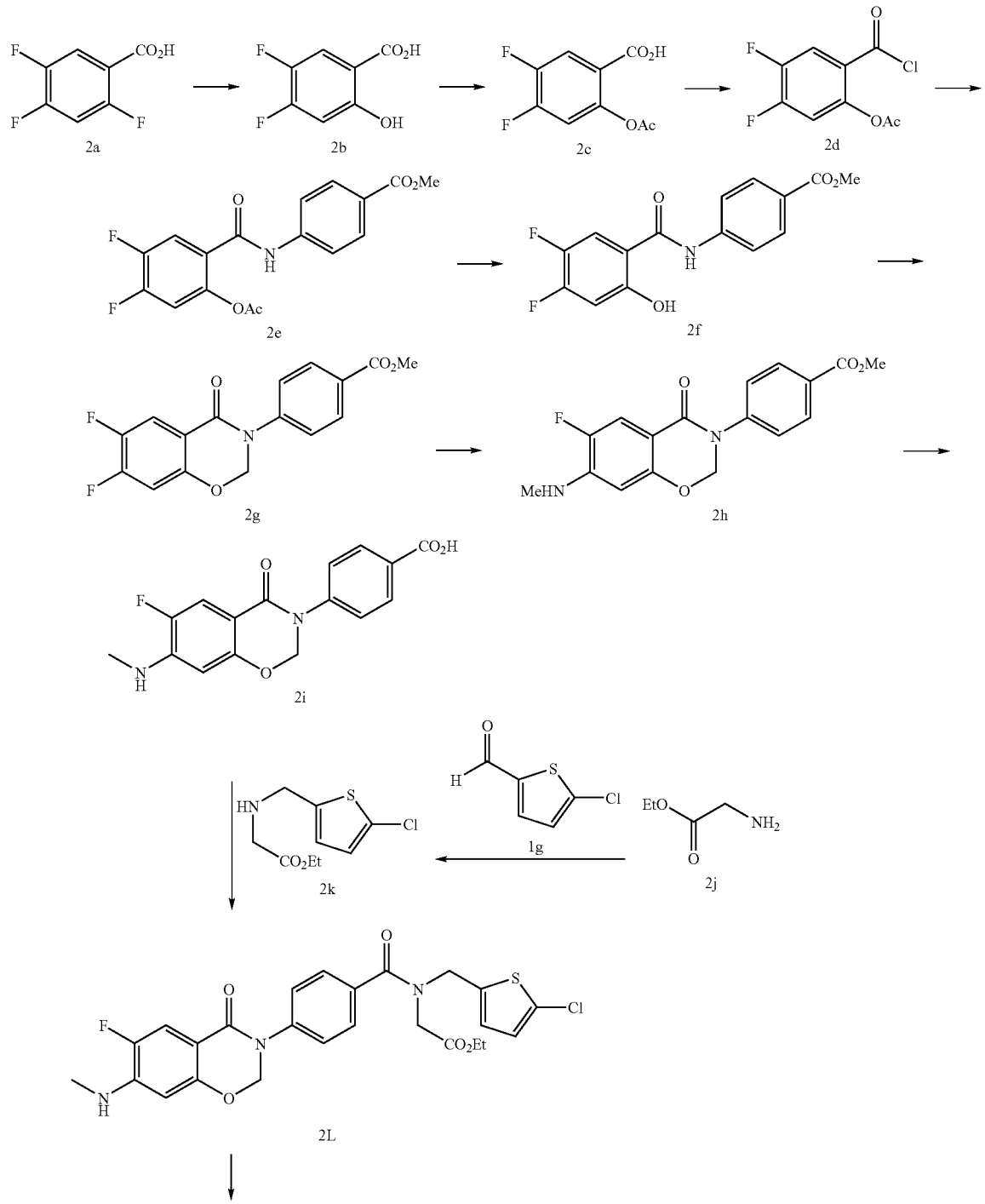

Scheme 2

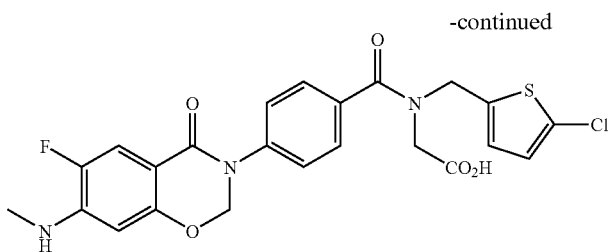

55

Step 1:

To a solution of trifluoride 2a (15 g, 96 mmol) in N,N'-dimethylimidazolidinone (DMI) (200 mL), was added sodium hydroxide (15 g, 382 mmol) slowly. The mixture was heated to 130° C. and stirred until all the starting material was consumed. The resulting thick beige semisolid was treated with crushed ice (2 L), acidified with concentrated hydrochloric acid to pH=2. The solid was collected by filtration and dried under vacuum overnight to afford (2b) as a white solid (14.2 g). $^1$H NMR (DMSO, 400 MHz): δ 7.73 (dd, 1H), 7.08 (dd, 1H).

Step 2:

To a suspension of phenol 2b (5.5 g, 32 mmol) in pyridine (10 mL), was added acetic anhydride (4.4 mL, 47 mmol) slowly. The mixture was stirred for at room temperature for 1.5 hrs. The reaction mixture was slowly poured into 3 M hydrochloric acid (120 mL) and extracted twice with ethyl acetate. The combined organic layers were dried over magnesium sulfate, filtered and concentrated to afford acetate 2c as a white solid (5.12 g, 72%). $^1$H NMR (DMSO, 400 MHz): δ 7.90 (dd, 1H), 7.49 (dd, 1H), 2.22 (s, 3H).

Step 3:

To a solution of acid 2c (1.16 g, 5.4 mmol) in DCM (20 mL), was added oxalyl chloride (0.70 mL, 8.1 mmol) followed by several drops of DMF. After gas evolution ceased, the reaction was checked by HPLC and determined to be complete. The mixture was concentrated and used immediately for the next step.

Step 4:

To a solution of methyl 4-aminobenzoate (0.90 g, 6.0 mmol) and DIPEA (1.4 mL, 3 eq.) in DCM (10 mL), was added crude acid chloride from step 3 in DCM (10 mL) dropwise. After the reaction was found to be complete by HPLC, the mixture was diluted with water and extracted once with DCM. The combined organic phases were dried over magnesium sulfate, filtered, then concentrate to afford a solid (1.34 g, 71% yield) as a mixture of the acetate 2e and the free phenol 2f.

Step 5:

To a solution of the crude product from the step 4 ((1.34 g, 3.8 mmol) in methanol (10 mL) and dioxane (10 mL), was added potassium carbonate (0.53 g, 3.8 mmol). The reaction mixture was stirred at room temperature for 90 min and then acidified with 1 M hydrochloric acid. Upon sitting overnight, a precipitate formed which was filtered and dried overnight by aspiration to afford phenol 2f as a white solid (0.86 g, 74%). $^1$H NMR (DMSO, 400 MHz): δ 11.86 (s, 1H), 10.57 (s, 1H), 7.96 (d, 2H), 7.94 (m, 1H), 7.83 (d, 2H), 7.00 (dd, 1H), 3.82 (s, 3H).

Step 6:

Amide 2f (0.86 g, 2.8 mmol) was combined with paraformaldehyde (0.42 g, 14 mmol) and toluene sulfonic acid (0.21 g, 1.12 mmol), the mixture was then diluted with 30 mL toluene and heated to reflux for 2 hours under a Dean-Stark trap previously filled with toluene. The reaction mixture was cooled to rt and partitioned with sodium bicarbonate and ethyl acetate. The aqueous phase was extracted again with ethyl acetate. The combined organic phases were dried over magnesium sulfate, filtered and concentrated to afford 2g as a light beige solid (0.92 g, quant). $^1$H NMR (DMSO, 400 MHz): δ 8.02 (d, 2H), 7.91 (dd, 1H), 7.50 (d, 2H), 7.46 (dd, 1H), 5.82 (s, 2H), 3.88 (s, 3H).

Step 7:

To a solution of difluoride 2g (0.92 g, 2.9 mmol) in DMSO (10 mL), was added methylamine (2 M in THF, 4.4 mL, 8.8 mmol). The reaction mixture was heated at 120° C. in a sealable tube for three hours. It was then cooled and diluted with water (100 mL). The resulting white precipitate was isolated by filtration and dried to afford 2h (0.81 g, 86%) as a white solid. $^1$H NMR (DMSO, 400 MHz): δ 7.96 (d, 2H), 7.49 (d, 2H), 7.36 (d, 1H), 6.72 (s, 1H), 6.25 (d, 1H), 5.68 (s, 2H), 3.84 (s, 3H), 2.76 (s, 3H).

Step 8:

To a solution of methyl ester 2 h (200 mg, 0.60 mmol) in dioxane (5 mL), was added 1 M lithium hydroxide (1.2 mL, 1.2 mmol). The mixture was stirred until all ester had been consumed (HPLC). The reaction was concentrated in vacuo, diluted with 1 mL 1M HCl and 3 mL of water. The resulting white solid was filtered and dried overnight to afford 2i (178 mg, 94%) as a light beige powder. $^1$H NMR (DMSO, 400 MHz): δ 7.97 (d, 2H), 7.48 (d, 2H), 7.36 (d, 1H), 7.10 (br s, 1H), 6.71 (s, 1H), 6.24 (d, 1H), 5.68 (s, 2H), 2.76 (s, 3H).

Step 9:

To a solution of carboxaldehyde 1g (168 uL, 1.58 mmol) and glycine ethyl ester hydrochloride 2j (200 mg, 1.44 mmol) in dichloroethane (10 mL), was added triethyl amine (TEA) (270 uL, 1.58 mmol), followed by sodium triacetoxyborohydride (0.46 g, 2.16 mmol). The mixture was stirred at room temperature overnight. The mixture was diluted with aqueous sodium carbonate/water/ethyl acetate. The layers separated and the aqueous phase was extracted with ethyl acetate and the combined organic phases was dried over magnesium sulfate, filtered, and concentrated in vacuo. The crude residue was purified by silica gel chromatography (1-10% ethyl acetate/DCM) to afford the desired amine 2k (73 mg, 22%) as a light yellow oil ($^1$H NMR (DMSO, 400 MHz): δ 6.93 (d, 1H), 6.81 (d, 1H), 4.10 (q, 2H), 3.85 (s, 2H), 1.18 (t, 3H).

Step 10:

Compound 2 L was synthesized in a manner similar to Example 1, Step 10. MS found for $C_{25}H_{23}ClFN_3O_5S$ as $(M+H)^+$ 532.2.

Step 11:

Compound 55 was synthesized in a manner similar to Example 1, Step 5. MS found for $C_{23}H_{19}ClFN_3O_5S$ as $(M+H)^+$ 504.1.

Example 3-5

2-(N-((5-chlorothiophen-2-yl)methyl)-4-(6-fluoro-7-(methylamino)-2,4-dioxo-1,2-dihydroquinazolin-3(4H)-yl)benzamido)acetic acid (Compound 6);

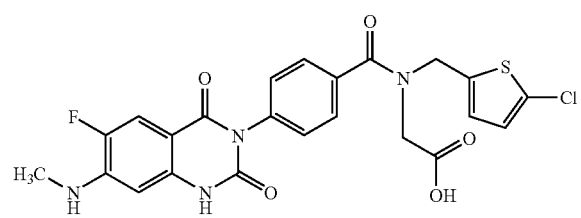

3-(N-((5-chlorothiophen-2-yl)methyl)-4-(6-fluoro-7-(methylamino)-2,4-dioxo-1,2-dihydroquinazolin-3(4H)-yl)benzamido)propanoic acid (Compound 40);

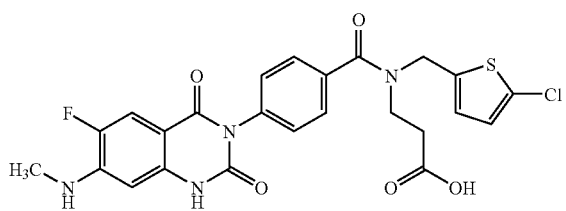

3-(N-((5-chlorothiophen-2-yl)methyl)-4-(6-fluoro-7-(methylamino)-4-oxo-2H-benzo[e][1,3]oxazin-3(4H)-yl)benzamido)propanoic acid (Compound 86);

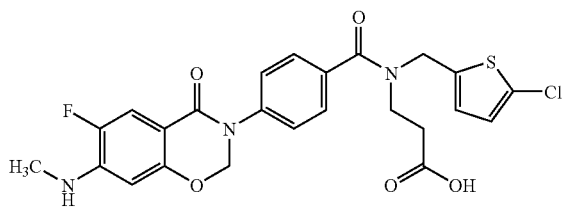

Compounds 6, 40 and 86 were made by the procedure similar to that described for Example 2. MS found for Compound 6 as $(M+H)^+$: 517.0. MS found for Compound 40 as $(M+H)^+$: 531.0. MS found for Compound 86 as $(M+H)^+$: 518.0.

Example 6

2-(5-chlorothiophen-2-yl)-2-(4-(6-fluoro-7-(methylamino)-2,4-dioxo-1,2-dihydroquinazolin-3(4H)-yl)benzamido)acetic acid (5)

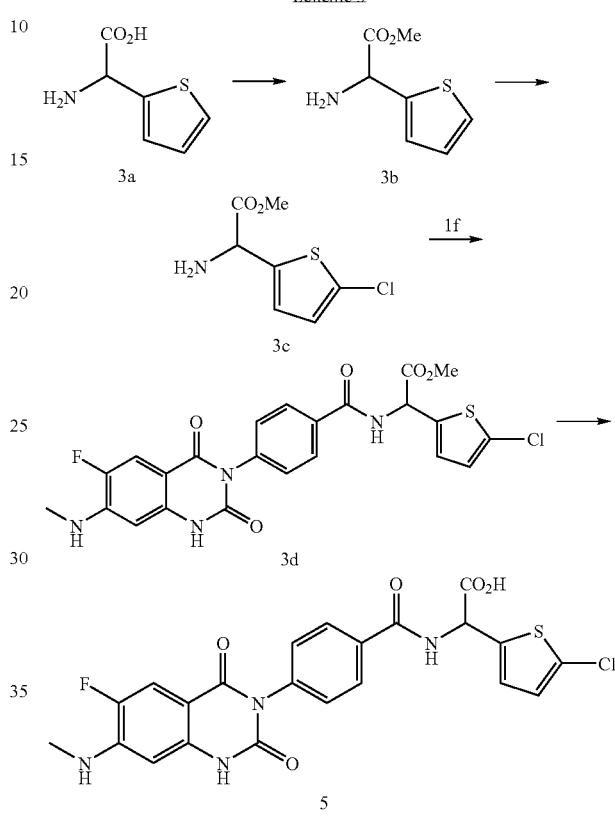

Scheme 3

Step 1:

To a suspension of amino acid 3a (10 g, 63 mmol) in a mixture of dioxane (300 mL) and methanol (150 mL), was added trimethylsilyldiazomethane (2 M in diethyl ether, 48 mL, 96 mmol). The mixture was stirred at room temperature until all starting acid had been converted to the methyl ester 3b. The mixture was concentrated to thick oil which was used immediately for the next step.

Step 2:

To a solution of 3b in acetic acid (120 mL) at 0° C., was added sulfuryl chloride (4.8 mL, 60 mmol) in three portions. More sulfuryl chloride (3 mL) was added slowly until all of the starting thiophene had been consumed. The crude mixture was concentrated in vacuo, then partitioned with aqueous sodium bicarbonate (carefully) and DCM. The organic layer was concentration and the crude residue was purified by silica gel chromatography (0-5% ethyl acetate/DCM) to afford 3c as a light yellow oil. The oil was dissolved in diethyl ether (100 mL) and acidified with 4 M hydrochloric acid in dioxane with vigorous stirring. The solid was then filtered to afford 3c as a beige HCl salt (6.24 g, 51%). MS found for $C_7H_8ClNO_2S$ as $(M+H)^+$ 206.0, 208.0.

Step 3:

Compound 3d (18) was synthesized in a manner similar to Example 1, Step 10. $^1$H NMR (DMSO, 400 MHz): δ 11.31 (s, 1H), 9.58 (d, 1H), 7.95 (d, 2H), 7.38 (m, 3H), 7.03 (d, 1H), 6.82 (s, 1H), 6.24 (d, 1H), 5.84 (d, 1H), 3.70 (s, 3H), 2.73 (d, 3H).

Step 4:

Compound 5 was synthesized by the procedure similar to that described for Example 1, Step 5. MS found for $C_{22}H_{16}ClFN_4O_5S$ as $(N+H)^+$ 503.0.

Example 7-8

2-(5-chlorothiophen-2-yl)-2-(4-(6-fluoro-7-(methylamino)-4-oxo-2H-benzo[e][1,3]oxazin-3(4H)-yl)benzamido)acetic acid (Compound 56);

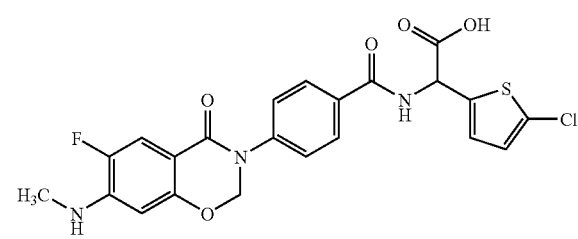

3-(5-chlorothiophen-2-yl)-2-(4-(6-fluoro-7-(methylamino)-4-oxo-2H-benzo[e][1,3]oxazin-3(4H)-yl)benzamido)propanoic acid (Compound 57);

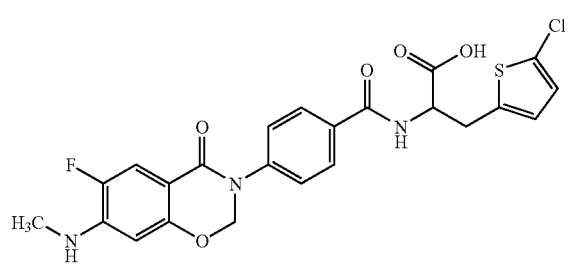

Compounds 56 and 57 were synthesized by the procedure similar to that described for Example 6. MS found for Compound 56 as $(M+H)^+$: 490.1. MS found for Compound 57 as $(M+H)^+$: 504.1.

Example 9

3-(5-chlorothiophen-2-yl)-3-(4-(6-fluoro-7-(methylamino)-2,4-dioxo-1,2-dihydroquinazolin-3(4H)-yl)benzamido)propanoic acid (27)

Scheme 4

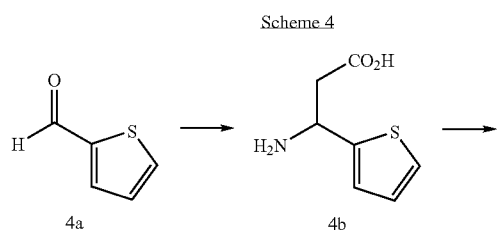

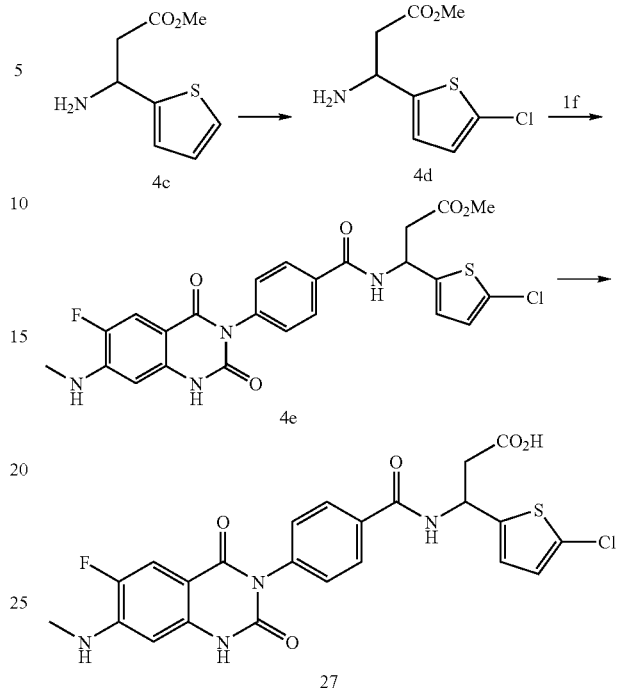

Step 1:

To a solution of thiophene carboxaldehyde 4a (3 mL, 30 mmol) in 1,4-dioxane (20 mL), was added malonic acid (3.43 g, 33 mmol) and ammonium acetate (4.6 g, 60 mmol). The mixture was heated to reflux overnight. It was cooled to rt and filtered. Upon sitting overnight, a precipitate formed which was isolated through filtration and dried in vacuo to afford 4b as a white solid (2.13 g, 34%). NMR (DMSO, 400 MHz): δ 7.54 (d, 1H), 7.28 (d, 1H), 7.05 (dd, 1H), 4.81 (dd, 1H), 3.04 (dd, 1H), 2.90 (dd, 1H).

Step 2:

To a solution of amino acid 4b (1.38 g, 8.1 mmol) DCM (10 mL) and methanol (10 mL), was added trimethylsilyldiazomethane (2 M in diethyl ether, 6 mL, 12 mmol). The reaction mixture was stirred at rt for 90 min and concentrated in vacuo. The residue was purified by silica gel chromatography (0-70% ethyl acetate/DCM) to afford the desired amino ester 4c as a colorless oil. NMR (DMSO, 400 MHz): δ 7.33 (d, 1H), 6.91 (m, 2H), 4.44 (dd, 1H), 3.56 (s, 3H), 2.68 (m, 2H).

Step 3:

Compound 4d was synthesized in a manner similar to Example 6, Step 2. MS found for $C_8H_8ClO_2S$ as $(M-NH_2)^+$ 203.0, 205.0.

Step 4:

Compound 4e was synthesized in a manner similar to Example 1, Step 10. NMR (DMSO, 400 MHz): δ 9.10 (d, 1H), 7.98 (d, 1H), 7.88 (d, 2H), 7.36 (m, 3H), 6.93 (d, 1H), 6.77 (s, 1H), 6.25 (d, 1H), 5.58 (dd, 1H), 3.58 (s, 3H), 3.05 (d, 2H), 2.77 (d, 3H).

Step 5:

Compound 27 was synthesized in a manner similar to Example 1, Step 5. MS found for $C_{23}H_{18}ClFN_4O_5S$ as $(M-H)^-$ 515.0, 517.0.

Example 10

3-(5-chlorothiophen-2-yl)-3-(4-(6-fluoro-7-(methylamino)-4-oxo-2H-benzo[e][1,3]oxazin-3(4H)-yl)benzamido)propanoic acid (Compound 79);

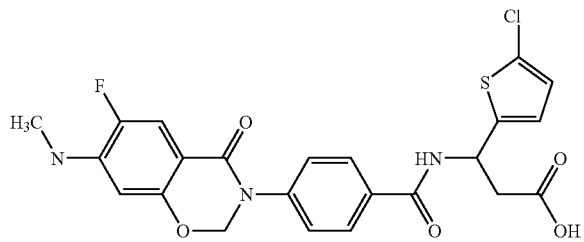

Compound 79 was synthesized in a manner similar to Example 9. MS found for Compound 79 as (M+H)+: 504.0.

Example 11

N-((5-chlorothiophen-2-yl)(1H-tetrazol-5yl)methyl)-4-(6-fluoro-7-(methylamino)-2,4-dioxo-1,2-dihydroquinazolin-3(4H)-yl)benzamide (Compound 7);

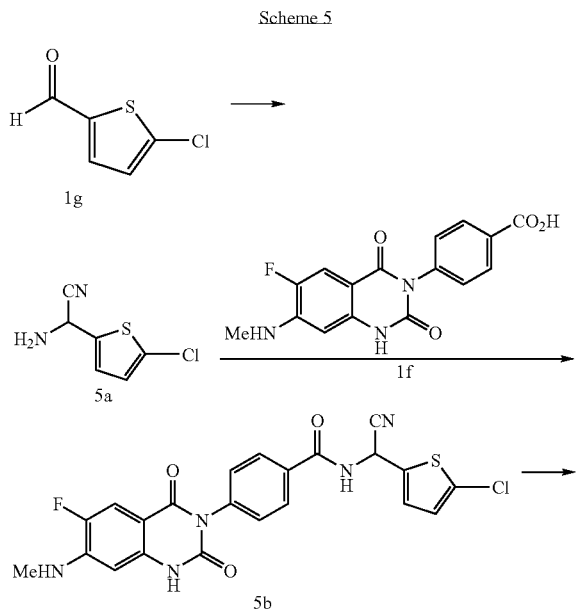

Step 1:

Aldehyde 1g (3 mL, 28 mmol) was mixed with trimethylsilylcyanide (4.5 mL, 34 mmol) and ca. 50 mg of $ZnI_2$. The resulting brown solution was stirred for 30 min at rt, then treated with ammonia (7 M in methanol, 20 mL, 140 mmol). The mixture was heated to 50° C. for 90 min. in a sealable tube. Ethyl acetate and water were added. The layers separated and the aqueous phase was extracted with ethyl acetate. The combined organic phases were concentrated to afford 5a (2.17 g, 45%) as a light beige solid. (DMSO, 400 MHz): δ 7.00 (d, 1H), 6.97 (d, 1H), 5.24 (s, 1H), 3.10 (s, 2H).

Step 2:

Compound 5b was synthesized in a manner similar to Example 1, Step 10. MS found for $C_{22}H_{15}ClFN_5O_3S$ as (M+H)+ 484.1.

Step 3:

To a solution of the nitrile 5b (65 mg, 0.14 mmol) in a 1:1 mixture of isopropanol and water (5 mL), was added sodium azide (18 mg, 0.28 mmol) and zinc bromide (16 mg, 0.07 mmol). The mixture was stirred at 80° C. until complete consumption of the starting material. The mixture was cooled to rt, concentrated in vacuo, and purified immediately by prep HPLC to afford compound 7 as a white solid. MS found for $C_{22}H_{16}ClFN_8O_3S$ as (M–H)– 525.0, 527.0.

Examples 12-24

N-((5-chlorothiophen-2-yl)(1H-tetrazol-5-yl)methyl)-4-(6-fluoro-7-(methylamino)-4-oxo-2H-benzo[e][1,3]oxazin-3(4H)-yl)benzamide (Compound 54)

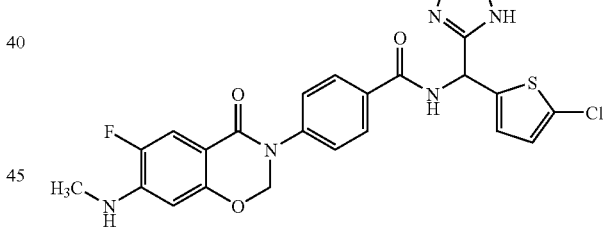

N-((3-chlorophenyl)(1H-tetrazol-5-yl)methyl)-4-(6-fluoro-7-(methylamino)-2,4-dioxo-1,2-dihydroquinazolin-3(4H)-yl)benzamide (Compound 11);

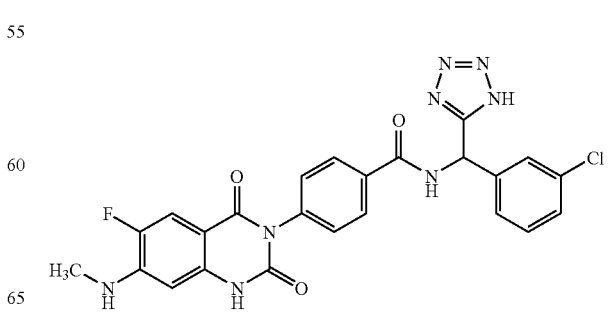

N-((4-chlorophenyl)(1H-tetrazol-5-yl)methyl)-4-(6-fluoro-7-(methylamino)-2,4-dioxo-1,2-dihydro-quinazolin-3(4H)-yl)benzamide (Compound 12);

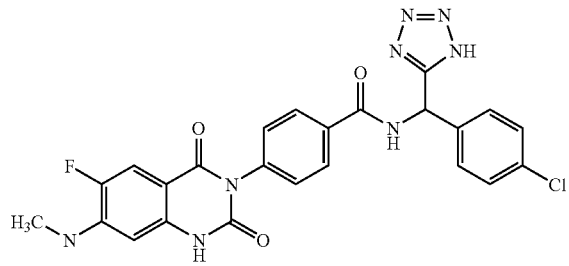

4-(6-fluoro-7-(methylamino)-4-oxo-2H-benzo[e][1,3]oxazin-3(4H)-yl)-N-((5-methylthiophen-2-yl)(1H-tetrazol-5-yl)methyl)benzamide (Compound 16);

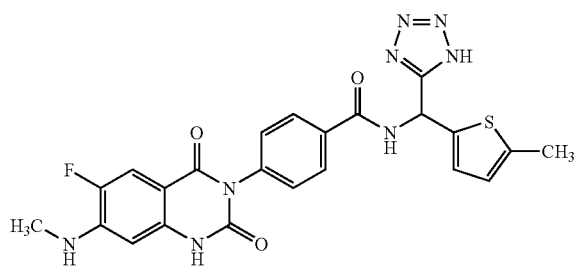

N-((1H-tetrazol-5-yl)(m-tolylmethyl)-4-(6-fluoro-7-(methylamino)-2,4-dioxo-1,2-dihydroquinazolin-3(4H)-yl)benzamide (Compound 22);

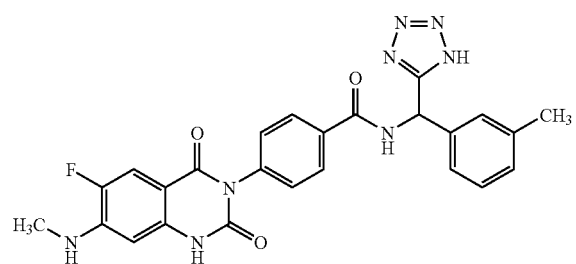

4-(6-fluoro-7-(methylamino)-2,4-dioxo-1,2-dihydro-quinazolin-3(4H)-yl)-N-((3-methoxyphenyl)(1H-tetrazol-5-yl)methyl)benzamide (Compound 23);

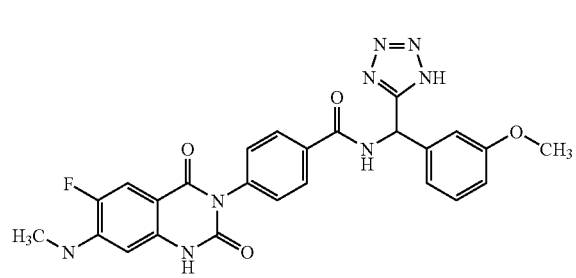

4-(6-fluoro-7-(methylamino)-2,4-dioxo-1,2-dihydro-quinazolin-3(4H)-yl)-N-((3-fluorophenyl)(1H-tetrazol-5-yl)methyl)benzamide (Compound 24);

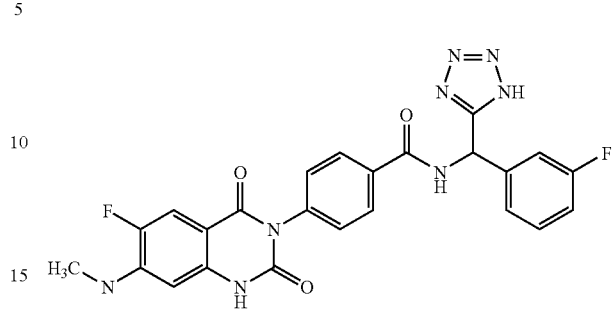

N-((2-chlorophenyl)(1H-tetrazol-5-yl)methyl)-4-(6-fluoro-7-(methylamino)-2,4-dioxo-1,2-dihydro-quinazolin-3(4H)-yl)benzamide (Compound 28);

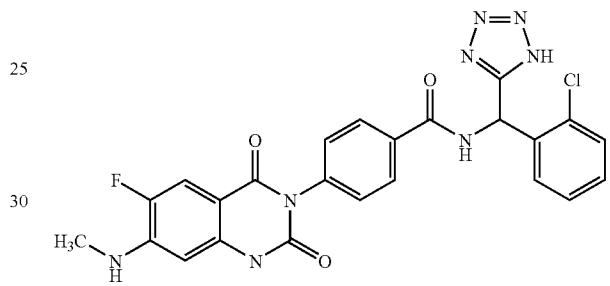

N-((3,4-dichlorophenyl)(1H-tetrazol-5-yl)methyl)-4-(6-fluoro-7-(methylamino)-2,4-dioxo-1,2-dihydro-quinazolin-3(4H)-yl)benzamide (Compound 29);

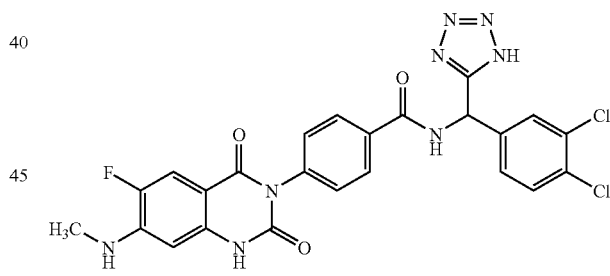

N-((3,5-dichlorophenyl)(1H-tetrazol-5-yl)methyl)-4-(6-fluoro-7-(methylamino)-2,4-dioxo-1,2-dihydro-quinazolin-3(4H)-yl)benzamide (Compound 30);

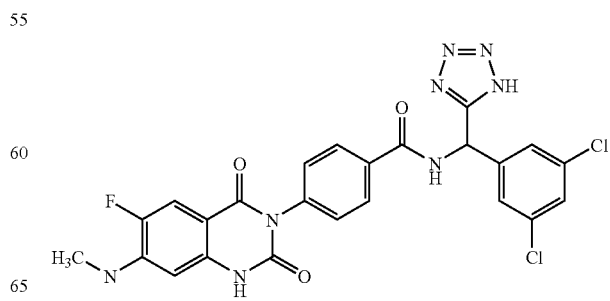

N-((1H-tetrazol-5-yl(3-(trifluoromethoxy)phenyl)methyl)-4-(6-fluoro-7-(methylamino)-2,4-dioxo-1,2-dihydroquinazolin-3(4H)-yl)benzamide (Compound 31);

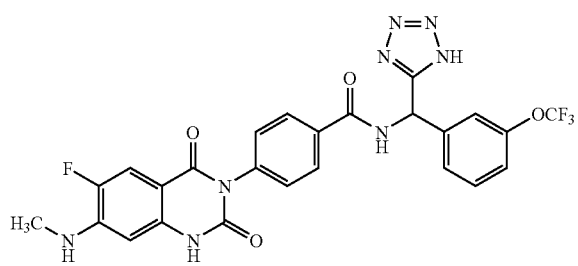

N-((1H-tetrazol-5-yl(3-(trifluoromethyl)phenyl)methyl)-4-(6-fluoro-7-(methylamino)-2,4-dioxo-1,2-dihydroquinazolin-3(4H)-yl)benzamide (Compound 34)

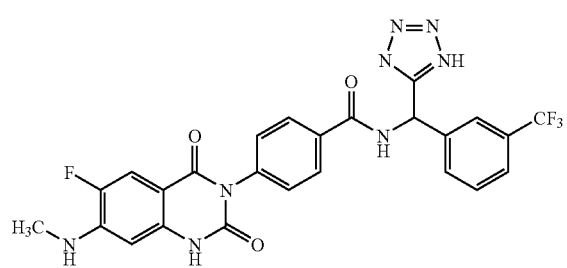

4-(6-fluoro-7-(methylamino)-4-oxo-2H-benzo[e][1,3]oxazin-3(4H)-yl)-N-((5-methylthiophen-2-yl)(1H-tetrazol-5-yl)methyl)benzamide (Compound 61);

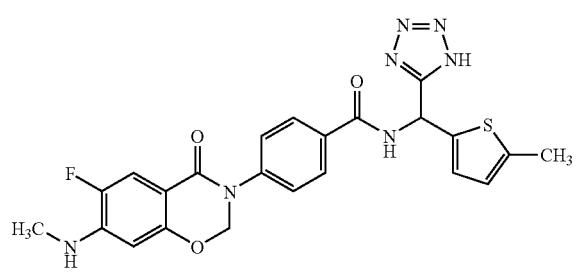

N-((5-chlorothiophen-2-yl)(1H-tetrazol-5-yl)methyl)-4-(6-fluoro-7-(methylamino)-4-oxo-2H-benzo[e][1,3]oxazin-3(4H)-yl)benzamide (54) and compounds 11, 12, 16, 22, 23, 24, 28, 29, 30, 31, 34 and 61 were synthesized by the procedure similar to that described for Example 11. Compound 54. (DMSO, 400 MHz): δ 9.76 (s, 1H), 7.94 (d, 2H), 7.47 (d, 2H), 7.35 (d, 1H), 7.04 (s, 2H), 6.88 (d, 1H), 6.71 (s, 1H), 6.25 (d, 1H), 5.64 (s, 2H), 2.74 (s, 3H). MS found for Compound 54 as (M+H)$^+$: 514.0. MS found for Compound 11 as (M+H)$^+$: 521.3. MS found for Compound 12 as (M+H)$^+$: 521.3. MS found for Compound 16 as (M+H)$^+$: 507.0. MS found for Compound 22 as (M+H)$^+$: 501.0. MS found for Compound 23 as (M+H)$^+$: 517.0. MS found for Compound 24 as (M+H)$^+$: 505.0. MS found for Compound 28 as (M+H)$^+$: 521.0. MS found for Compound 29 as (M+H)$^+$: 556.0. MS found for Compound 30 as (M+H)$^+$: 556.0. MS found for Compound 31 as (M+H)$^+$: 571.0. MS found for Compound 34 as (M+H)$^+$: 555.0. MS found for Compound 61 as (M+H)$^+$: 492.3.

Example 25

N-((5-chlorothiophen-2-yl)(5-oxo-4,5-dihydro-1,2,4-oxadiazol-3-yl)methyl)-4-(6-fluoro-7-(methylamino)-2,4-dioxo-1,2-dihydroquinazolin-3(4H)-yl)benzamide (21)

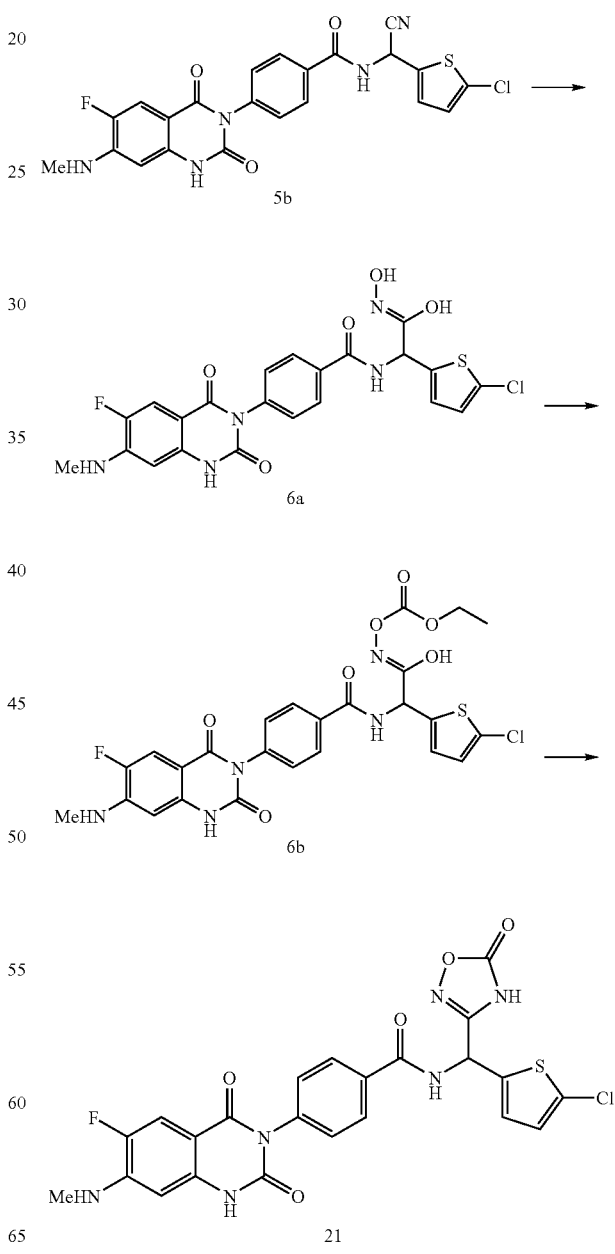

-continued

6a →

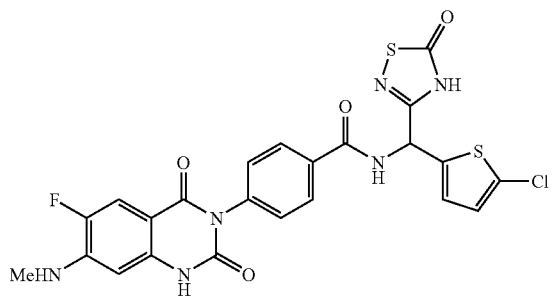

6a →

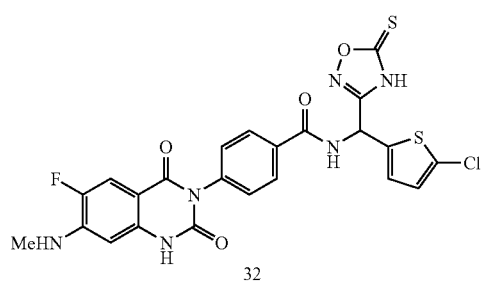

Step 1:

To a solution of nitrile 5b (100 mg, 0.21 mmol) in DMSO (1 mL), was added hydroxylamine hydrochloride (73 mg, 1.05 mmol) and DIPEA (183 uL, 1.05 mmol). The reaction mixture was heated to 70° C. for 2 hrs. The reaction mixture was diluted with water (ca. 10 mL). The resulting solid was isolated through filtration to afford 6a as a light beige solid in quantitative yield. (DMSO, 400 MHz): δ 9.08 (d, 1H), 7.82 (d, 2H), 7.37 (m, 3H), 6.97 (d, 1H), 6.91 (d, 1H), 6.84 (s, 1H), 6.27 (d, 1H), 5.88 (d, 1H), 5.73 (s, 1H), 2.77 (d, 3H).

Step 2:

To a solution of hydroxamidine 6a (50 mg, 0.10 mmol) in DMF (2 mL), was added pyridine (9 uL, 0.11 mmol), followed by ethyl chloroformate (10 uL, 0.10 mmol). The mixture was stirred at rt overnight. Water (10 mL) was added and the solid was isolated through filtration to afford 6b in quantitative yield. (DMSO, 400 MHz): δ 11.28 (s, 1H), 9.13 (d, 1H), 7.93 (d, 2H), 7.42 (d, 2H), 7.35 (s, 1H), 7.00 (s, 2H), 6.83 (s, 1H), 6.77 (s, 2H), 6.25 (d, 1H), 5.93 (d, 1H), 3.97 (q, 2H), 2.79 (d, 3H), 1.24 (t, 3H).

Step 3:

To a solution of carbonate 6b (465 mg, 0.90 mmol) in DMF (5 mL), was added cesium carbonate (350 mg, 1.1 μmol). The mixture was stirred at rt overnight. The reaction mixture was diluted with water and 1 M HCl to a total volume of 40 mL and a pH of approximately 3. The solid was filtered and washed with water, then purified by prep HPLC to afford compound 21 (107 mg, 22%). (DMSO, 400 MHz): δ 11.30 (s, 1H), 9.29 (d, 1H), 7.91 (d, 2H), 7.34 (m, 3H), 6.80 (s, 2H), 6.26 (d, 1H), 6.13 (d, 1H), 2.74 (d, 3H). MS found for Compound 21 as (M+H)+:543.0.

Example 26

N-((5-chlorothiophen-2-yl)(5-oxo-4,5-dihydro-1,2,4-thiadiazol-3-yl)methyl)-4-(6-fluoro-7-(methylamino)-2,4-dioxo-1,2-dihydroquinazolin-3(4H)-yl)benzamide (Compound 25)

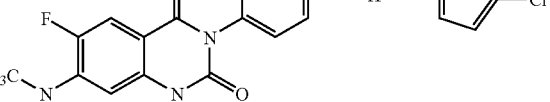

To a solution of 6a (100 mg, 0.19 mmol) in tetrahydrofuran (2 mL), was added thiocarbonyldiimidazole (37 mg, 0.21 mmol). The reaction mixture was stirred at rt for 30 min. Silica gel (1 g) in 20 mL of a 5:1 mixture of chloroform and methanol was added to the reaction and the suspension was stirred at rt overnight. The mixture was concentrated and purified by prep HPLC to afford 25 as a white solid (9 mg, 10%). MS found for $C_{23}H_{16}ClFN_6O_4S_2$ as (M−H)⁻ 557.0, 559.0.

Example 27

N-((5-chlorothiophen-2-yl)(5-thioxo-4,5-dihydro-1,2,4-oxadiazol-3-yl)methyl)-4-(6-fluoro-7-(methylamino)-2,4-dioxo-1,2-dihydroquinazolin-3(4H)-yl)benzamide (Compound 32).

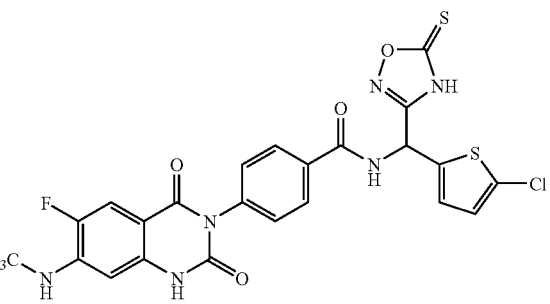

To a solution of 6a (100 mg, 0.19 mmol) in DMF (3 mL), was added thiocarbonyldiimidazole (52 mg, 0.29 mmol) and DBU (113 uL, 0.76 mmol). The mixture was stirred at rt for 4-5 hours, diluted with water and purified by prep HPLC to afford 32 as a white solid. MS found for $C_{23}H_{16}ClFN_6O_4S_2$ as (M−H)⁻ 556.7, 558.8.

Examples 28

N-((5-chlorothiophen-2-yl)(5-oxo-4,5-dihydro-1,2,4-oxadiazol-3-yl)methyl)-4-(6-fluoro-7-(methylamino)-4-oxo-2H-benzo[e][1,3]oxazin-3(4H)-yl)benzamide (Compound 71);

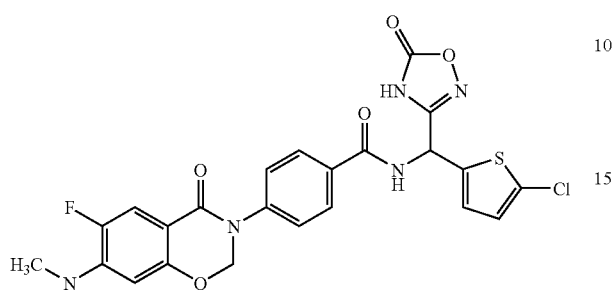

Compound 71 was made by the procedure similar to that described for Example 25. Title compound: MS found for $C_{23}H_{18}ClFN_4O_5S$ as $(M+H)^+$ 530.0.

Example 29

N-((5-chlorothiophen-2-yl)(5-thioxo-4,5-dihydro-1,2,4-oxadiazol-3-yl)methyl)-4-(6-fluoro-7-(methylamino)-4-oxo-2H-benzo[e][1,3]oxazin-3(4H)-yl)benzamide (Compound 75);

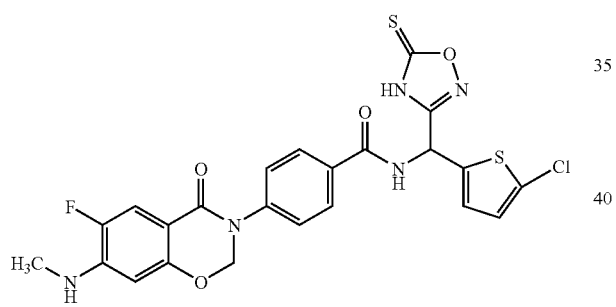

Compound 75 was synthesized by the procedure similar to that described for Example 27. MS found for Compound 75 as $(M+H)^+$: 545.8.

Example 30

2-(5-chlorothiophen-2-yl)-2-(4-(6-fluoro-7-(methylamino)-2,4-dioxo-1,2-dihydroquinazolin-3(4H)-yl)-3-methoxybenzamido)acetic acid (51)

Scheme 7

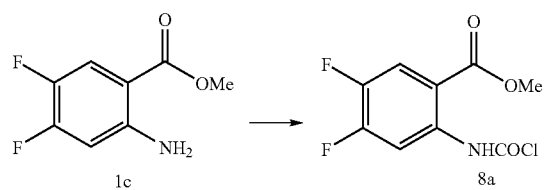

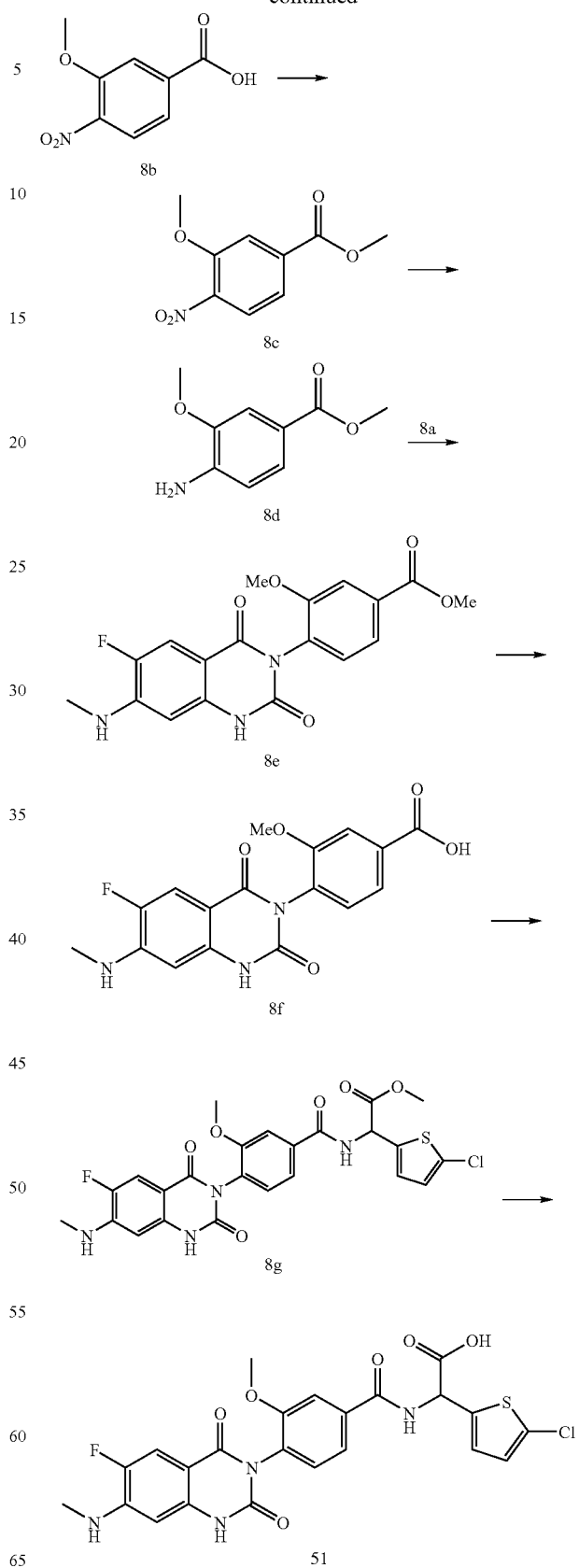

Step 1:

To difluoroanthranalide 1c (5.69 g, 30 mmol), was added phosgene in toluene ((1.9 M, 160 mL, 300 mmol). The reaction mixture was stirred at rt overnight, concentrated in vacuo, evaporated from toluene (20 mL), and dried under vacuum to afford a light beige solid 8a. The material was found to give the desired urea when treated with ammonia but was not otherwise characterized.

Step 2:

Anhydrous HCl was made by addition of thionyl chloride (1.46 mL, 20.4 mmol) and methanol (10 mL) at 0° C. To this was added 3-methoxy-4-nitrobenzoic acid 8b (2.00 g, 10.2 mmol). The mixture was stirred at room temperature overnight, concentrated, diluted with aqueous sodium bicarbonate, and extracted with dichloromethane. The organic layer was concentrated in vacuo to afford methyl ester 8c in quantitative yield. $H^1$ NMR (400 MHz, $CDCl_3$) δ 7.82 (d, 1H), 7.75 (s, 1H), 7.68 (d, 1H), 4.02 (s, 3H), 3.99 (s, 3H).

Step 3:

To solution of 8c in ethyl acetate (20 mL), was added 10% Pd/C (Degussa, 200 mg). The reaction mixture was stirred under an atmosphere of hydrogen overnight, filtered through celite and concentrated to give the aniline 8d as a white solid (1.54 g, 83% for 2 steps). $H^1$ NMR (400 MHz, DMSO-$d_6$) δ 3.73 (s, 3H), 3.78 (s, 3H), 5.59 (s, 2H), 6.60 (d, 1H), 7.28 (s, 1H), 7.35 (dd, 1H).

Step 4:

To a solution of aniline 8d (200 mg, 1.1 mmol) in DCM (10 mL), was added DIPEA (290 uL, 1.66 mmol), followed by carbamoyl chloride 8a (0.35 g, 1.66 mmol). The mixture was stirred overnight, concentrated in vacuo, and the crude product (urea and a small amount of 8e) was used for the next step without further purification.

Step 5:

To a solution of crude product from step 4 in DMSO (5 mL), was added methyl amine (2M in THF, 1.7 mL 3.3 mmol). The mixture was heated to 100° C. in a sealable tube overnight. The reaction mixture was diluted with water and the solid was isolated through filtration to afford 8e as a light beige solid (330 mg, 80% for 2 steps). MS found for $C_{18}H_{16}FN_3O_5$ as (M+H)+ 374.2.

Step 6:

Compound 8f was synthesized in a manner similar to Example 1, Step 5.

Step 7:

Compound 8g was prepared using a procedure similar to Example 1, step 10 using 8f and 3c. (DMSO, 400 MHz): δ 7.68 (d, 1H), 7.60 (d, 1H), 7.45 (d, 1H), 7.33 (d, 1H), 6.93 (d, 1H), 6.93 (d, 1H), 6.80 (d, 1H), 6.31 (d, 1H), 5.65 (s, 1H), 3.88 (s, 3H), 2.93 (s, 3H).

Step 8:

Compound 51 was synthesized using a procedure similar to Example 1, step 5. MS found for Compound 51 as (M+H)+: 533.0.

Example 31

2-(3-chlorophenyl)-2-(4-(6-fluoro-7-(methylamino)-2,4-dioxo-1,2-dihydroquinazolin-3(4H)-yl)benzamido)acetic acid 15

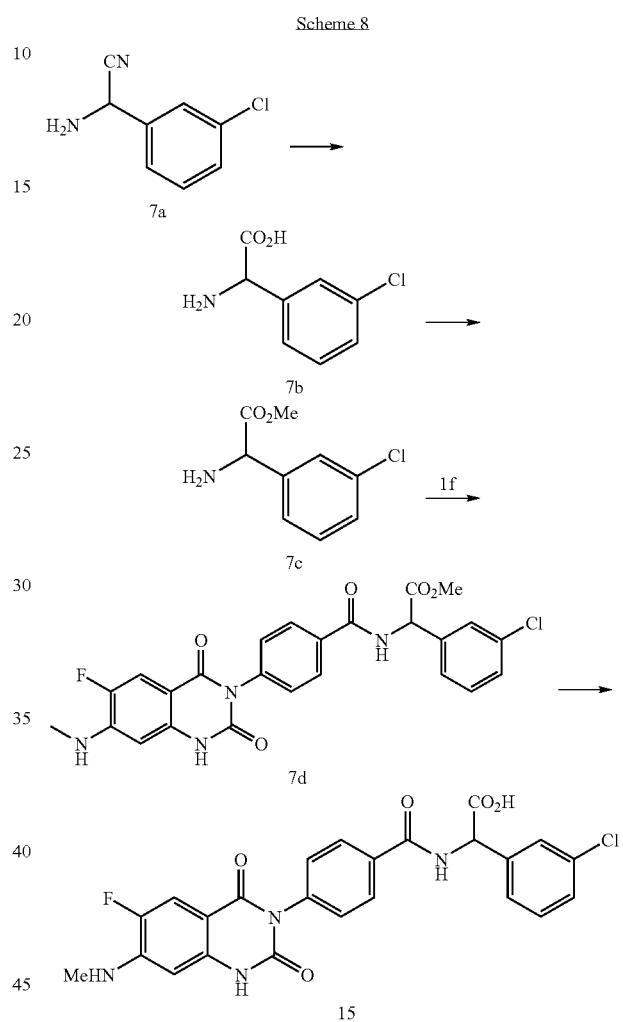

Step 1:

Aminonitrile 7a (prepared from 3-chlorobenzaldehyde using similar procedure described for 5a) (0.76 g, 3.8 mmol) was dissolved in 6 M hydrochloric acid (15 mL). The mixture was refluxed for 2 hrs, cooled to rt, concentrated and used immediately for the next step.

Step 2:

Compound 7c was synthesized in a manner similar to Example 30, Step 2. The crude product was used immediately for the next step.

Step 3:

Compound 7d was synthesized in a manner similar to Example 1, Step 10.

Step 4:

Compound 15 was synthesized in a manner similar to Example 1, Step 5. (DMSO, 400 MHz): δ 11.27 (s, 1H), 9.17 (dd, 1H), 7.92 (d, 2H), 7.53 (m, 2H), 7.38 (m, 4H), 6.80 (s, 1H), 6.23 (d, 1H), 5.64 (dd, 1H), 2.77 (d, 3H). MS found for Compound 15 as (M+H)+: 497.0.

Examples 32-38

2-(4-(6-fluoro-7-(methylamino)-2,4-dioxo-1,2-dihydroquinazolin-3(4H)-yl)benzamido)-2-(5-methylthiophen-2-yl)acetic acid (Compound 19);

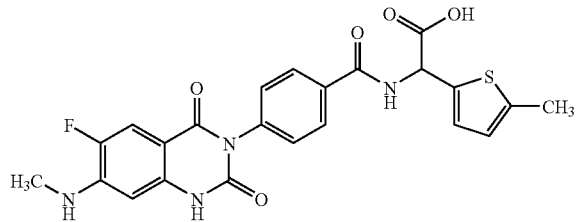

2-(4-(6-fluoro-7-(methylamino)-4-oxo-2H-benzo[e][1,3]oxazin-3(4H)-yl)benzamido)-2-phenylacetic acid (Compound 58);

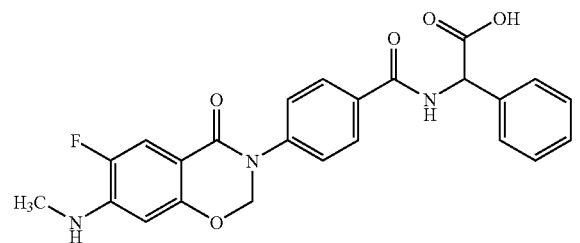

(S)-2-(4-(6-fluoro-7-(methylamino)-4-oxo-2H-benzo[e][1,3]oxazin-3(4H)-yl)benzamido)-3-phenylpropanoic acid (Compound 60);

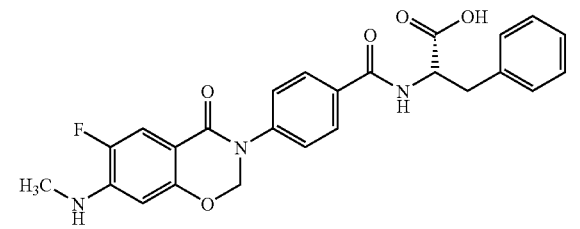

2-(4-(6-fluoro-7-(methylamino)-4-oxo-2H-benzo[e][1,3]oxazin-3(4H)-yl)benzamido)-2-(thiophen-2-yl)acetic acid (Compound 63);

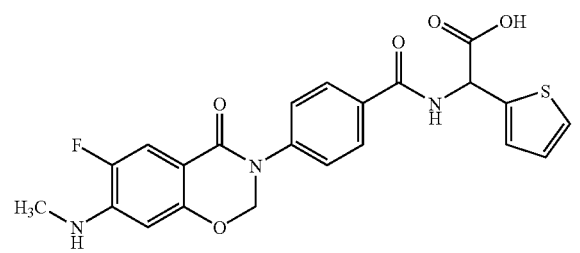

2-(4-(6-fluoro-7-(methylamino)-4-oxo-2H-benzo[e][1,3]oxazin-3(4H)-yl)benzamido)-3-(thiophen-2-yl)propanoic acid (Compound 64);

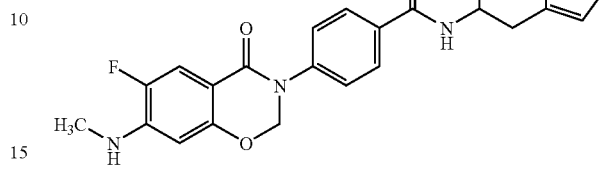

(S)-2-(4-(6-fluoro-7-(methylamino)-4-oxo-2H-benzo[e][1,3]oxazin-3(4H)-yl)benzamido)-2-phenylacetic acid (Compound 65);

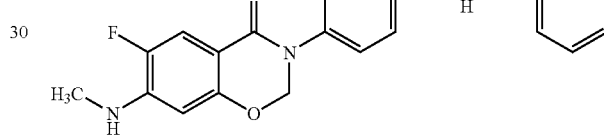

2-(3-chlorophenyl)-2-(4-(6-fluoro-7-(methylamino)-4-oxo-2H-benzo[e][1,3]oxazin-3(4H)-yl)benzamido)acetic acid (Compound 81);

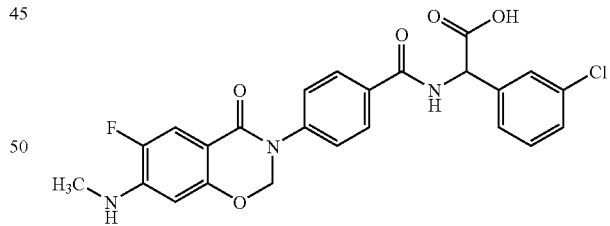

Compounds 19, 58, 60, 63, 64, 65, and 81 were synthesized by the procedure similar to that described for Example 31 from the corresponding commercially available amino acid after esterification. MS found for Compound 19 as (M+H)$^+$: 483.0. MS found for Compound 58 as (M+H)$^+$: 450.1. MS found for Compound 60 as (M+H)$^+$: 464.2. MS found for Compound 63 as (M+H)$^+$: 456.0. MS found for Compound 64 as (M+H)$^+$: 470.2. MS found for Compound 65 as (M+H)$^+$: 448.2. MS found for Compound 81 as (M+H)$^+$: 484.0.

Example 39

2-(4-(6-fluoro-7-(methylamino)-4-oxo-2H-benzo[e][1,3]oxazin-3(4H)-yl)benzamido)-3-phenylpropanoic acid (Compound 59);

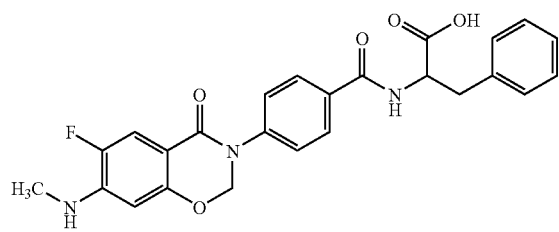

The titled compound was made by the procedure similar to that described for the Examples above from the corresponding commercially available amino acid. (DMSO, 400 MHz): δ 8.71 (d, 1H), 7.82 (d, 2H), 7.40 (d, 2H), 7.13-7.38 (m, 6H), 6.72 (s, 1H), 6.22 (d, 1H), 5.63 (s, 2H), 4.60 (m, 1H), 3.18 (dd, 1H), 3.07 (dd, 1H), 2.78 (s, 3H).

Example 40

2-(5-chlorothiophen-2-yl)-2-(4-(6-fluoro-7-(methylamino)-2,4-dioxo-1,2-dihydroquinazolin-3(4H)-yl)-2-methylbenzamido)acetic acid (Compound 41)

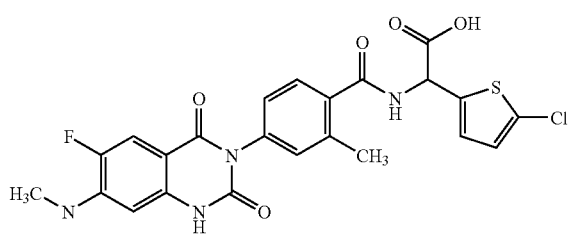

Scheme 9

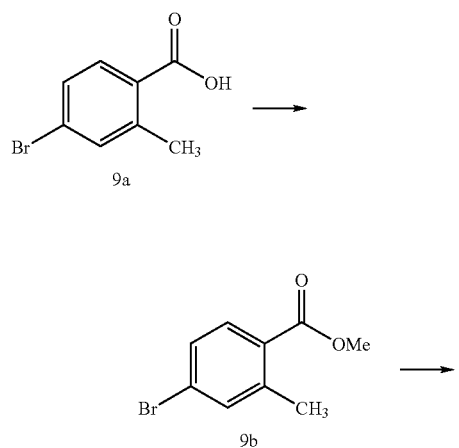

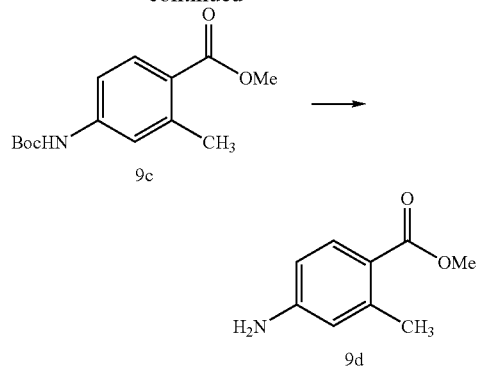

Step 1:
Compound 9b was synthesized in a manner similar to Example 30, Step 2. H¹ NMR (400 MHz, CDCl₃) δ 7.78 (d, 1H), 7.42 (s, 1H), 7.37 (d, 1H), 3.87 (s, 3H), 2.58 (s, 3H).

Step 2:
To a solution of aryl bromide 9b (1.00 g, 4.4 mmol) in THF (20 mL), was added t-butyl carbamate (0.61 g, 5.2 mmol), cesium carbonate (2.87 g, 8.8 mmol), Xantphos (8.38 g, 0.66 mmol). The solution was degassed with argon. To this solution, was added Pd(dba)₂Cl₂ and the resulting mixture was refluxed overnight, diluted with water and extracted twice with DCM. The combined organic phases was concentrated and purified by silica gel chromatography (DCM) to afford carbamate 9c (1.08 g, 93%). H¹ NMR (400 MHz, DMSO-d₆) δ 9.62 (s, 1H), 7.77 (d, 1H), 7.38 (m, 2H), 3.73 (s, 3H), 2.43 (s, 3H), 1.43 (s, 9H).

Step 3
Boc protected amine 9c (1.04 g, 3.9 mmol) was dissolved in 4 M hydrochloric acid in dioxane (10 mL) and stirred at rt fro 3 hours. The reaction was diluted slowly with a small amount of diethyl ether until a filterable solid formed. The solid was isolated through filtration and washed with diethyl ether to afford 9d as a light beige solid (HCl salt) (482 mg, 61%). H¹ NMR (400 MHz, DMSO-d₆) δ 8.01 (d, 1H), 7.25 (m, 2H), 3.88 (s, 3H), 2.61 (s, 3H).

Step 4
Compound 41 was prepared using a procedure similar to Example 30. MS found for $C_{23}H_{18}ClFN_4O_5S$ as (M-H)⁻ 515.0, 517.0.

Example 41

2-(5-chlorothiophen-2-yl)-2-(4-(6-fluoro-7-(methylamino)-2,4-dioxo-1,2-dihydroquinazolin-3(4H)-yl)-2-methoxybenzamido)acetic acid (Compound 42);

Compound 42 was synthesized using procedures similar to steps 1-3 of Example 40 and step 4 of Example 30 starting from methyl 4-amino-2-methoxybenzoate. MS found for Compound 42 as (M+H)+: 533.0.

Example 42

2-(2-chloro-4-(6-fluoro-7-(methylamino)-2,4-dioxo-1,2-dihydroquinazolin-3(4H)-yl)benzamido)-2-(5-chlorothiophen-2-yl)acetic acid (Compound 43);

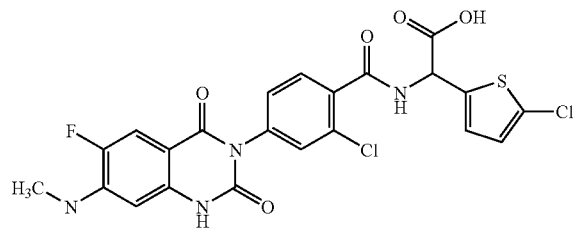

Compound 43 was synthesized starting from 4-bromo-2-chlorobenzoic acid using a procedure similar to Example 30. MS found for Compound 43 as (M+H)+: 537.0.

Example 43

2-(5-chlorothiophen-2-yl)-2-(2-fluoro-4-(6-fluoro-7-(methylamino)-2,4-dioxo-1,2-dihydroquinazolin-3(4H)-yl)benzamido)acetic acid (Compound 44);

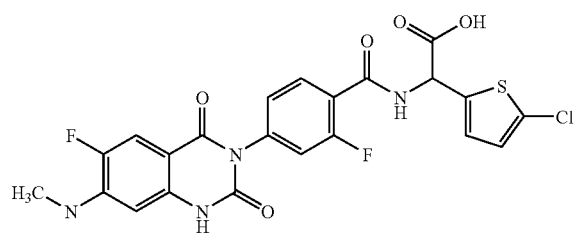

Compound 44 was synthesized starting from 4-bromo-2-fluorobenzoic acid using procedures similar to steps 1-3 of Example 40 and step 4 of Example 30. MS found for Compound 44 as (M+H)+: 521.0.

Example 44

N-((5-chlorothiophen-2-yl)(1H-tetrazol-5-yl)methyl)-4-(6-fluoro-7-(methylamino)-2,4-dioxo-1,2-dihydroquinazolin-3(4H)-yl)-3-methoxybenzamide (Compound 52);

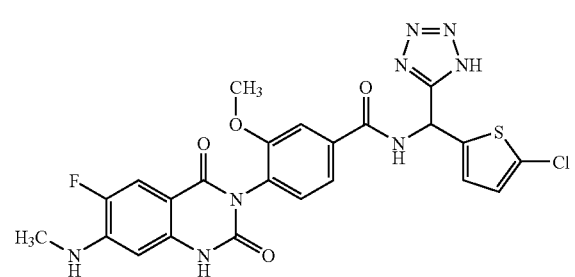

Compound 52 was prepared from the intermediate 8f in Example 30 and 5a in Example 11, using a procedure similar to that described in Example 11. MS found for Compound 52 as (M+H)+: 557.0.

Example 45

N-((5-chlorothiophen-2-yl)(5-oxo-4,5-dihydro-1,2,4-oxadiazol-3-yl)methyl)-4-(6-fluoro-7-(methylamino)-2,4-dioxo-1,2-dihydroquinazolin-3(4H)-yl)-3-methoxybenzamide (Compound 53);

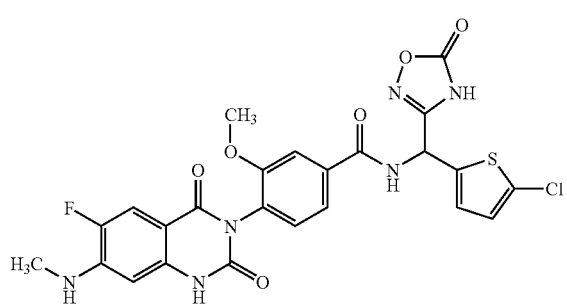

Compound 53 was prepared from the intermediate 8f in Example 30 using a procedure similar to that described in Example 25. (DMSO, 400 MHz): δ 9.26 (d, 1H), 7.55 (s, 1H), 7.48 (d, 1H), 7.30 (d, 1H), 7.21 (d, 1H), 6.86 (d, 2H), 6.73 (s, 1H), 6.17 (d, 1H), 6.08 (d, 1H), 3.70 (s, 3H), 2.72 (d, 3H). MS found for Compound 53 as (M+H)+: 573.0.

Example 46

2-(5-chlorothiophen-2-yl)-2-(3-(6-fluoro-7-(methylamino)-2,4-dioxo-1,2-dihydroquinazolin-3(4H)-yl)benzamido)acetic acid (Compound 111);

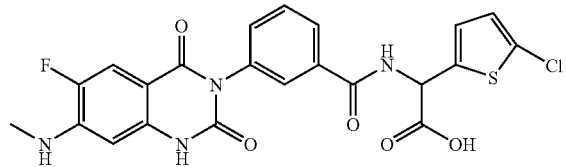

Compound III using procedures similar to steps 1-3 of Example 40 and step 4 of Example 30. (DMSO, 400 MHz): δ 8.28 (d, 1H), 7.73 (d, 1H), 7.53 (s, 1H), 7.47 (t, 1H), 7.25 (d, 1H), 7.19 (d, 1H), 6.80 (d, 1H), 6.68 (d, 1H), 6.05 (d, 1H), 6.00 (s, 1H), 5.04 (d, 1H), 2.77 (d, 3H). MS found for Compound III as (M+H)+: 503.0.

Example 47

Scheme 10

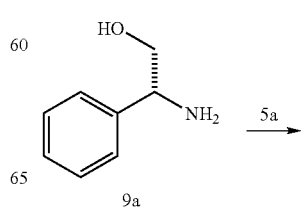

9a

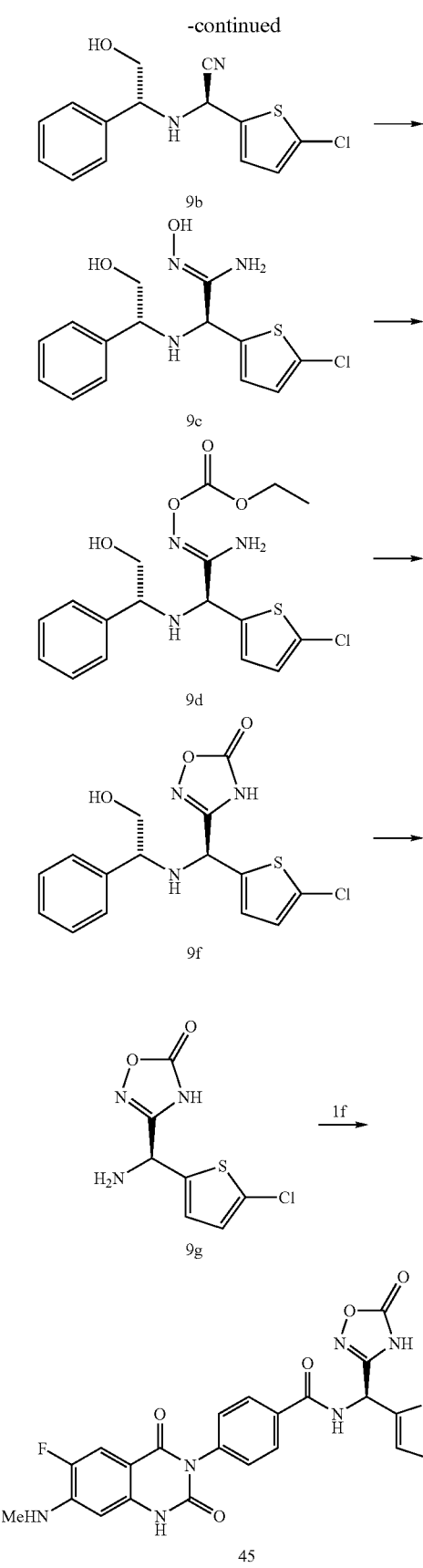

Step 1:

To a solution of (R)-phenylglycinol 9a (5.0 g, 34 mmol) and aldehyde 5a (5.6 g, 41 mmol) in methanol (70 mL) and water (20 mL), was added sodium bisulfite (4.3 g, 41 mmol) and potassium cyanide (2.7 g, 41 mmol). The resulting suspension was stirred until only a small amount of the imine remained. The mixture was concentrated in vacuo. DCM and water were added. The aqueous layer was extracted with DCM and the organic layer was concentrated in vacuo. The crude material was purified by silica gel chromatography (DCM) to afford 9b as a yellow oil (4.62 g, 46%) consisting of a 2:1 ratio of diastereomers. (DMSO, 400 MHz): δ 7.37 (m, 5H), 7.28 (m, 3H), 7.0 (m, 2.5H), 5.04 (t, 1H), 4.88 (t, 0.5H), 4.77 (d, 1H), 3.93 (m, 1H), 3.74 (m, 1.5H), 3.43 (m, 3H).

Step 2:

Nitrile 9b was converted to hydroxamidine 9c using a procedure similar to that described in Example 6, Step 1. The crude material was used for the next step without purification. MS found: $(M+H)^+$ 326.3, 328.0.

Step 3:

Hydroxamidine 9c was converted to carbonate 9d using a procedure similar to that described in Example 6, Step 2. MS found: $(M+H)^+$ 398.0, 400.0.

Step 4:

Carbonate 9d was converted to oxadiazolone 9f using a procedure similar to that described in Example 6, Step 3. At this stage the two diastereomers can be separated by preparative HPLC. MS found: $(M+H)^+$ 352.0, 354.0.

Step 5:

To a solution of oxadiazolone 9f (30 mg, 0.085 mmol) in DCM (6 mL) and methanol (3 mL) at 0° C., was added lead tetraacetate (38 mg, 0.085 mmol). The mixture was stirred for 5 min. The reaction mixture was concentrated and purified by prep HPLC to afford amine 9g as a white solid which was immediately used for the next step. MS found: $(M-H)^-$ 230.2, 232.0.

Step 6:

Compound 45 was prepared using a procedure similar to that described in Example 1, Step 10. The enantiomeric purity of the material was measured by chiral HPLC using an (R,R)-ULMO column (25 cm, ×4.6 mm, 5 um) from Regis Technologies eluting with 75/25 hexane/ethanol with 25 mM ammonium acetate and 1% triethyl amine and found to be greater than 90% ee. MS found for Compound 45 as $(M+H)^+$: 542.8.

Example 48

(R)-N-((5-chlorothiophen-2-yl)(5-oxo-4,5-dihydro-1,2,4-oxadiazol-3-yl)methyl)-4-(6-fluoro-7-(methylamino)-2,4-dioxo-1,2-dihydroquinazolin-3(4H)-yl)benzamide (Compound 46);

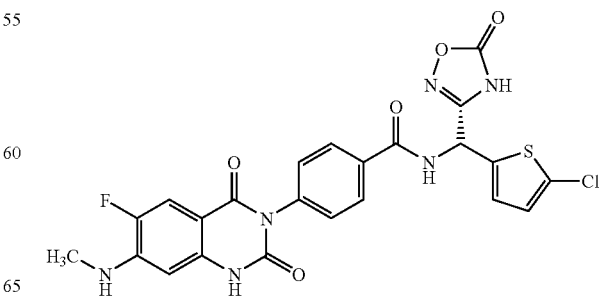

Compound 46 was prepared using a procedure similar to that described for Example 47, starting with (S)-phenylglycinol. MS found: (M−H)⁻ 541.0, 543.0. Chiral purity using above conditions was found to be greater than 90% ee.

Example 49

2-(5-chlorothiophen-2-yl)-2-(4-(7-fluoro-6-(methylamino)-2,4-dioxo-1,2-dihydroquinazolin-3(4H)-yl) benzamido)acetic acid 48

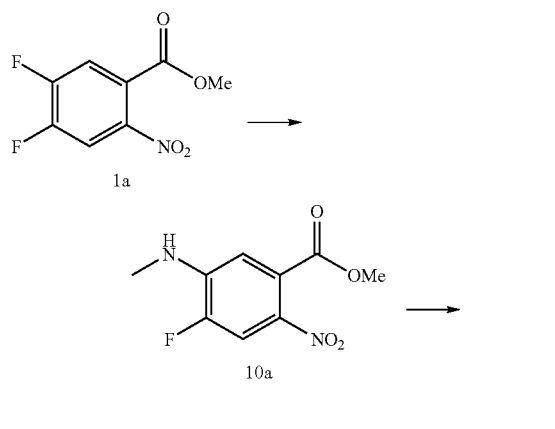

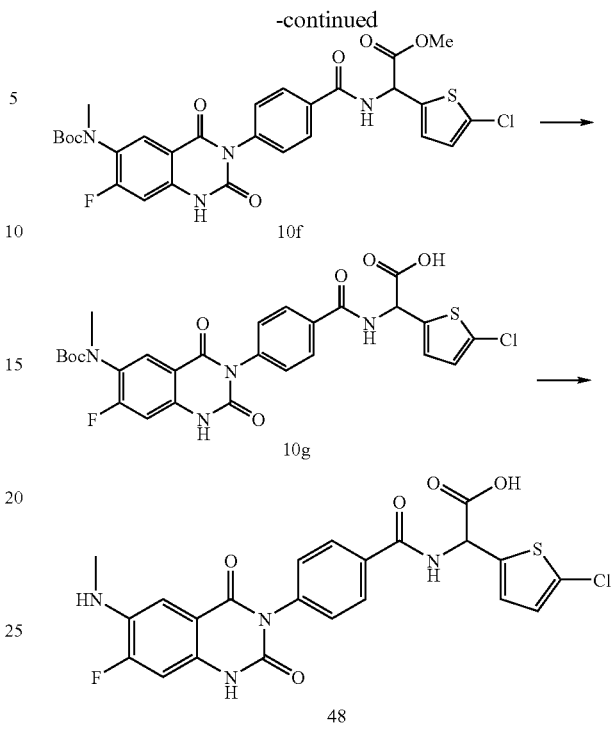

Step 1:

To a solution of difluoroarene 1a (3.0 g, 14 mmol) in DMF (5 mL), was added methyl amine (2 M in THF, 24 mL, 48 mmol). The mixture was stirred at rt until the completion of the reaction. The mixture was diluted with water and extracted twice with ethyl acetate. The combined organic layers were dried over magnesium sulfate, filtered, and concentrated in vacuo to afford 10a as a red oil which was used immediately for the next step. (DMSO, 400 MHz): δ 7.91 (d, 1H), 7.39 (s, 1H), 6.79 (d, 1H), 3.83 (s, 3H), 2.83 (d, 3H).

Step 2:

To a solution of 10a in acetonitrile (20 mL), was added t-butyl pyrocarbonate (3.3 g, 15 mmol) and N,N-dimethylaminopyridine (0.68 g, 5.6 mmol). The mixture was stirred for a few minutes, diluted with water and extracted twice with DCM. The combined organic layer was dried over magnesium sulfate, filtered, and concentrated to afford carbamate, 10b as thick yellow syrup. (4.2 g, 91% for two steps). (DMSO, 400 MHz): δ 8.17 (d, 1H), 7.96 (d, 1H), 3.83 (s, 3H), 3.17 (s, 3H), 1.36 (s, 9H).

Step 3:

To a solution of nitroarene 10b (4.2 g, 12.8 mmol) in methanol (70 mL), was added palladium on carbon (Degussa, 10%, ca. 1.0 g). The mixture was purged and placed under an atmosphere of hydrogen. It was stirred overnight, then purged with argon, and filtered through a short pad of celite. The filtrate was concentrated to afford aniline 10c as a colorless glass which was used for the next step. (DMSO, 400 MHz): δ 7.59 (d, 1H), 6.85 (s, 2H), 6.57 (d, 1H), 3.77 (s, 3H), 3.01 (s, 3H), 1.24 (s, 9H).

Step 4:

To a solution of aniline 10c (12.8 mmol based on theoretical) in DCM (50 mL), was added DIPEA (2.4 mL, 5.1 mmol), followed by methyl 4-isocyanatobenzoate (2.50 g, 14.1 mmol). The resulting mixture was stirred over the weekend during which time a precipitate formed. The crude reaction mixture was filtered and both the solid and filtrate contained the desired product plus small amounts of impurities. The filtrate was then concentrated and purified by silica gel chromatography (0-10% ethyl acetate/DCM) to afford desired product 10d as a colorless oil (1.2 g, 21%). MS found: (M–H)⁻ 442.3.

Step 5:

Compound 10e was synthesized in a manner similar to Example 1, Step 5. MS found: (M–H)⁻ 428.3.

Step 6:

Compound 10f was synthesized in a manner similar to Example 1, Step 6. (DMSO, 400 MHz): δ 11.73 (s, 1H), 9.58 (d, 1H), 7.97 (d, 2H), 7.91 (d, 1H), 7.43 (d, 2H), 7.03 (m, 3H), 5.83 (d, 1H), 3.70 (s, 3H), 3.12 (s, 3H), 1.34 (s, 9H).

Step 7:

Compound 10g was synthesized in a manner similar to Example 1, Step 5 and was used immediately for the next step.

Step 8:

To a solution of carbamate 10g (135 mg, 0.22 mmol) in DCM (9 mL), was added trifluoroacetic acid (1 mL). The mixture was stirred at rt for 2 hours, then concentrated and the crude product was purified by HPLC to afford 48 as a white solid (85 mg, 76%). MS found: (M–H)⁻ 501.2, 503.0.

Example 50

N-((5-chlorothiophen-2-yl)(1H-tetrazol-5-yl)methyl)-4-(7-fluoro-6-(methylamino)-2,4-dioxo-1,2-dihydroquinazolin-3(4H)-yl)benzamide (Compound 49);

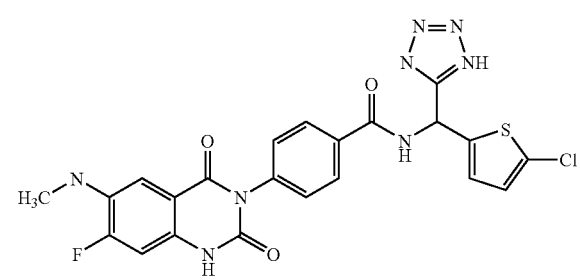

Compound 49 was synthesized in a manner similar to Example 11 using intermediate 10e. MS found for Compound 49 as (M+H)⁺: 527.2.

Example 51

N-((5-chlorothiophen-2-yl)(5-oxo-4,5-dihydro-1,2,4-oxadiazol-3-yl)methyl)-4-(7-fluoro-6-(methylamino)-2,4-dioxo-1,2-dihydroquinazolin-3(4H)-yl)benzamide (Compound 50);

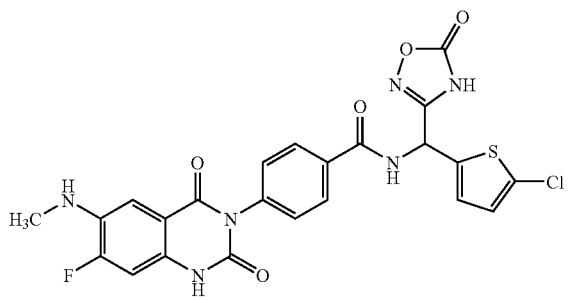

Compound 50 was synthesized in a manner similar to Example 25 using intermediate 10e from Example 49. MS found for Compound 50 as (M+H)⁺: 543.0.

Example 52

N-((1H-tetrazol-5-yl(3-(trifluoromethyl)phenyl)methyl)-4-(6-fluoro-7-(methylamino)-2,4-dioxo-1,2-dihydroquinazolin-3(4H)-yl)benzamide (Compound 34)

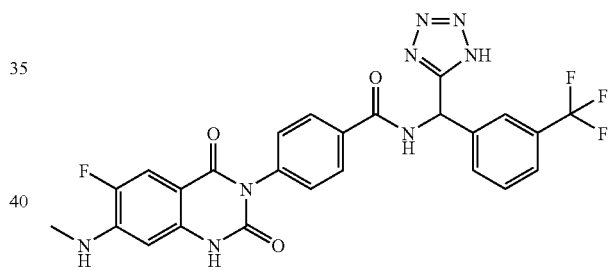

The titled compound was made by the procedure similar to that described for Example 12. (DMSO, 400 MHz): δ 9.25 (d, 1H), 7.88 (d, 2H), 7.72 (s, 1H), 7.67 (d, 1H), 7.50 (d, 1H), 7.42 (d, 1H), 7.34 (s, 1H), 7.24 (d, 2H), 6.70 (s, 1H), 6.48 (d, 1H), 6.17 (d, 1H), 2.68 (d, 3H). MS found for Compound 34 as (M+H)⁺: 555.0.

Example 53

2-(5-chlorothiophen-2-yl)-2-(3-(4-(6-fluoro-7-(methylamino)-2,4-dioxo-1,2-dihydroquinazolin-3(4H)-yl)phenyl)ureido)acetic acid (Compound 110)

Scheme 11

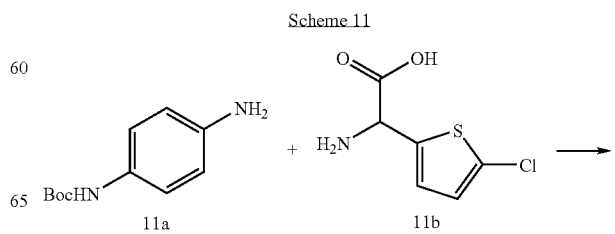

-continued

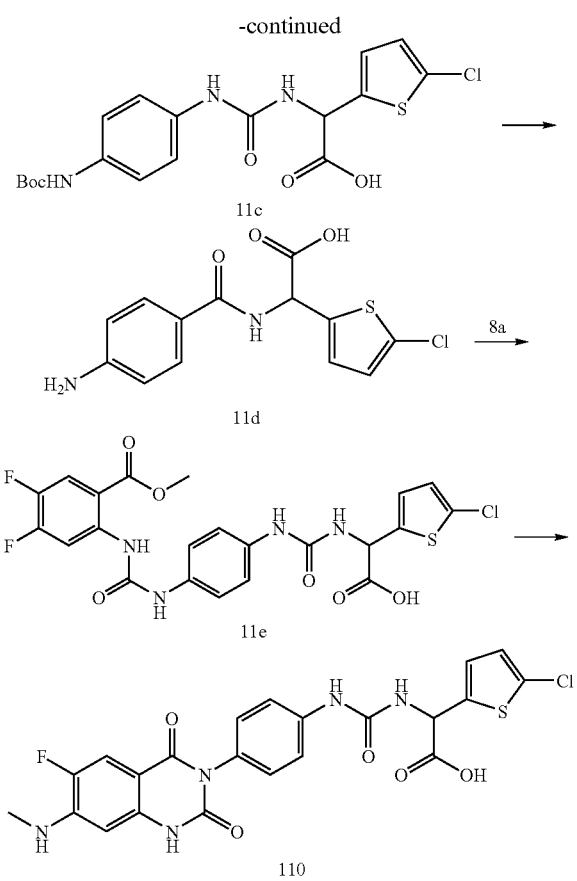

Step 1:
To a solution of aniline 11a (336 mg, 1.62 mmol) in DCM (10 mL), was added DIPEA (1.97 mL, 11.34 mmol). This solution was added to a solution of phosgene (2 M in toluene, 2.43 mL, 4.86 mmol) in an ice bath. Upon complete addition the ice bath was removed and the reaction checked by HPLC which showed the formation of the reactive intermediate. The crude reaction mixture was concentrated, resuspended in DCM (10 mL), and the mixture was added to a solution containing amino acid 11b (238 mg, 1.25 mmol) and DIPEA (0.43 mg, 2.5 mmol) in 15 mL of DMF. The reaction was stirred over the weekend at room temperature, diluted with water and acidified with 1 M HCl to pH=2. The aqueous layer was extracted twice with ethyl acetate. The combined organic layer was concentrated and purified by silica gel chromatography (0-10% methanol/DCM) to afford 11c as a light red oil containing a small amount of DMF. MS found: (M–H)⁻ 424.0, 426.2.

Step 2:
Compound 11d was synthesized in a similar manner to Example 49, Step 8. MS found: (M+H)⁺ 326.0, 328.0.

Step 3:
Compound 11e was synthesized in a similar manner to Example 29, Step 4 using DMF as solvent. MS found for $C_{22}H_{17}ClF_2N_4O_6S$ as (M–H)⁻ 537.3, 539.0.

Step 4:
Compound 110 was prepared in a manner similar to Example 1, Step 4. MS found: (M–H)⁻ 516.0, 518.0.

Examples 54-122

N-((5-chlorothiophen-2-yl)methyl)-4-(7-(4-fluorobenzylamino)-2,4-dioxo-1,2-dihydroquinazolin-3(4H)-yl)benzamide (Compound 1);

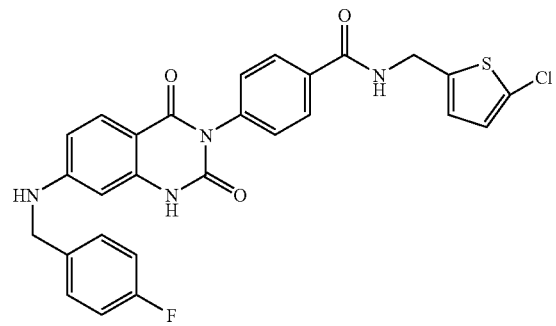

was prepared in a manner similar to Examples above. MS found: (M–H)⁻ 535.0.

2-(4-(7-(4-fluorobenzylamino)-2,4-dioxo-1,2-dihydroquinazolin-3(4H)-yl)benzamido)-2-(thiophen-2-yl)acetic acid (Compound 2);

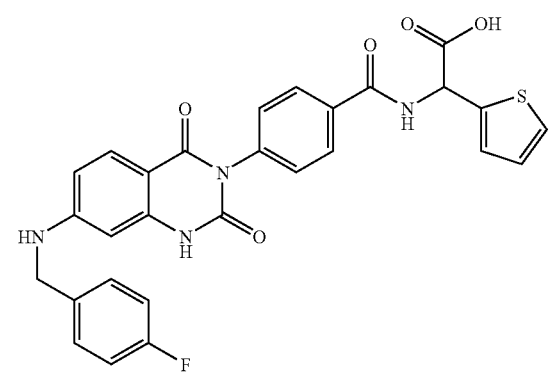

was prepared in a manner similar to Examples above. MS found: (M–H)⁻ 545.0.

2-(4-(7-(4-fluorobenzylamino)-2,4-dioxo-1,2-dihydroquinazolin-3(4H)-yl)benzamido)-3-(thiophen-2-yl)propanoic acid (Compound 3);

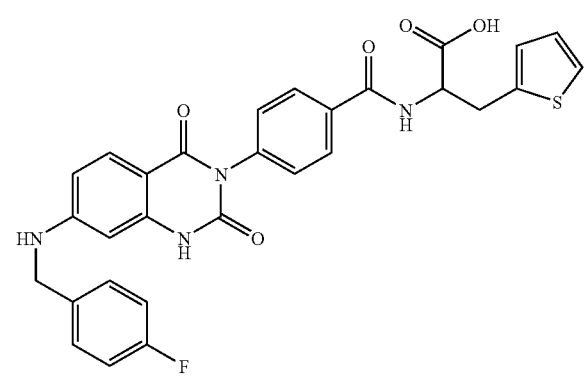

was prepared in a manner similar to Examples above. MS found: (M–H)⁻ 559.0.

2-(4-(6-fluoro-7-(methylamino)-2,4-dioxo-1,2-dihydroquinazolin-3(4H)-yl)benzamido)-2-(thiophen-2-yl)acetic acid (Compound 8);

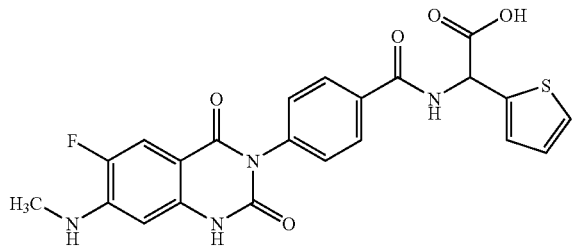

was prepared in a manner similar to Examples above. MS found: (M–H)⁻ 470.0.

2-(4-(6-fluoro-7-(methylamino)-2,4-dioxo-1,2-dihydroquinazolin-3(4H)-yl)benzamido)-3-(thiophen-2-yl)propanoic acid (Compound 9);

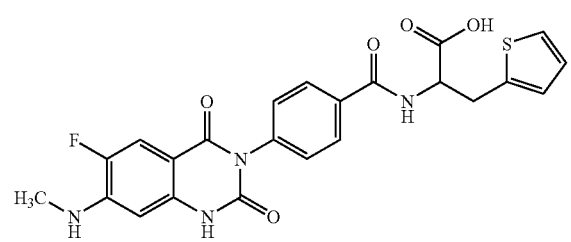

was prepared in a manner similar to Examples above. MS found: (M–H)⁻ 483.0.

N-((1H-tetrazol-5-yl)methyl)-4-(7-(4-fluorobenzylamino)-2,4-dioxo-1,2-dihydroquinazolin-3(4H)-yl)benzamide (Compound 10)

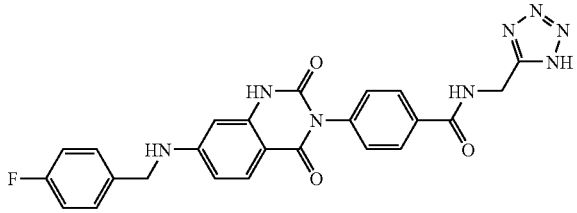

was prepared in a manner similar to Examples above. MS found: (M–H)⁻ 487.0.

2-(5-chlorothiophen-2-yl)-2-(4-(6-fluoro-7-(methylamino)-2,4-dioxo-1,2-dihydroquinazolin-3(4H)-yl)benzamido)acetic acid (Compound 13);

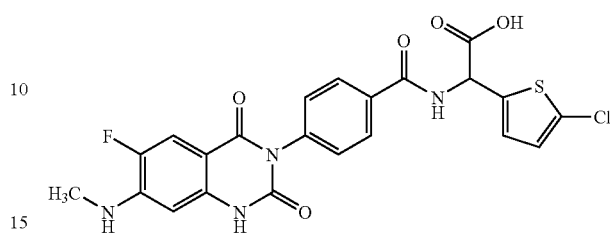

was prepared in a manner similar to Examples above. MS found: (M–H)⁻ 503.0.

2-(4-chlorophenyl)-2-(4-(6-fluoro-7-(methylamino)-2,4-dioxo-1,2-dihydroquinazolin-3(4H)-yl)benzamido)acetic acid (Compound 14);

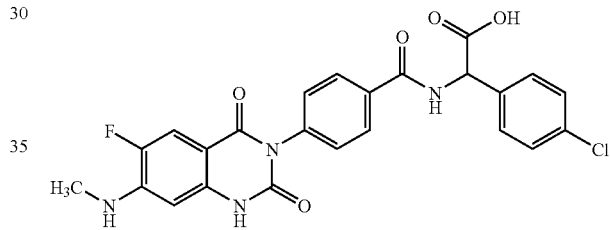

was prepared in a manner similar to Examples above. MS found: (M–H)⁻ 497.0.

methyl 2-(5-chlorothiophen-2-yl)-2-(4-(6-fluoro-7-(methylamino)-4-oxo-2H-benzo[e][1,3]oxazin-3(4H)-yl)benzamido)acetate (Compound 18);

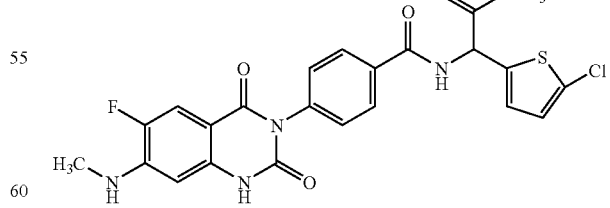

was prepared in a manner similar to Examples above. MS found: (M–H)⁻ 517.0.

2-(5-chlorothiophen-2-yl)-2-(4-(7-(methylamino)-2,
4-dioxo-1,2-dihydroquinazolin-3(4H)-yl)benzamido)
acetic acid (Compound 20);

2-morpholinoethyl 2-(5-chlorothiophen-2-yl)-2-(4-
(6-fluoro-7-(methylamino)-2,4-dioxo-1,2-dihydro-
quinazolin-3(4H)-yl)benzamido)acetate (Compound
35);

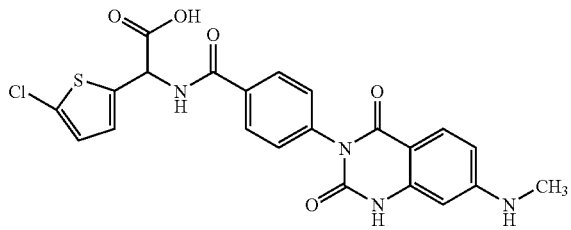

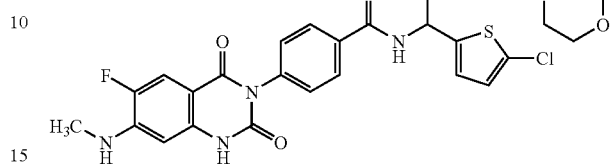

was prepared in a manner similar to Examples above. MS found: (M−H)⁻ 485.0.

was prepared in a manner similar to Examples above. MS found: (M−H)⁻ 617.0.

ethyl 2-(5-chlorothiophen-2-yl)-2-(4-(6-fluoro-7-
(methylamino)-2,4-dioxo-1,2-dihydroquinazolin-3
(4H)-yl)benzamido)acetate (Compound 26);

N-(1-(5-chlorothiophen-2-yl)-2-hydroxyethyl-4-(6-
fluoro-7-(methylamino)-2,4-dioxo-1,2-dihydro-
quinazolin-3(4H)-yl)benzamide (Compound 36);

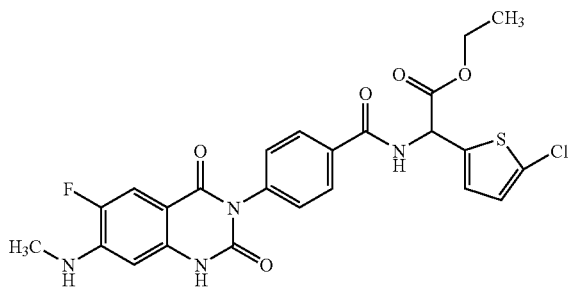

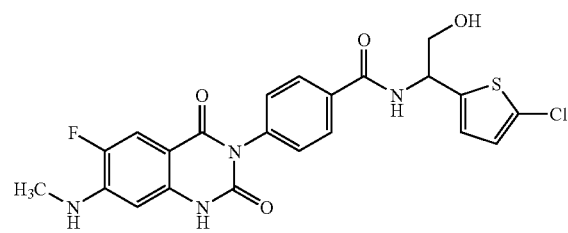

was prepared in a manner similar to Examples above. MS found: (M−H)⁻ 489.0.

was prepared in a manner similar to Examples above. MS found: (M−H)⁻ 531.0.

2-(5-chlorothiophen-2-yl)-2-(4-(6-iodo-2,4-dioxo-1,
2-dihydroquinazolin-3(4H)-yl)benzamido)acetic acid
(Compound 37);

2-(5-chlorothiophen-2-yl)-2-(4-(2,4-dioxo-1,2-dihy-
droquinazolin-3(4H)-yl)benzamido)acetic acid
(Compound 33);

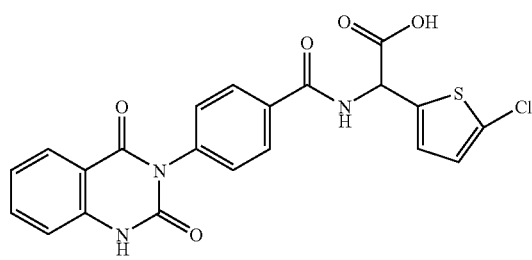

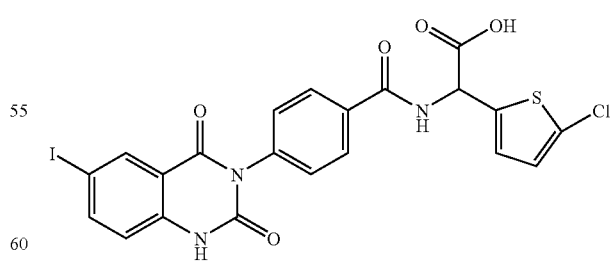

was prepared in a manner similar to Examples above. MS found: (M−H)⁻ 456.0.

was prepared in a manner similar to Examples above. MS found: (M−H)⁻ 581.7.

2-(5-chlorothiophen-2-yl)-2-(4-(6-isopropoxy-2,4-dioxo-1,2-dihydroquinazolin-3(4H)-yl)benzamido)acetic acid (Compound 38);

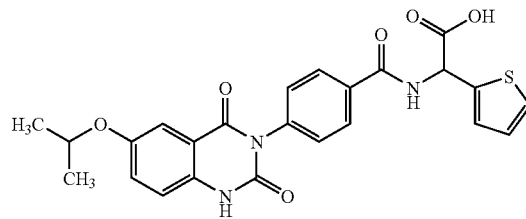

was prepared in a manner similar to Examples above. MS found: (M–H)⁻ 515.0.

2-(5-chlorothiophen-2-yl)-2-(4-(2,4-dioxo-1,2-dihydroquinazolin-3(4H)-yl)benzamido)acetic acid (Compound 39);

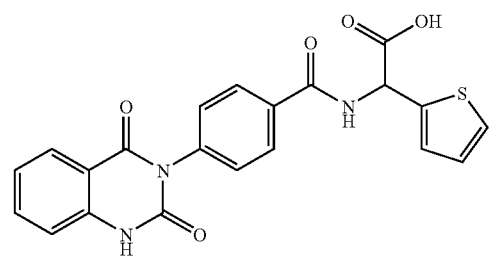

was prepared in a manner similar to Examples above. MS found: (M–H)⁻ 422.0.

N-(2-amino-1-(5-chlorothiophen-2-yl)-2-oxoethyl)-4-(6-fluoro-7-(methylamino)-2,4-dioxo-1,2-dihydroquinazolin-3(4H)-yl)benzamide (Compound 47);

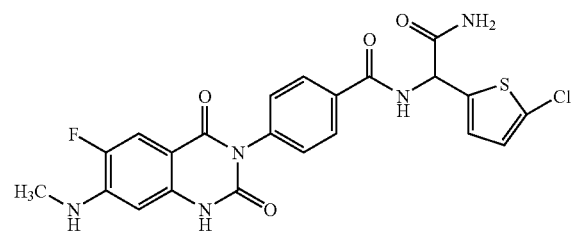

was prepared in a manner similar to Examples above. MS found: (M–H)⁻ 502.0.

(S)-2-(5-chlorothiophen-2-yl)-2-(4-(6-fluoro-7-(methylamino)-4-oxo-2H-benzo[e][1,3]oxazin-3(4H)-yl)benzaamido)acetic acid (Compound 62);

was prepared in a manner similar to Examples above. MS found: (M–H)⁻ 490.0.

methyl 2-(5-chlorothiophen-2-yl)-2-(4-(6-fluoro-7-(methylamino)-4-oxo-2H-benzo[e][1,3]oxazin-3(4H)-yl)benzamido)acetate (Compound 66);

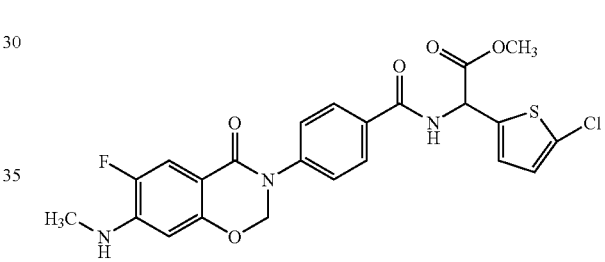

was prepared in a manner similar to Examples above. MS found: (M–H)⁻ 504.0.

ethyl 2-(5-chlorothiophen-2-yl)-2-(4-(6-fluoro-7-(methylamino)-4-oxo-2H-benzo[e][1,3]oxazin-3(4H)-yl)benzamido)acetate (Compound 67);

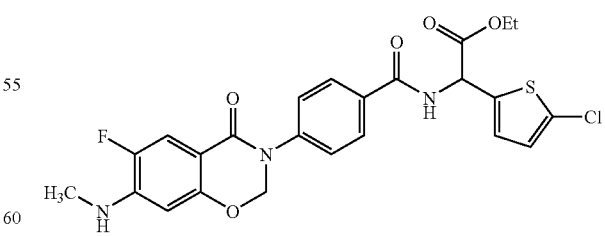

was prepared in a manner similar to Examples above. MS found: (M–H)⁻ 518.0.

2-(5-chlorothiophen-2-yl)-2-(4-(8-methoxy-4-oxo-
2H-benzo[e][1,3]oxazin-3(4H)-yl)benzamido)acetic
acid (Compound 68);

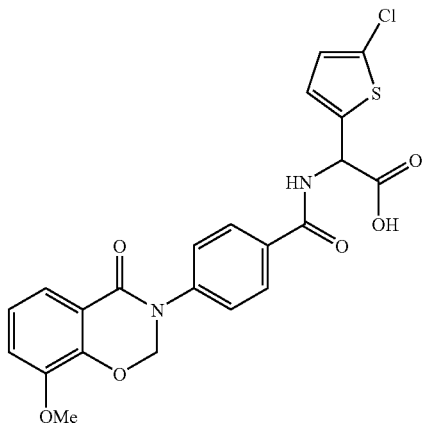

was prepared in a manner similar to Examples above. MS found: (M–H)⁻ 473.0.

2-(5-chlorothiophen-2-yl)-2-(4-(7-methyl-4-oxo-2H-
benzo[e][1,3]oxazin-3(4H)-yl)benzamido)acetic acid
(Compound 69);

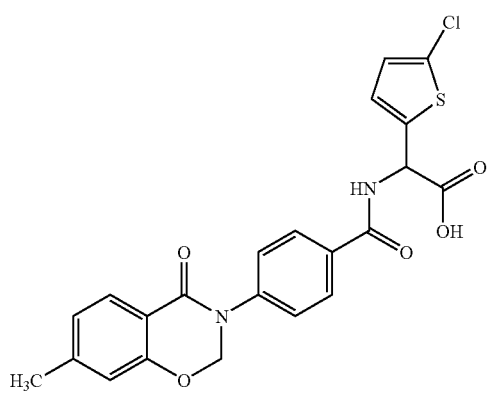

was prepared in a manner similar to Examples above. MS found: (M–H)⁻ 457.0.

N-(2-amino-1-(5-chlorothiophen-2-yl)-2-oxoethyl)-
4-(6-fluoro-7-(methylamino-4-oxo-2H-benzo[e][1,3]
oxazin-3(4H)-yl)benzamide (Compound 70);

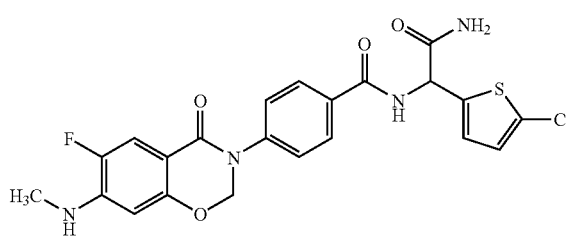

was prepared in a manner similar to Examples above. MS found: (M–H)⁻ 489.0.

2-(5-chlorothiophen-2-yl)-2-(4-(6-ethyl-4-oxo-2H-
benzo[e][1,3]oxazin-3(4H)-yl)benzamido)acetic acid
(Compound 72);

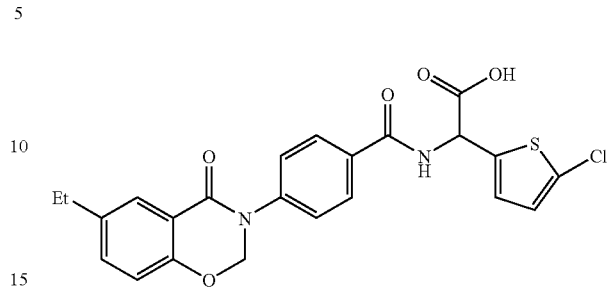

was prepared in a manner similar to Examples above. MS found: (M–H)⁻ 471.0.

N-((5-chlorothiophen-2-yl)(1-methyl-1H-tetrazol-5-
yl)methyl)-4-(6-fluoro-7-(methylamino)-4-oxo-2H-
benzo[e][1,3]oxazin-3(4H)-yl)benzamide (Compound 73);

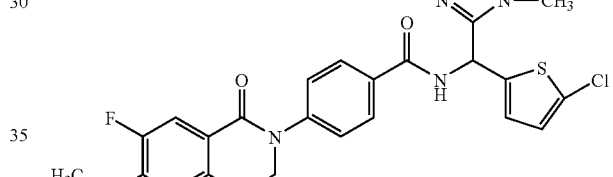

was prepared in a manner similar to Examples above. MS found: (M–H)⁻ 528.0.

N-((5-chlorothiophen-2-yl)(2-methyl-2H-tetrazol-5-
yl)methyl)-4-(6-fluoro-7-(methylamino)-4-oxo-2H-
benzo[e][1,3]oxazin-3(4H)-yl)benzamide (Compound 74);

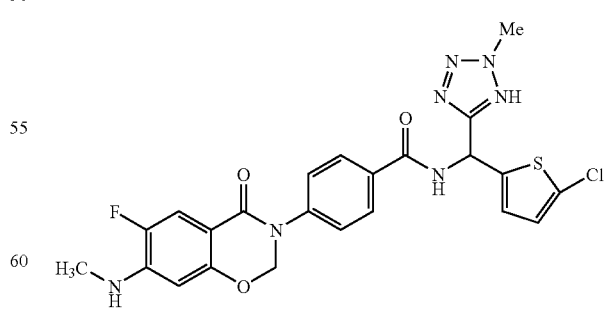

was prepared in a manner similar to Examples above. MS found: (M–H)⁻ 528.0.

methyl 2-(5-chlorothiophen-2-yl)-2-(4-(6-methyl-4-oxo-2H-benzo[e][1,3]oxazin-3(4H)-yl)benzamido)acetate (Compound 76);

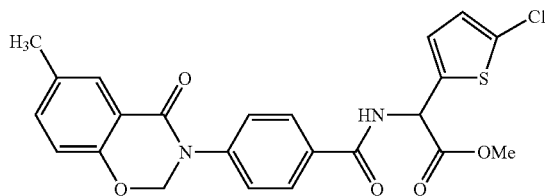

was prepared in a manner similar to Examples above. MS found: (M–H)⁻ 471.0.

2-(5-chlorothiophen-2-yl)-2-(4-(6-methyl-4-oxo-2H-benzo[e][1,3]oxazin-3(4H)-yl)benzamido)acetic acid (Compound 77);

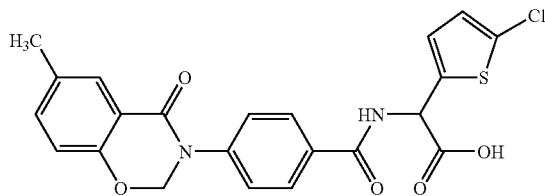

was prepared in a manner similar to Examples above. MS found: (M–H)⁻ 457.0.

2-(5-chlorothiophen-2-yl)-2-(4-(7-ethyl-4-oxo-2H-benzo[e][1,3]oxazin-3(4H)-yl)benzamido)acetic acid (Compound 78);

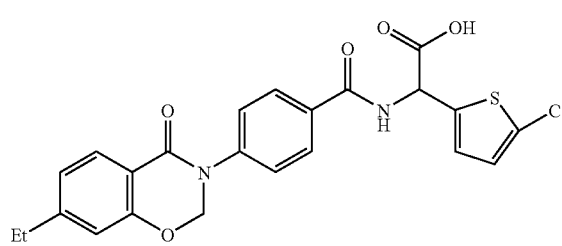

was prepared in a manner similar to Examples above. MS found: (M–H)⁻ 471.0.

N-((3-chlorophenyl)(1H-tetrazol-5-yl)methyl)-4-(6-fluoro-7-(methylamino)-4-oxo-2H-benzo[e][1,3]oxazin-3(4H)-yl)benzamide (Compound 80);

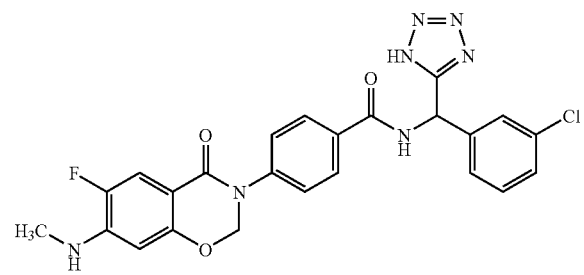

was prepared in a manner similar to Examples above. MS found: (M–H)⁻ 508.0.

N-((5-chlorothiophen-2-yl)(thiazol-2-yl)methyl)-4-(6-fluoro-7-(methylamino)-4-oxo-2H-benzo[e][1,3]oxazin-3(4H)-yl)benzamide (Compound 82);

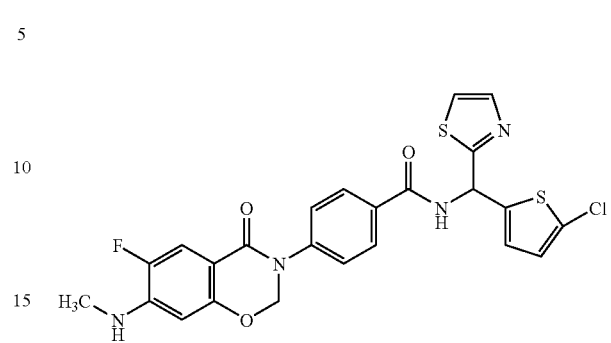

was prepared in a manner similar to Examples above. MS found: (M–H)⁻ 529.0.

2-(5-chlorothiophen-2-yl)-2-(4-(4-oxo-2H-benzo[e][31]oxazin-3(4H)-yl)benzamido)acetic acid (Compound 83);

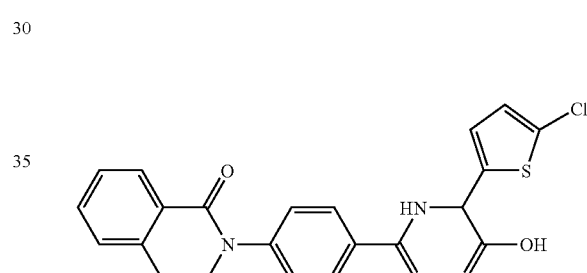

was prepared in a manner similar to Examples above. MS found: (M–H)⁻ 443.0.

2-(5-chlorothiophen-2-yl)-2-(4-(7-(4-fluorobenzylamino)-4-oxo-2H-benzo[e][1,3]oxazin-3(4H)-yl)benzamido)acetic acid (Compound 84);

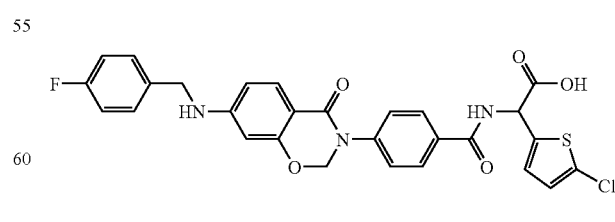

was prepared in a manner similar to Examples above. MS found: (M–H)⁻ 566.0.

N-((5-chlorothiophen-2-yl)(4-methylthiazol-2-yl)methyl)-4-(6-fluoro-7-(methylamino)-4-oxo-2H-benzo[e][1,3]oxazin-3(4H)-yl)benzamide (Compound 85);

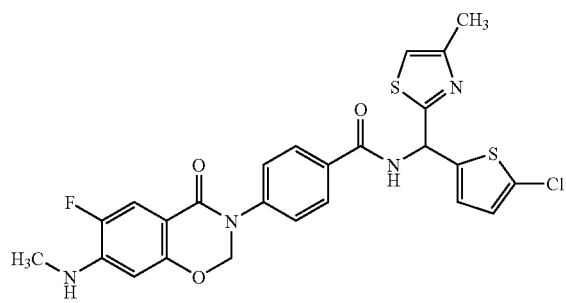

was prepared in a manner similar to Examples above. MS found: (M–H)⁻ 544.0.

N-((5-chlorothiophen-2-yl)(1H-tetrazol-5-yl)methyl)-4-(6-fluoro-7-(methylamino)-4-oxo-2H-benzo[e][1,3]oxazin-3(4H)-yl)benzamide (Compound 87);

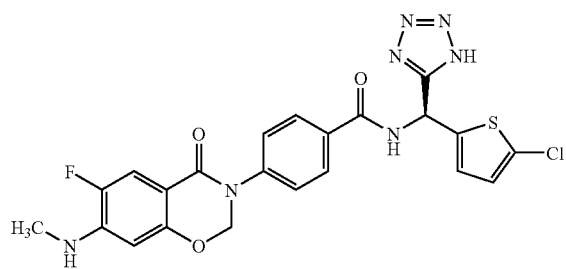

was prepared in a manner similar to Examples above. MS found: (M–H)⁻ 514.0.

(S)-N-((5-chlorothiophen-2-yl)(5-oxo-4,5-dihydro-1,2,4-oxadiazol-3-yl)methyl)-4-(6-fluoro-7-(methylamino)-4-oxo-2H-benzo[e][1,3]oxazin-3(4H)-yl)benzamide (Compound 88);

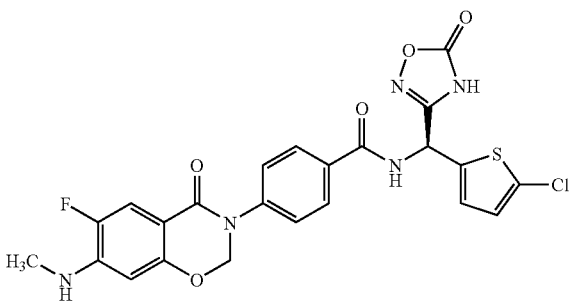

was prepared in a manner similar to Examples above. MS found: (M–H)⁻ 530.0.

(R)-N-((5-chlorothiophen-2-yl)(1H-tetrazol-5-yl)methyl)-4-(6-fluoro-7-(methylamino)-4-oxo-2H-benzo[e][1,3]oxazin-3(4H)-yl)benzamide (Compound 89);

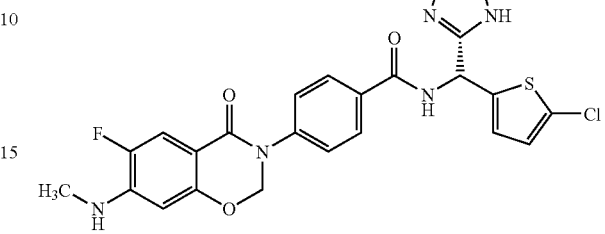

was prepared in a manner similar to Examples above. MS found: (M–H)⁻ 514.0.

2-(5-chlorothiophen-2-yl)-2-(4-(7-fluoro-6-(methylamino)-1-oxoisoquinolin-2(1H)-yl)benzamido)acetic acid (Compound 90);

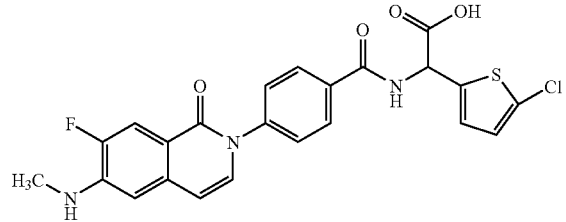

was prepared in a manner similar to Examples above. MS found: (M–H)⁻ 486.0.

N-((5-chlorothiophen-2-yl)(1H-tetrazol-5-yl)methyl)-4-(7-fluoro-6-(methylamino)-1-oxoisoquinolin-2(1H)-yl)benzamide (Compound 91);

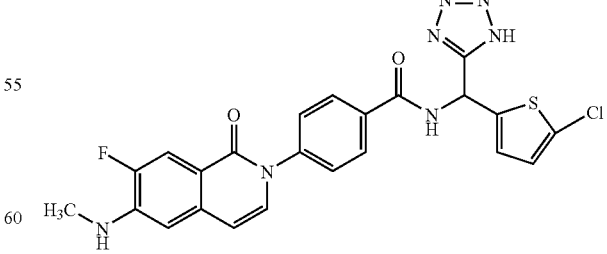

was prepared in a manner similar to Examples above. MS found: (M–H)⁻ 510.0.

2-(5-chlorothiophen-2-yl)-2-(4-(7-fluoro-6-methoxy-
1-oxoisoquinolin-2(1H)-yl)benzamido)acetic acid
(Compound 92);

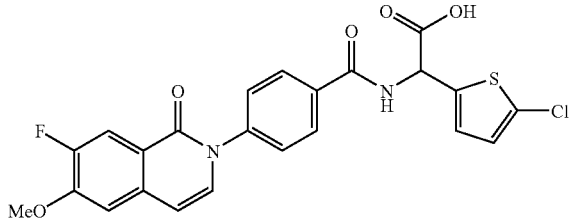

was prepared in a manner similar to Examples above. MS found: (M–H)⁻ 487.0.

2-(5-chlorothiophen-2-yl)-2-(4-(6-ethyl-1-oxoiso-
quinolin-2(1H)-yl)benzamido)acetic acid (Com-
pound 93);

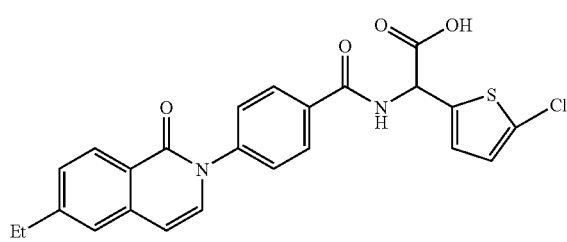

was prepared in a manner similar to Examples above. MS found: (M–H)⁻ 467.0.

2-(4-(6-carbamoyl-1-oxoisoquinolin-2(1H)-yl)ben-
zamido)-2-(5-chlorothiophen-2-yl)acetic acid (Com-
pound 94);

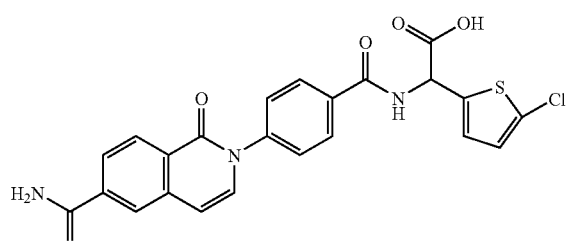

was prepared in a manner similar to Examples above. MS found: (M–H)⁻ 482.0.

2-(5-chlorothiophen-2-yl)-2-(4-(6-cyano-1-oxoiso-
quinolin-2(1H)-yl)benzamido)acetic acid (Com-
pound 95);

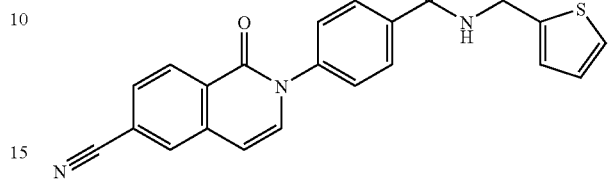

was prepared in a manner similar to Examples above. MS found: (M–H)⁻ 430.0.

2-(5-chlorothiophen-2-yl)-2-(4-(1-oxoisoquinolin-2
(1H)-yl)benzamido)acetic acid (Compound 96);

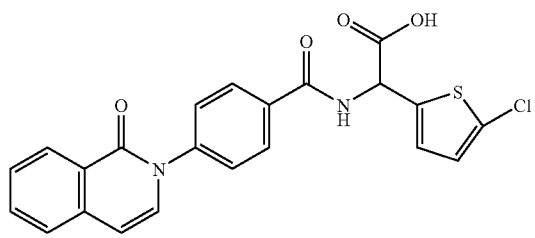

was prepared in a manner similar to Examples above. MS found: (M–H)⁻ 439.0.

2-(4-(1-oxoisoquinolin-2(1H)-yl)benzamido)-2-
(thiophen-2-yl)acetic acid (Compound 97);

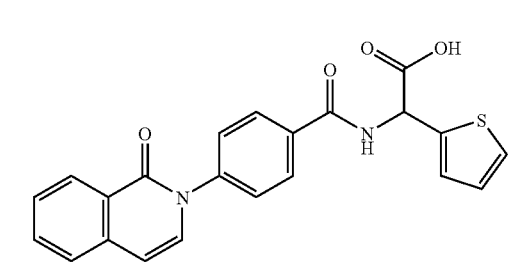

was prepared in a manner similar to Examples above. MS found: (M–H)⁻ 405.0.

2-(5-chlorothiophen-2-yl)-2-(4-(6-cyano-1-oxoiso-
quinolin-2(1H)-yl)benzamido) acetic acid (Com-
pound 98);

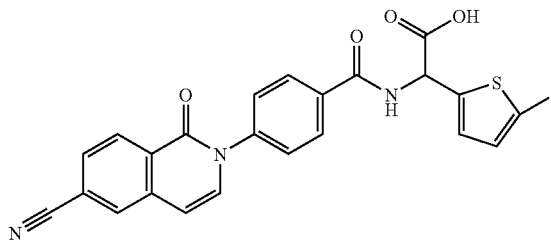

was prepared in a manner similar to Examples above. MS found: (M–H)⁻ 464.0.

4-(4-carbamoyl-1-oxoisoquinolin-2(1H)-yl)benza-
mido)-2-(5-chlorothiophen-2-yl)acetic acid (Com-
pound 99);

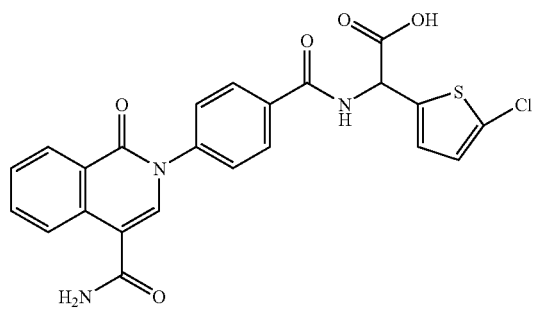

was prepared in a manner similar to Examples above. MS found: (M–H)⁻ 482.0.

2-(5-chlorothiophen-2-yl)-2-(4-(4-cyano-1-oxoiso-
quinolin-2(1H)-yl)benzamido)acetic acid (Com-
pound 100);

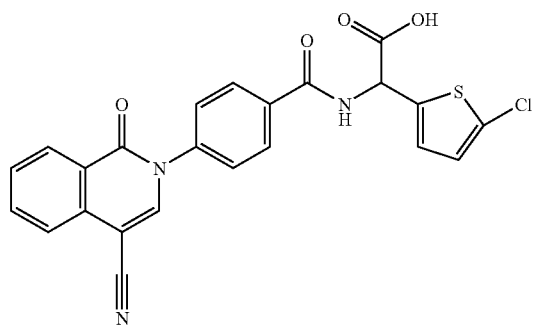

was prepared in a manner similar to Examples above. MS found: (M–H)⁻ 464.0.

2-(5-chlorothiophen-2-yl)-2-(4-(6-methoxy-1-ox-
oisoquinolin-2(1H)-yl)benzamido)acetic acid (Com-
pound 101);

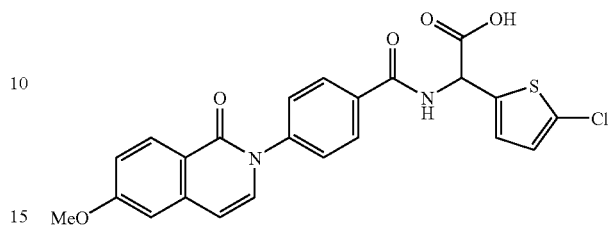

was prepared in a manner similar to Examples above. MS found: (M–H)⁻ 469.0.

2-(4-(4-bromo-1-oxoisoquinolin-2(1H)-yl)benza-
mido)-2-(5-chlorothiophen-2-yl)acetic acid (Com-
pound 102);

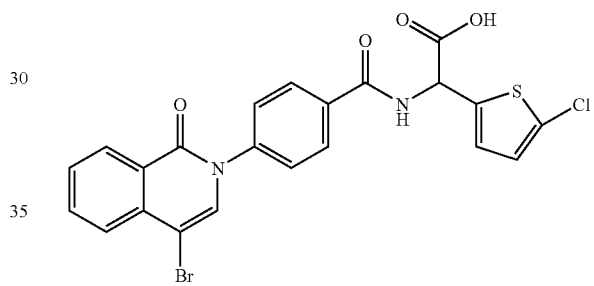

was prepared in a manner similar to Examples above. MS found: (M–H)⁻ 518.0.

2-(5-chloro-N-(4-(6-fluoro-7-(methylamino)-2,4-
dioxo-1,2-dihydroquinazolin-3(4H)-yl)benzyl)
thiophene-2-carboxamido)acetic acid (Compound
103);

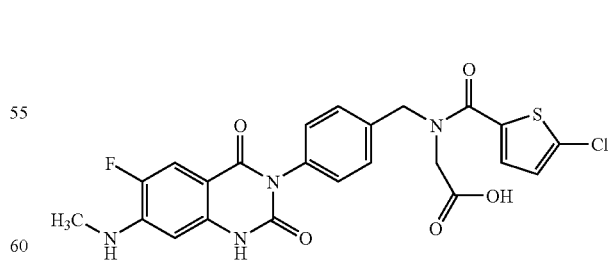

was prepared in a manner similar to Examples above. MS found: (M–H)⁻ 517.0.

3-(5-chlorothiophen-2-yl)-3-(4-(6-fluoro-7-(methylamino)-2,4-dioxo-1,2-dihydroquinazolin-3(4H)-yl)benzylamino)propanoic acid (Compound 104);

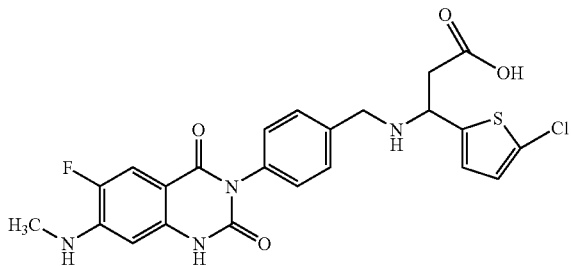

was prepared in a manner similar to Examples above. MS found: (M–H)⁻ 503.0.

2-(5-chlorothiophen-2-yl)-2-(4-(6-fluoro-7-(methylamino)-4-oxo-2H-benzo[e][1,3]oxazin-3(4H)-yl)benzylamino)acetic acid (Compound 105);

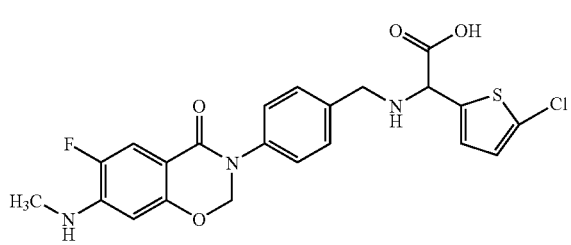

was prepared in a manner similar to Examples above. MS found: (M–H)⁻ 476.0.

3-(5-chlorothiophen-2-yl)-3-(4-(6-fluoro-7-(methylamino)-4-oxo-2H-benzo[e][1,3]oxazin-3(4H)-yl)benzylamino)propanoic acid (Compound 106);

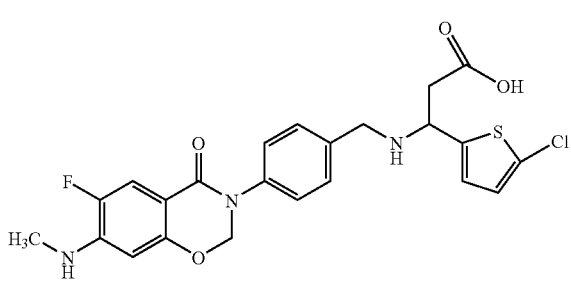

was prepared in a manner similar to Examples above. MS found: (M–H)⁻ 490.0.

1-((5-chlorothiophen-2-yl)methyl)-3-(4-(7-(4-fluorobenzylamino)-2,4-dioxo-1,2-dihydroquinazolin-3(4H)-yl)phenyl)urea (Compound 107);

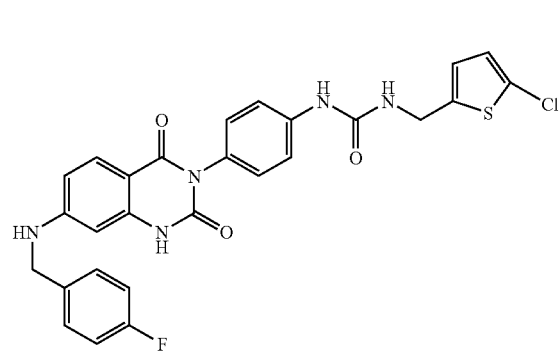

was prepared in a manner similar to Examples above. MS found: (M–H)⁻ 551.0.

2-(3-(4-(7-(4-fluorobenzylamino)-2,4-dioxo-1,2-dihydroquinazolin-3(4H)-yl)phenyl)ureido)-2-(thiophen-2-yl)acetic acid (Compound 108);

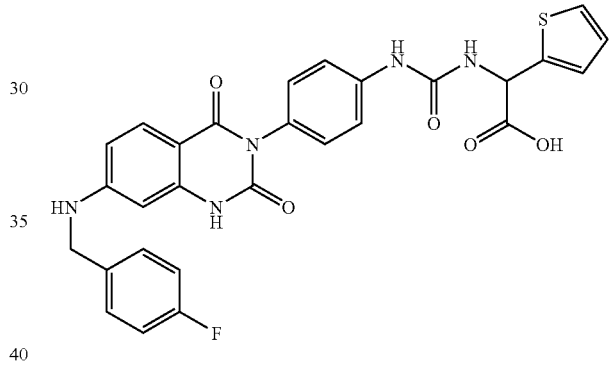

was prepared in a manner similar to Examples above. MS found: (M–H)⁻ 559.2.

2-(3-(4-(7-(4-fluorobenzylamino)-2,4-dioxo-1,2-dihydroquinazolin-3(4H)-yl)phenyl)ureido)-3-(thiophen-2-yl)propanoic acid (Compound 109);

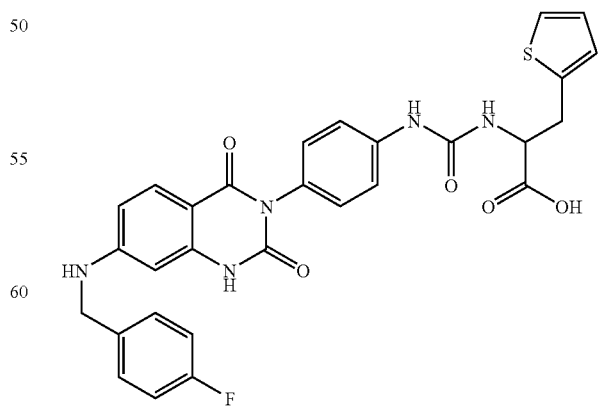

was prepared in a manner similar to Examples above. MS found: (M–H)⁻ 574.0.

81

2-(5-chlorothiophen-2-yl)-2-(5-(6-fluoro-7-(methylamino)-2,4-dioxo-1,2-dihydroquinazolin-3(4H)-yl)thiophene-2-carboxamido)acetic acid (Compound 112);

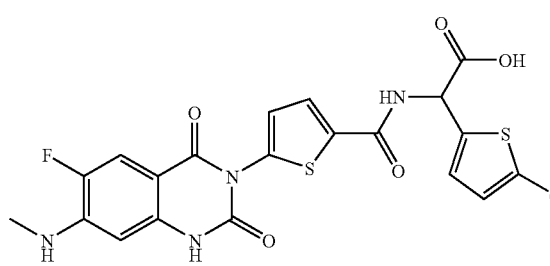

was prepared in a manner similar to Examples above. MS found: (M–H)⁻ 509.0.

2-(5-chlorothiophen-2-yl)-2-(5-(6-fluoro-7-(methylamino)-2,4-dioxo-1,2-dihydroquinazolin-3(4H)-yl)thiophene-3-carboxamido)acetic acid (Compound 113);

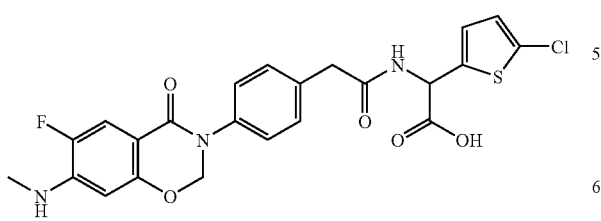

was prepared in a manner similar to Examples above. MS found: (M–H)⁻ 509.0.

2-(5-chlorothiophen-2-yl)-2-(2-(4-(6-fluoro-7-(methylamino)-4-oxo-2H-benzo[e][1,3]oxazin-3(4H)-yl)phenyl)acetamido)acetic acid (Compound 114);

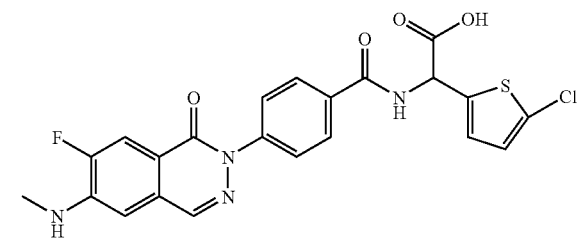

was prepared in a manner similar to Examples above. MS found: (M–H)⁻ 504.0.

82

2-(5-chlorothiophen-2-yl)-2-(4-(7-fluoro-6-(methylamino)-1-oxoisoquinolin-2(1H)-yl)benzylamino)acetic acid (Compound 115);

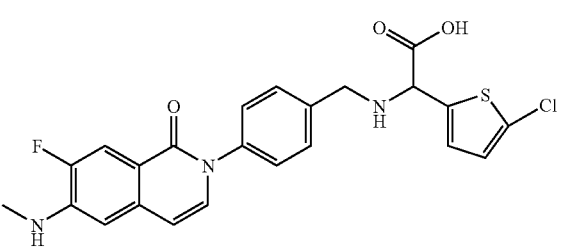

was prepared in a manner similar to Examples above. MS found: (M–H)⁻ 472.0.

2-(5-chlorothiophen-2-yl)-2-(4-(6-fluoro-7-(methylamino)-4-oxoquinazolin-3(4H)-yl)benzamido)acetic acid (Compound 116);

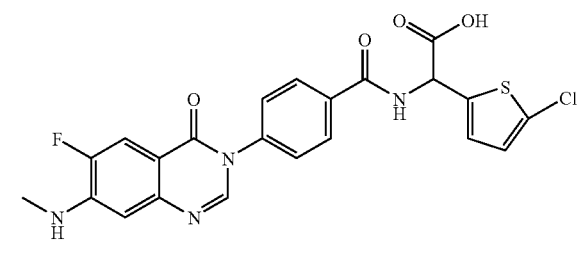

was prepared in a manner similar to Examples above. MS found: (M–H)⁻ 487.0.

2-(5-chlorothiophen-2-yl)-2-(4-(7-fluoro-6-(methylamino)-1-oxophthalazin-2(1H)-yl)benzamido)acetic acid (Compound 117);

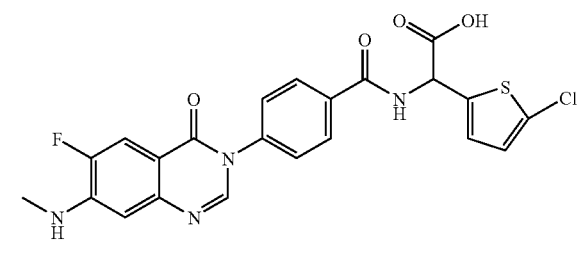

was prepared in a manner similar to Examples above. MS found: (M–H)⁻ 487.0.

methyl 2-(5-chlorothiophen-2-yl)-2-(2-(4-(6-fluoro-7-(methylamino)-4-oxo-2H-benzo[e][1,3]oxazin-3(4H)-yl)phenyl)acetamido)acetate (Compound 118);

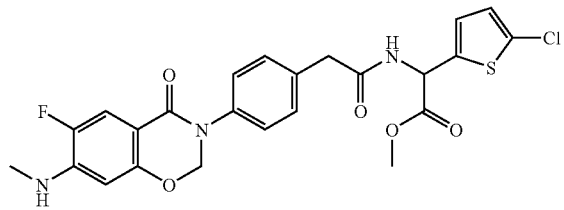

was prepared in a manner similar to Examples above. MS found: (M–H)⁻ 518.0.

2-(5-chlorothiophen-2-yl)-2-(4-(6-ethyl-1-oxo-3,4-dihydroisoquinolin-2(1H)-yl)benzamido)acetic acid (Compound 119);

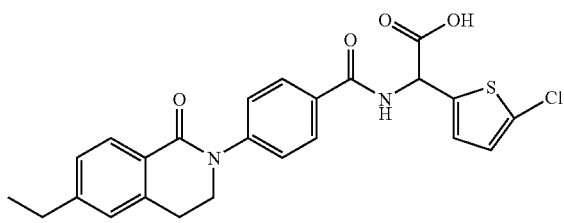

was prepared in a manner similar to Examples above. MS found: (M–H)⁻ 469.0.

2-(5-chlorothiophen-2-yl)-2-(2-(4-(6-fluoro-7-(methylamino)-4-oxo-2H-benzo[e][1,3]oxazin-3(4H)-yl)phenyl)acetamido)-N,N-dimethylacetamide (Compound 120);

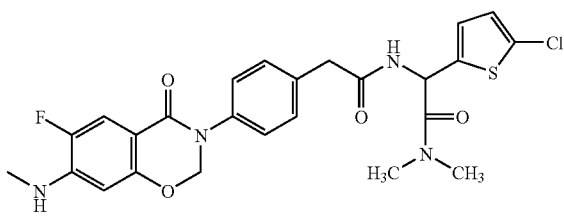

was prepared in a manner similar to Examples above. MS found: (M–H)⁻ 558.0.

N-(1-(5-chlorothiophen-2-yl)-2-oxo-2-(pyrrolidin-1-yl)ethyl)-2-(4-(6-fluoro-7-(methylamino)-4-oxo-2H-benzo[e][1,3]oxazin-3(4H)-yl)phenyl)acetamide (Compound 121); and

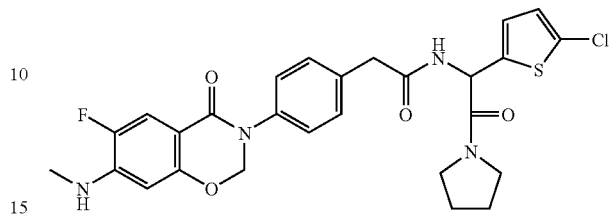

was prepared in a manner similar to Examples above. MS found: (M–H)⁻ 558.0.

N-(2-amino-1-(5-chlorothiophen-2-yl)-2-oxoethyl)-2-(4-(6-fluoro-7-(methylamino)-4-oxo-2H-benzo[e][1,3]oxazin-3(4H)-yl)phenyl)acetamide (Compound 122).

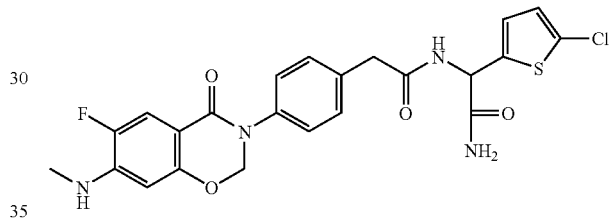

was prepared in a manner similar to Examples above. MS found: (M–H)⁻ 503.0.

Example 123

Pharmacological Assays

The pharmacological activity of each of the compounds according to the invention is determined by the following in vitro assays:

I. Inhibition of ADP-Mediated Platelet Aggregation In Vitro

1.

The effect of testing the compound according to the invention on ADP-induced human platelet aggregation was assessed in a 96-well microtiter assay (see generally the procedures in Jantzen, H. M. et al. (1999) *Thromb. Hemost.* 81:111-117) or standard cuvette light transmittance aggregometry using either human platelet-rich plasma (PRP) or human washed platelets.

For preparation of human platelet-rich plasma for aggregation assays, human venous blood was collected from healthy, drug-free volunteers into 0.38% sodium citrate (0.013 M, pH 7.0 final). Platelet-rich plasma (PRP) is prepared by centrifugation of whole blood at 160×g for 20 minutes at room temperature. The PRP layer is removed, transferred to a new tube, and the platelet count is adjusted, if necessary, to achieve a platelet concentration of ~3×10⁸ platelets/ml using platelet-poor plasma (PPP). PPP is prepared by centrifugation of the remaining blood sample (after removal of PRP) for 20 minutes at 800×g. This preparation of PRP can subsequently be used for aggregation assays in either a 96-well plate or standard cuvette aggregometry.

For preparation of washed platelets, human venous blood is collected from healthy, drug-free volunteers into ACD (85 mM sodium citrate, 111 mM glucose, 71.4 mM citric acid) containing $PGI_2$ (1.25 ml ACD containing 0.2 µM $PGI_2$ final; $PGI_2$ was from Sigma, St. Louis, Mo.). Platelet-rich plasma (PRP) is prepared by centrifugation at 160×g for 20 minutes at room temperature. Washed platelets are prepared by centrifuging PRP for 10 minutes at 730 g and resuspending the platelet pellet in CGS (13 mM sodium citrate, 30 mM glucose, 120 mM NaCl; 2 ml CGS/10 ml original blood volume) containing 1U/ml apyrase (grade V, Sigma, St. Louis, Mo.). After incubation at 37° C. for 15 minutes, the platelets are collected by centrifugation at 730 g for 10 minutes and resuspended at a concentration of $3\times10^8$ platelets/ml in Hepes-Tyrode's buffer (10 mM Hepes, 138 mM NaCl, 5.5 mM glucose, 2.9 mM KCl, 12 mM $NaHCO_3$, pH 7.4) containing 0.1% bovine serum albumin, 1 mM $CaCl_2$ and 1 mM $MgCl_2$. This platelet suspension is kept >45 minutes at 37° C. before use in aggregation assays.

2.

For cuvette light transmittance aggregation assays, serial dilutions (1:3) of test compounds were prepared in 100% DMSO in a 96 well V-bottom plate (final DMSO concentration in the cuvette was 0.6%). The test compound (3 µl of serial dilutions in DMSO) was preincubated with PRP for 30-45 seconds prior to initiation of aggregation reactions, which were performed in a ChronoLog aggregometer by addition of agonist (5 or 10 µM ADP) to 490 µL of PRP at 37° C. In some cases, light transmittance aggregometry was performed using 490 µL of washed platelets (prepared as described above) at 37° C., and aggregation was initiated by addition of 5 µM ADP and 0.5 mg/ml human fibrinogen (American Diagnostics, Inc., Greenwich, Conn.). The aggregation reaction is recorded for ~5 min, and maximum extent of aggregation is determined by the difference in extent of aggregation at baseline, compared to the maximum aggregation that occurs during the five minute period of the assay. Inhibition of aggregation was calculated as the maximum aggregation observed in the presence of inhibitor, compared to that in the absence of inhibitor. $IC_{50}$s were derived by non-linear regression analysis using the Prism software (GraphPad, San Diego, Calif.).

3.

Inhibition of ADP-dependent aggregation was also determined in 96-well flat-bottom microtiter plates using a microtiter plate shaker and plate reader similar to the procedure described by Frantantoni et al., *Am. J. Clin. Pathol.* 94, 613 (1990). All steps are performed at room temperature. For 96-well plate aggregation using platelet-rich plasma (PRP), the total reaction volume of 0.2 ml/well includes 180 µl of PRP (~$3\times10^8$ platelets/ml, see above), 6 µl of either serial dilution of test compounds in 20% DMSO or buffer (for control wells), and 10 µl of 20×ADP agonist solution (100 µM). The OD of the samples is then determined at 450 nm using a microtiter plate reader (Softmax, Molecular Devices, Menlo Park, Calif.) resulting in the 0 minute reading. The plates are then agitated for 5 min on a microtiter plate shaker and the 5 minute reading is obtained in the plate reader. Aggregation is calculated from the decrease of OD at 450 nm at t=5 minutes compared to t=0 minutes and is expressed as % of the decrease in the ADP control samples after correcting for changes in the unaggregated control samples. $IC_{50}$s were derived by non-linear regression analysis.

For 96-well plate aggregation using washed platelets, the total reaction volume of 0.2 ml/well includes in Hepes-Tyrodes buffer/0.1% BSA: $4.5\times10^7$ apyrase-washed platelets, 0.5 mg/ml human fibrinogen (American Diagnostica, Inc., Greenwich, Conn.), serial dilutions of test compounds (buffer for control wells) in 0.6% DMSO. After ~5 minutes preincubation at room temperature, ADP is added to a final concentration of 2 µM which induces submaximal aggregation. Buffer is added instead of ADP to one set of control wells (ADP-control). The OD of the samples is then determined at 450 nm using a microtiter plate reader (Softmax, Molecular Devices, Menlo Park, Calif.) resulting in the 0 minute reading. The plates are then agitated for 5 min on a microtiter plate shaker and the 5 minute reading is obtained in the plate reader. Aggregation is calculated from the decrease of OD at 450 nm at t=5 minutes compared to t=0 minutes and is expressed as % of the decrease in the ADP control samples after correcting for changes in the unaggregated control samples. $IC_{50}$s were derived by non-linear regression analysis.

II. Inhibition of [3H]2-MeS-ADP Binding to Platelets

1. The Ability of Candidate Molecules to Inhibit the Binding of [$^3$H]2-MeS-ADP to the $P2Y_1$ Receptor on Platelets was Determined Using a Radioligand Binding Assay.

Utilizing this assay the potency of inhibition of such compounds with respect to [$^3$H]2-MeS-ADP binding to whole platelets is determined. Under the conditions described in II (3) below, the binding of [$^3$H]2-MeS-ADP is solely due to the interaction of this ligand with the $P2Y_{12}$ receptor, in that all the specific binding measured in this assay is competable with a $P2Y_{12}$ antagonist (i.e., the specific binding is reduced to background levels by competition with an excess of $P2Y_{12}$ antagonist, with no competition of binding when a $P2Y_1$ antagonist is pre-incubated with the platelet preparation). [$^3$H]2-MeS-ADP binding experiments are routinely performed with outdated human platelets collected by standard procedures at hospital blood banks. Apyrase-washed outdated platelets are prepared as follows (all steps at room temperature, if not indicated otherwise):

Outdated platelet suspensions are diluted with 1 volume of CGS and platelets pelleted by centrifugation at 1900×g for 45 minutes. Platelet pellets are resuspended at $3-6\times10^9$ platelets/ml in CGS containing 1 U/ml apyrase (grade V, Sigma, St. Louis, Mo.) and incubated for 15 minutes at 37° C. After centrifugation at 730×g for 20 minutes, pellets are resuspended in Hepes-Tyrode's buffer containing 0.1% BSA (Sigma, St. Louis, Mo.) at a concentration of $6.66\times10^8$ platelets/ml. Binding experiments are performed after >45 minutes resting of the platelets.

2.

Alternatively, binding experiments are performed with fresh human platelets prepared as described in section I (Inhibition of ADP-Mediated Platelet Aggregation in vitro), except that platelets are resuspended in Hepes-Tyrode's buffer containing 0.1% BSA (Sigma, St. Louis, Mo.) at a concentration of $6.66\times10^8$ platelets/mil. Very similar results are obtained with fresh and outdated platelets.

3.

A platelet ADP receptor binding assay (ARB) using the tritiated potent agonist ligand [$^3$H]2-MeS-ADP (Jantzen, H. M. et al. (1999) *Thromb. Hemost.* 81:111-117) has been adapted to the 96-well microtiter format. In an assay volume of 0.2 ml Hepes-Tyrode's buffer with 0.1% BSA and 0.6% DMSO, $1\times10^8$ apyrase-washed platelets are preincubated in 96-well flat bottom microtiter plates for 5 minutes with serial dilutions of test compounds before addition of 1 nM [$^3$H]2-

MeS-ADP ([³H]2-methylthioadenosine-5'-diphosphate, ammonium salt; specific activity 20-50 Ci/mmole, obtained by custom synthesis from Amersham Life Science, Inc., Arlington Heights, Ill., or NEN Life Science Products, Boston, Mass.). Total binding is determined in the absence of test compounds. Samples for nonspecific binding may contain 10 µM unlabelled 2-MeS-ADP (RBI, Natick, Mass.). After incubation for 15 minutes at room temperature, unbound radioligand is separated by rapid filtration and two washes with cold (4-8° C.) Binding Wash Buffer (10 mM Hepes pH 7.4, 138 mM NaCl) using a 96-well cell harvester (Minidisc 96, Skatron Instruments, Sterling, Va.) and 8×12 GF/C glassfiber filtermats (Printed Filtermat A, for 1450 Microbeta, Wallac Inc., Gaithersburg, Md.). The platelet-bound radioactivity on the filtermats is determined in a scintillation counter (Microbeta 1450, Wallac Inc., Gaithersburg, Md.). Specific binding is determined by subtraction of non-specific binding from total binding, and specific binding in the presence of test compounds is expressed as % of specific binding in the absence of test compound dilutions. $IC_{50}$s were derived by non-linear regression analysis.

In the table below, activity in the PRP assay is provided as follows: +++, $IC_{50}$<10 µM; ++, 10 µM<$IC_{50}$<30 µM; and +, $IC_{50}$>30 µM. Activity in the ARB assay is provided as follows: +++, $IC_{50}$<0.05 µM; ++, 0.05 µM<$IC_{50}$<0.5 µM; and +, $IC_{50}$>0.5 µM.

TABLE 1

Activity of the compounds in ARB and PRP assays

| Compound No. | ARB (µM) | PRP (µM) |
|---|---|---|
| 1 | ++ | + |
| 2 | ++ | + |
| 3 | ++ | |
| 4 | ++ | |
| 5 | +++ | ++ |
| 6 | ++ | + |
| 7 | +++ | +++ |
| 8 | + | |
| 9 | + | |
| 10 | + | |
| 11 | ++ | + |
| 12 | + | |
| 13 | ++ | +++ |
| 14 | + | |
| 15 | ++ | |
| 16 | ++ | +++ |
| 18 | + | |
| 19 | ++ | +++ |
| 20 | ++ | |
| 21 | +++ | +++ |
| 22 | + | |
| 23 | + | |
| 24 | + | |
| 25 | ++ | |
| 26 | + | |
| 27 | ++ | + |
| 28 | + | |
| 29 | + | |
| 30 | + | |
| 31 | + | |
| 32 | ++ | +++ |
| 33 | + | |
| 34 | + | |
| 35 | ++ | ++ |
| 36 | ++ | |
| 37 | ++ | |
| 38 | + | |
| 39 | + | |
| 40 | + | |
| 41 | ++ | ++ |
| 42 | + | |
| 43 | ++ | |

TABLE 1-continued

Activity of the compounds in ARB and PRP assays

| Compound No. | ARB (µM) | PRP (µM) |
|---|---|---|
| 44 | ++ | ++ |
| 45 | +++ | +++ |
| 46 | ++ | ++ |
| 47 | ++ | +++ |
| 48 | ++ | |
| 49 | + | |
| 50 | ++ | + |
| 51 | + | |
| 52 | ++ | |
| 53 | ++ | + |
| 54 | +++ | ++ |
| 55 | ++ | + |
| 56 | +++ | ++ |
| 57 | ++ | |
| 58 | ++ | |
| 59 | + | |
| 60 | ++ | |
| 61 | +++ | ++ |
| 62 | +++ | + |
| 63 | + | |
| 64 | ++ | |
| 65 | ++ | |
| 66 | ++ | |
| 67 | ++ | |
| 68 | + | |
| 69 | + | |
| 70 | ++ | ++ |
| 71 | +++ | ++ |
| 72 | + | |
| 73 | ++ | |
| 74 | ++ | + |
| 75 | +++ | ++ |
| 76 | + | |
| 77 | + | |
| 78 | ++ | |
| 79 | ++ | +++ |
| 80 | ++ | + |
| 81 | ++ | + |
| 82 | ++ | + |
| 83 | + | |
| 84 | + | |
| 85 | ++ | |
| 86 | + | |
| 87 | +++ | |
| 88 | +++ | |
| 89 | +++ | |
| 90 | +++ | ++ |
| 91 | +++ | ++ |
| 92 | + | |
| 93 | + | |
| 94 | + | |
| 95 | + | |
| 96 | + | |
| 97 | + | |
| 98 | + | |
| 99 | + | |
| 100 | + | |
| 101 | + | |
| 102 | + | |
| 103 | + | |
| 104 | ++ | |
| 105 | ++ | + |
| 106 | ++ | + |
| 107 | +++ | |
| 108 | ++ | |
| 109 | ++ | |
| 110 | + | |
| 111 | + | |
| 112 | ++ | |
| 113 | + | |
| 114 | + | |
| 115 | ++ | + |
| 116 | ++ | |
| 117 | ++ | |
| 118 | ++ | |

TABLE 1-continued

Activity of the compounds in ARB and PRP assays

| Compound No. | ARB (μM) | PRP (μM) |
|---|---|---|
| 119 | + | |
| 120 | + | |
| 121 | + | |
| 122 | ++ | |

It should be understood that the foregoing discussion, embodiments and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound having the formula (I):

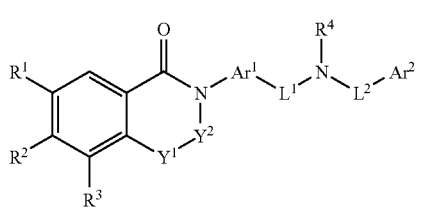

wherein
$Y^1$ is NH;
$Y^2$ is CO,
each $R^1$, $R^2$ and $R^3$ is independently selected from the group consisting of H, $C_{1-6}$alkyl, $C_{2-6}$ alkenyl, $C_{2-6}$ alkynyl, —$N(R^7)_2$, $C_{1-6}$alkoxy, halogen, $C_{1-6}$haloalkyl, hydroxy$C_{1-6}$alkyl, cyano, —C(O)$R^6$, $C_{3-6}$cycloalkyl, $C_{3-6}$cycloalkyl-$C_{1-6}$alkyl, aryl and aryl$C_{1-6}$alkyl, wherein each of said $C_{1-6}$alkyl, $C_{2-6}$ alkenyl, $C_{2-6}$ alkynyl and aryl portions is optionally substituted with from 1 to 3 substituents, each independently selected from the group consisting of $C_{1-6}$ alkyl, $C_{2-6}$ alkenyl, $C_{2-6}$ alkynyl, amino, $C_{1-6}$alkoxy, halogen, hydroxyl, cyano, oxo, thio, $C_{3-6}$cycloalkyl, aryl and heteroaryl;
$R^4$ is H or —$(CH_2)_mCO_2H$;
$R^6$ is selected from the group consisting of hydroxy, $C_{1-6}$alkyl, $C_{1-6}$alkoxy, heterocyclyl$C_{1-6}$alkoxy and —$N(R^7)_2$;
each $R^7$ is independently selected from the group consisting of H, $C_{1-6}$alkyl and aryl$C_{1-6}$alkyl or optionally, two $R^7$ groups attached to nitrogen are combined with the nitrogen atom to form an azetidine, pyrrolidine, piperidine or morpholine ring; wherein each of said $C_{1-6}$ alkyl and aryl$C_{1-6}$ alkyl is optionally substituted with from 1 to 3 substituents, each independently selected from the group consisting of halogen, amino, hydroxyl, $C_{1-6}$ alkoxy, cyano, $C_{1-6}$ alkyl, $C_{3-6}$ cycloalkyl, aryl, and heteroaryl;
$Ar^1$ is an aromatic ring selected from the group consisting of benzene and thiophene, each of which is optionally substituted with from 1-2 $R^8$ substituents,
$Ar^2$ is an aromatic ring selected from the group consisting of benzene, tetrazole and thiophene, each of which is optionally substituted with from 1-2 $R^8$ substituents,
each $R^8$ is independently selected from the group consisting of halogen, cyano, hydroxy, $C_{1-6}$alkyl, $C_{2-6}$alkenyl, $C_{2-6}$alkynyl, $C_{1-6}$alkoxy, halo$C_{1-6}$alkyl, halo$C_{1-6}$alkoxy, $C_{3-5}$cycloalkyl-$C_{1-6}$alkoxy, —$NR^7$, —C(=$NR^{8a}$)—N($R^{8b})_2$, —C(O)$R^{8a}$, —O(CH$_2)_mOR^{8b}$, —(CH$_2)_mOR^{8b}$, —O(CH$_2)_mN(R^{8b})_2$ and —(CH$_2)_mN(R^{8b})_2$,
each $R^{8a}$ is a member independently selected from the group consisting of H, hydroxy, $C_{1-6}$alkyl, $C_{1-6}$alkoxy and —$NR^7$;
each $R^{8b}$ is a member independently selected from the group consisting of H, $C_{1-4}$alkyl and $C_{1-4}$alkanoyl, and optionally, two $R^{8b}$ groups attached to nitrogen are combined with the nitrogen atom to form an azetidine, pyrrolidine, piperidine or morpholine ring; wherein each of said $C_{1-4}$ alkyl and $C_{1-4}$ alkanoyl is optionally substituted with from 1 to 3 substituents, each independently selected from the group consisting of halogen, amino, hydroxyl, $C_{1-6}$ alkoxy, cyano, $C_{1-6}$ alkyl, $C_{3-6}$ cycloalkyl, aryl, and heteroaryl;
$L^1$ is a linking group selected from the group consisting of —CO— and —$CH_2$—,
$L^2$ is a linking group selected from the group consisting of a —C($R^9)_2$—, —C($R^9)_2CH_2$— and —CO—;
each $R^9$ is independently selected from the group consisting of H, $C_{1-6}$alkyl, —$(CH_2)_mC(O)R^6$, —C(O)$R^6$ and heterocyclyl substituted with from 0 to 2 substituents selected from the group halogen, cyano, $C_{1-6}$alkyl, $C_{2-6}$alkenyl, $C_{2-6}$alkynyl, $C_{1-6}$alkoxy, halo$C_{1-6}$alkyl, oxo and thio;
each subscript m is independently 1, 2 or 3,
or pharmaceutically acceptable salts thereof.

2. A compound of claim 1, wherein $Ar^1$ is benzene, which is optionally substituted with from 1-2 $R^8$ substituents.

3. A compound of claim 1, wherein $Ar^1$ is thiophene, which is optionally substituted with from 1-2 $R^8$ substituents.

4. A compound of claim 1, wherein $Ar^2$ is tetrazole, which is optionally substituted with from 1-2 $R^8$ substituents.

5. A compound of claim 1, wherein $Ar^2$ is benzene, which is optionally substituted with from 1-2 $R^8$ substituents.

6. A compound of claim 1, wherein $Ar^2$ is thiophene, which is optionally substituted with from 1-2 $R^8$ substituents.

7. A compound of claim 1, wherein at least one $R^9$ is —C(O)$R^6$.

8. A compound of claim 1, wherein at least one $R^9$ is —$(CH_2)_mC(O)R^6$.

9. A compound of claim 1, wherein at least one $R^9$ is heterocyclyl.

10. A compound of claim 9, wherein at least one $R^9$ is independently selected from the group consisting of:

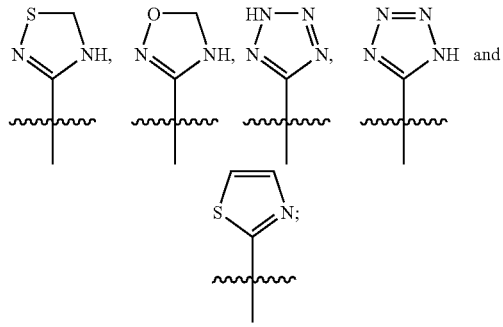

each of which is substituted with from 0 to 2 substituents selected from the group consisting of halogen, cyano, $C_{1-6}$alkyl, $C_{2-6}$alkenyl, $C_{2-6}$ alkynyl, $C_{1-6}$alkoxy, halo$C_{1-6}$alkyl, oxo and thio; and wherein the wavy line indicates the point of attachment to the rest of the molecule.

11. A compound of claim 9, wherein at least one $R^9$ is independently selected from the group consisting of:

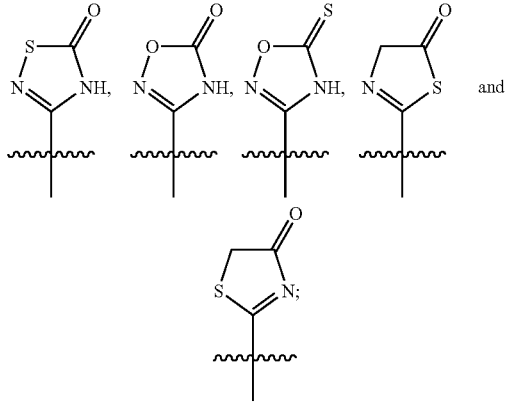

and wherein the wavy line indicates the point of attachment to the rest of the molecule.

12. A compound of claim 1, having the formula:

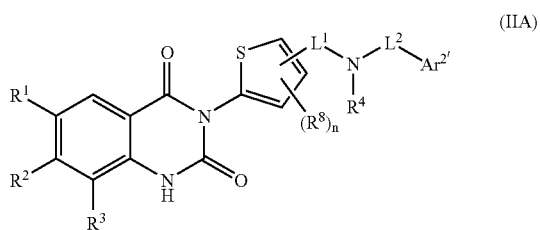

(IIA)

wherein the subscript n is an integer of from 0 to 2.

13. A compound of claim 12, wherein $R^1$ is H, NHR$^7$ or halogen; $R^2$ is H, $C_{1-6}$alkyl, NHR$^7$ or halogen; $R^3$ is H; $R^7$ is $C_{1-6}$alkyl or aryl$C_{1-6}$alkyl; $R^8$ is halogen, or $C_{1-6}$alkoxy; Ar$^2$ is thiophene or benzene, each of which is optionally substituted with from 1-2 $R^8$ substituents; and n is 1.

14. A compound of claim 13, wherein $R^1$ is F, $R^2$ is NH R$^7$, and $R^7$ is CH$_3$ or 4-fluorobenzyl.

15. A compound of claim 1, selected from the group consisting of:
  2-(5-chlorothiophen-2-yl)-2-(5-(6-fluoro-7-(methylamino)-2,4-dioxo-1,2-dihydroquinazolin-3(4H)-yl) thiophene-2-carboxamido)acetic acid; and
  2-(5-chlorothiophen-2-yl)-2-(5-(6-fluoro-7-(methylamino)-2,4-dioxo-1,2-dihydroquinazolin-3(4H)-yl) thiophene-3-carboxamido)acetic acid.

16. A compound of claim 1, having the formula:

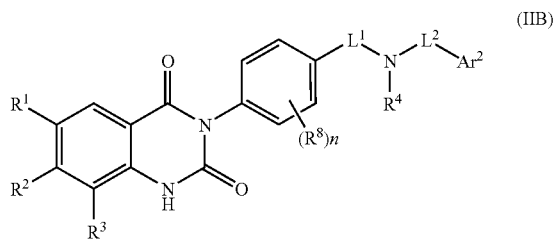

(IIB)

wherein the subscript n is an integer of from 0 to 2.

17. A compound of claim 16, wherein $R^1$ is H, NHR$^7$ or halogen; $R^2$ is H, $C_{1-6}$alkyl, NHR$^7$ or halogen; $R^3$ is H; $R^7$ is $C_{1-6}$alkyl or aryl$C_{1-6}$alkyl; $R^8$ is halogen, or $C_{1-6}$alkoxy; Ar$^2$ is thiophene or benzene, each of which is optionally substituted with from 1-2 $R^8$ substituents; and n is 1.

18. A compound of claim 16, wherein $R^1$ is F, $R^2$ is NHR$^7$, and $R^7$ is CH$_3$ or 4-fluorobenzyl.

19. A compound selected from the group consisting of:
  2-(4-(7-(4-fluorobenzylamino)-2,4-dioxo-1,2-dihydroquinazolin-3(4H)-yl)benzamido)-3-(thiophen-2-yl) propanoic acid;
  2-(4-(6-fluoro-7-(methylamino)-2,4-dioxo-1,2-dihydroquinazolin-3(4H)-yl)benzamido)-3-(thiophen-2-yl) propanoic acid;
  N-((1H-tetrazol-5-yl)methyl)-4-(7-(4-fluorobenzylamino)-2,4-dioxo-1,2-dihydroquinazolin-3(4H)-yl) benzamide;
  N-((3-chlorophenyl)(1H-tetrazol-5-yl)methyl)-4-(6-fluoro-7-(methylamino)-2,4-dioxo-1,2-dihydroquinazolin-3(4H)-yl)benzamide;
  N-((4-chlorophenyl)(1H-tetrazol-5-yl)methyl)-4-(6-fluoro-7-(methylamino)-2,4-dioxo-1,2-dihydroquinazolin-3(4H)-yl)benzamide;
  2-(4-chlorophenyl)-2-(4-(6-fluoro-7-(methylamino)-2,4-dioxo-1,2-dihydroquinazolin-3(4H)-yl)benzamido) acetic acid;
  2-(3-chlorophenyl)-2-(4-(6-fluoro-7-(methylamino)-2,4-dioxo-1,2-dihydroquinazolin-3(4H)-yl)benzamido) acetic acid;
  N-((1H-tetrazol-5-yl)(m-tolyl)methyl)-4-(6-fluoro-(methylamino)-2,4-dioxo-1,2-dihydroquinazolin-3 (4H)-yl)benzamide;
  4-(6-fluoro-7-(methylamino)-2,4-dioxo-1,2-dihydroquinazolin-3(4H)-yl)-N-((3-methoxyphenyl) (1H-tetrazol-5-yl)methyl)benzamide;
  4-(6-fluoro-7-(methylamino)-2,4-dioxo-1,2-dihydroquinazolin-3(4H)-yl)-N-((3-fluorophenyl) (1H-tetrazol-5-yl)methyl)benzamide;
  N-((2-chlorophenyl)(1H-tetrazol-5-yl)methyl)-4-(6-fluoro-7-(methylamino)-2,4-dioxo-1,2-dihydroquinazolin-3(4H)-yl)benzamide;
  N-((3,4-dichlorophenyl)(1H-tetrazol-5-yl)methyl)-4-(6-fluoro-7-(methylamino)-2,4-dioxo-1,2-dihydroquinazolin-3(4H)-yl)benzamide;
  N-((3,5-dichlorophenyl)(1H-tetrazol-5-yl)methyl)-4-(6-fluoro-7-(methylamino)-2,4-dioxo-1,2-dihydroquinazolin-3(4H)-yl)benzamide;
  N-((1H-tetrazol-5-yl)(3-(trifluoromethoxy)phenyl)methyl)-4-(6-fluoro-7-(methylamino)-2,4-dioxo-1,2-dihydroquinazolin-3(4H)-yl)benzamide;
  N-((1H-tetrazol-5-yl)(3-(trifluoromethyl)phenyl)methyl)-4-(6-fluoro-7-(methylamino)-2,4-dioxo-1,2-dihydroquinazolin-3(4H)-yl)benzamide;
  2-(5-chloro-N-(4-(6-fluoro-7-(methylamino)-2,4-dioxo-1,2-dihydroquinazolin-3(4H)-yl) benzyl)thiophene-2-carboxamido)acetic acid; and
  3-(5-chlorothiophen-2-yl)-3-(4-(6-fluoro-7-(methylamino)-2,4-dioxo-1,2-dihydroquinazolin-3(4H)-yl) benzylamino)propanoic acid.

20. A compound of claim 1, having the formula:

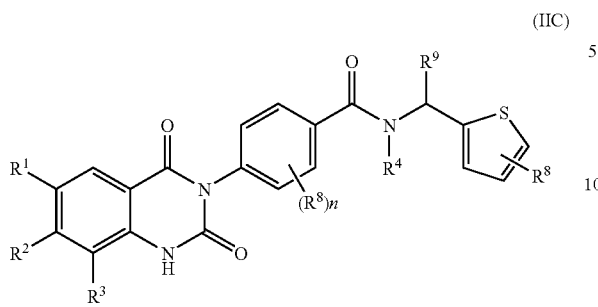

wherein the subscript n is an integer of from 0 to 2.

21. A compound of claim 20, wherein $R^1$ is F, $R^2$ is $NHR^7$, and $R^7$ is $CH_3$ or 4-fluorobenzyl.

22. A compound selected from the group consisting of:
- N-((5-chlorothiophen-2-yl)methyl)-4-(7-(4-fluorobenzylamino)-2,4-dioxo-1,2-dihydroquinazolin-3(4H)-yl) benzamide;
- 2-(4-(7-(4-fluorobenzylamino)-2,4-dioxo-1,2-dihydroquinazolin-3(4H)-yl)benzamido)-2-(thiophen-2-yl) acetic acid;
- N-((5-chlorothiophen-2-yl)methyl)-4-(6-fluoro-7-(methylamino)-2,4-dioxo-1,2-dihydroquinazolin-3(4H)-yl) benzamide;
- 2-(5-chlorothiophen-2-yl)-2-(4-(6-fluoro-7-(methylamino)-2,4-dioxo-1,2-dihydroquinazolin-3(4H)-yl) benzamido)acetic acid;
- 2-(N-((5-chlorothiophen-2-yl)methyl)-4-(6-fluoro-7-(methylamino)-2,4-dioxo-1,2-dihydroquinazolin-3(4H)-yl) benzamido)acetic acid;
- N((5-chlorothiophen-2-yl)(1H-tetrazol-5-yl)methyl)-4-(6-fluoro-7-(methylamino)-2,4-dioxo-1,2-dihydroquinazolin-3(4H)-yl)benzamide;
- 2-(4-(6-fluoro-7-(methylamino)-2,4-dioxo-1,2-dihydroquinazolin-3(4H)-yl)benzamido)-2-(thiophen-2-yl) acetic acid;
- 2-(5-chlorothiophen-2-yl)-2-(4-(6-fluoro-7-(methylamino)-2,4-dioxo-1,2-dihydroquinazolin-3(4H)-yl) benzamido)acetic acid;
- 2-(4-(6-fluoro-7-(methylamino)-2,4-dioxo-1,2-dihydroquinazolin-3(4H)-yl) benzamido)-2-(5-methylthiophen-2-yl)acetic acid;
- 2-(5-chlorothiophen-2-yl)-2-(4-(7-(methylamino)-2,4-dioxo-1,2-dihydroquinazolin-3(4H)-yl)benzamido)acetic acid;
- N-((5-chlorothiophen-2-yl)(5-oxo-4,5-dihydro-1,2,4-oxadiazol-3-yl)methyl)-4-(6-fluoro-7-(methylamino)-2,4-dioxo-1,2-dihydroquinazolin-3(4H)-yl)benzamide;
- N-((5-chlorothiophen-2-yl)(5-oxo-4,5-dihydro-1,2,4-thiadiazol-3-yl)methyl)-4-(6-fluoro-7-(methylamino)-2,4-dioxo-1,2-dihydroquinazolin-3(4H)-yl)benzamide;
- ethyl 2-(5-chlorothiophen-2-yl)-2-(4-(6-fluoro-7-(methylamino)-2,4-dioxo-1,2-dihydroquinazolin-3(4H)-yl) benzamido)acetate;
- 3-(5-chlorothiophen-2-yl)-3-(4-(6-fluoro-7-(methylamino)-2,4-dioxo-1,2-dihydroquinazolin-3(4H)-yl) benzamido)propanoic acid;
- N-((5-chlorothiophen-2-yl)(5-thioxo-4,5-dihydro-1,2,4-oxadiazol-3-yl)methyl)-4-(6-fluoro-7-(methylamino)-2,4-dioxo-1,2-dihydroquinazolin-3(4H)-yl)benzamide;
- 2-(5-chlorothiophen-2-yl)-2-(4-(2,4-dioxo-1,2-dihydroquinazolin-3(4H)-yl) benzamido)acetic acid;
- N-((1H-tetrazol-5-yl)(3-(trifluoromethyl)phenyl)methyl)-4-(6-fluoro-7-(methylamino)-2,4-dioxo-1,2-dihydroquinazolin-3(4H)-yl)benzamide;
- 2-morpholinoethyl 2-(5-chlorothiophen-2-yl)-2-(4-(6-fluoro-7-(methylamino)-2,4-dioxo-1,2-dihydroquinazolin-3(4H)-yl)benzamido)acetate;
- N-(1-(5-chlorothiophen-2-yl)-2-hydroxyethyl)-4-(6-fluoro-7-(methylamino)-2,4-dioxo-1,2-dihydroquinazolin-3(4H)-yl)benzamide;
- 2-(5-chlorothiophen-2-yl)-2-(4-(6-iodo-2,4-dioxo-1,2-dihydroquinazolin-3(4H)-yl) benzamido)acetic acid;
- 2-(5-chlorothiophen-2-yl)-2-(4-(6-isopropoxy-2,4-dioxo-1,2-dihydroquinazolin-3(4H)-yl) benzamido)acetic acid;
- 2-(5-chlorothiophen-2-yl)-2-(4-(2,4-dioxo-1,2-dihydroquinazolin-3(4H)-yl) benzamido)acetic acid;
- 3-(N-((5-chlorothiophen-2-yl)methyl)-4-(6-fluoro-7-(methylamino)-2,4-dioxo-1,2-dihydroquinazolin-3(4H)-yl) benzamido)propanoic acid;
- 2-(5-chlorothiophen-2-yl)-2-(4-(6-fluoro-7-(methylamino)-2,4-dioxo-1,2-dihydroquinazolin-3(4H)-yl)-2-methoxybenzamido)acetic acid;
- 2-(2-chloro-4-(6-fluoro-7-(methylamino)-2,4-dioxo-1,2-dihydroquinazolin-3(4H)-yl) benzamido)-2-(5-chlorothiophen-2-yl)acetic acid;
- 2-(5-chlorothiophen-2-yl)-2-(2-fluoro-4-(6-fluoro-7-(methylamino)-2,4-dioxo-1,2-dihydroquinazolin-3(4H)-yl) benzamido)acetic acid;
- N-(2-amino-1-(5-chlorothiophen-2-yl)-2-oxoethyl)-4-(6-fluoro-7-(methylamino)-2,4-dioxo-1,2-dihydroquinazolin-3(4H)-yl)benzamide;
- 2-(5-chlorothiophen-2-yl)-2-(4-(7-fluoro-6-(methylamino)-2,4-dioxo-1,2-dihydroquinazolin-3(4H)-yl) benzamido)acetic acid;
- N-((5-chlorothiophen-2-yl)(1H-tetrazol-5-yl)methyl)-4-(7-fluoro-6-(methylamino)-2,4-dioxo-1,2-dihydroquinazolin-3(4H)-yl)benzamide;
- N-((5-chlorothiophen-2-yl)(5-oxo-4,5-dihydro-1,2,4-oxadiazol-3-yl)methyl)-4-(7-fluoro-6-(methylamino)-2,4-dioxo-1,2-dihydroquinazolin-3(4H)-yl)benzamide;
- 2-(5-chlorothiophen-2-yl)-2-(4-(6-fluoro-7-(methylamino)-2,4-dioxo-1,2-dihydroquinazolin-3(4H)-yl)-3-methoxybenzamido)acetic acid;
- N-((5-chlorothiophen-2-yl)(1H-tetrazol-5-yl)methyl)-4-(6-fluoro-7-(methylamino)-2,4-dioxo-1,2-dihydroquinazolin-3(4H)-yl)-3-methoxybenzamide;
- N-((5-chlorothiophen-2-yl)(5-oxo-4,5-dihydro-1,2,4-oxadiazol-3-yl)methyl)-4-(6-fluoro-7-(methylamino)-2,4-dioxo-1,2-dihydroquinazolin-3(4H)-yl)-3-methoxybenzamide;
- 2-(5-chlorothiophen-2-yl)-2-(4-(6-ethyl-1-oxo-3,4-dihydroisoquinolin-2(1H)-yl) benzamido)acetic acid;
- 2-(1-((5-chlorothiophen-2-yl)methyl)-3-(4-(6-fluoro-7-(methylamino)-2,4-dioxo-1,2-dihydroquinazolin-3(4H)-yl)phenyl)-1H-1,2,4-triazol-5-ylthio)acetic acid; and
- 2-(5-chlorothiophen-2-yl)-2-(3-(6-fluoro-7-(methylamino)-2,4-dioxo-1,2-dihydroquinazolin-3(4H)-yl) benzamido)acetic acid.

23. The compound of claim 1:
N-((5-chlorothiophen-2-yl)(5-oxo-4,5-dihydro-1,2,4-oxadiazol-3-yl)methyl)-4-(6-fluoro-7-(methylamino)-2,4-dioxo-1,2-dihydroquinazolin-3(4H)-yl)benzamide.

24. The compound of claim 1:
(S)-N-((5-chlorothiophen-2-yl)(5-oxo-4,5-dihydro-1,2,4-oxadiazol-3-yl)methyl)-4-(6-fluoro-7-(methylamino)-2,4-dioxo-1,2-dihydroquinazolin-3(4H)-yl)benzamide.

25. The compound of claim 1:
(R)-N-((5-chlorothiophen-2-yl)(5-oxo-4,5-dihydro-1,2,4-oxadiazol-3-yl)methyl)-4-(6-fluoro-7-(methylamino)-2,4-dioxo-1,2-dihydroquinazolin-3(4H)-yl)benzamide.

26. A pharmaceutical composition comprising a pharmaceutically acceptable carrier and a compound according to claim 1.

* * * * *